US011331363B2

(12) United States Patent
Tripp et al.

(10) Patent No.: US 11,331,363 B2
(45) Date of Patent: *May 17, 2022

(54) PHYTOCOMPLEXES EXHIBITING MULTIPLE, SYNERGISTIC ANTIOXIDANT ACTIVITIES USEFUL IN FOODS, DIETARY SUPPLEMENTS, COSMETICS AND PHARMACEUTICAL PREPARATIONS

(71) Applicant: Nature's Sunshine Products, Inc., Lehi, UT (US)

(72) Inventors: Matthew L. Tripp, Saratoga Springs, UT (US); Clinton J. Dahlberg, Saratoga Springs, UT (US); John G. Babish, Brooktondale, NY (US); Wei Gao, Lehi, UT (US); Mohan Kaadige, Salt Lake City, UT (US); Sheryl Krig, Eden, UT (US); Xiaolan Kou, Lehi, UT (US); Zhe Khang, Provo, UT (US); Joseph Ou, Saratoga Springs, UT (US)

(73) Assignee: Nature's Sunshine Products, Inc., Lehi, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/596,540

(22) Filed: Oct. 8, 2019

(65) Prior Publication Data

US 2020/0246412 A1 Aug. 6, 2020

Related U.S. Application Data

(63) Continuation of application No. 15/072,333, filed on Mar. 16, 2016, now Pat. No. 10,434,131.

(60) Provisional application No. 62/133,945, filed on Mar. 16, 2015.

(51) Int. Cl.
| | |
|---|---|
| *A61K 36/73* | (2006.01) |
| *A61K 36/82* | (2006.01) |
| *A61K 36/87* | (2006.01) |
| *A61K 36/63* | (2006.01) |
| *A23L 33/105* | (2016.01) |
| *A23L 33/00* | (2016.01) |
| *A61K 9/00* | (2006.01) |
| *A61K 31/122* | (2006.01) |
| *A61K 31/202* | (2006.01) |
| *A61K 31/4375* | (2006.01) |
| *A61K 36/38* | (2006.01) |
| *A61K 36/45* | (2006.01) |
| *A61K 36/752* | (2006.01) |
| *A61K 36/81* | (2006.01) |
| *A61K 36/9066* | (2006.01) |

(52) U.S. Cl.
CPC ............ *A61K 36/73* (2013.01); *A23L 33/105* (2016.08); *A23L 33/40* (2016.08); *A61K 9/0053* (2013.01); *A61K 31/122* (2013.01); *A61K 31/202* (2013.01); *A61K 31/4375* (2013.01); *A61K 36/38* (2013.01); *A61K 36/45* (2013.01); *A61K 36/63* (2013.01); *A61K 36/752* (2013.01); *A61K 36/81* (2013.01); *A61K 36/82* (2013.01); *A61K 36/87* (2013.01); *A61K 36/9066* (2013.01)

(58) Field of Classification Search
CPC .... A61K 2300/00; A61K 36/63; A61K 36/73; A61K 36/82; A61K 36/87; A61K 31/122; A61K 31/202; A61K 31/4375; A61K 36/38; A61K 36/45; A61K 36/752; A61K 36/81; A61K 36/9066; A61K 9/0053; A23L 33/105; A23L 33/40; A61P 39/06; A61P 3/00; A61P 43/00
See application file for complete search history.

(56) References Cited

U.S. PATENT DOCUMENTS

| 8,962,058 B2 | 2/2015 | Prakash et al. |
| 8,968,791 B2 | 3/2015 | Moore et al. |
| 10,434,131 B2 * | 10/2019 | Tripp ................. A61K 36/81 |
| 2004/0023894 A1 | 2/2004 | Hasler-Nguyen et al. |
| 2005/0048143 A1 | 3/2005 | Mcanalley et al. |
| 2006/0088643 A1 | 4/2006 | Fugal et al. |
| 2006/0172012 A1 | 8/2006 | Finley et al. |
| 2008/0119551 A1 | 5/2008 | Iwasaki et al. |
| 2009/0136469 A1 | 5/2009 | Senin et al. |

(Continued)

FOREIGN PATENT DOCUMENTS

| CN | 102413824 | 4/2012 |
| CN | 104379157 | 2/2015 |

(Continued)

OTHER PUBLICATIONS

European Search Report dated Nov. 6, 2018 (European Patent Application No. 16765698.2); 7 pages.

*Primary Examiner* — Blaine Lankford
(74) *Attorney, Agent, or Firm* — Thorpe North and Western, LLP; David W. Osborne

(57) ABSTRACT

Compositions comprising apple, grape, green tea, and olive extracts are presented herein. This synergistic formulations apple, grape, green tea, and olive extract are in amounts that provide a greater antioxidant activity or protein kinase modulating activity than provided by an equivalent amount of any one extract or a sum of the extracts. Further presented are methods of regulating oxidative stress, disease-associated protein kinase activity, and enhancing the therapeutic effect of a primary therapeutic agent. Also presented are methods of making an activity enhancing composition for regulating oxidative stress, disease-associated protein kinase activity, and enhancing the therapeutic effect of a primary therapeutic agent.

7 Claims, 3 Drawing Sheets

(56) References Cited

U.S. PATENT DOCUMENTS

| | | |
|---|---|---|
| 2010/0215783 A1 | 8/2010 | McNeaiy |
| 2011/0300083 A1 | 12/2011 | Yontz et al. |
| 2012/0058140 A1 | 3/2012 | Ceccoli et al. |
| 2013/0123207 A1 | 5/2013 | Sardi |
| 2015/0056255 A1 | 2/2015 | Ragot et al. |

FOREIGN PATENT DOCUMENTS

| | | |
|---|---|---|
| WO | WO 2012/129683 A1 | 10/2012 |
| WO | WO 2014/088520 A1 | 6/2014 |

* cited by examiner

PHYTOCOMPLEXES EXHIBITING MULTIPLE, SYNERGISTIC ANTIOXIDANT ACTIVITIES USEFUL IN FOODS, DIETARY SUPPLEMENTS, COSMETICS AND PHARMACEUTICAL PREPARATIONS

PRIORITY DATA

This application is a continuation of U.S. patent application Ser. No. 15/072,333, filed Mar. 16, 2016, now issued as U.S. Pat. No. 10,434,131, which claims the benefit to U.S. Provisional Patent Application Ser. No. 62/133,945 filed on Mar. 16, 2015, each of which is incorporated herein by reference.

BACKGROUND OF THE INVENTION

Oxidative stress influences a number of in-vivo metabolic pathways and is implicated in many pathophysiological conditions including disorders associated with tissue-specific modulation of protein kinase activity stimulated through the propagation of reactive species of oxygen and nitrogen. Oxidative stress related pathologies and metabolic disorders can include metabolic syndrome, type I and type II diabetes, obesity, high cholesterol levels accompanied by increased oxidized LDL cholesterol, atherosclerosis, arterial hypertension and various forms of inflammation to name just a few.

BRIEF DESCRIPTION OF THE DRAWINGS

Features and advantages of the invention will be apparent from the detailed description that follows, and which taken in conjunction with the accompanying figures, together illustrate features of the invention. It is understood that the figures merely depict exemplary embodiments and are, therefore, not to be considered limiting in scope.

DESCRIPTION OF EMBODIMENTS

Figure 1:
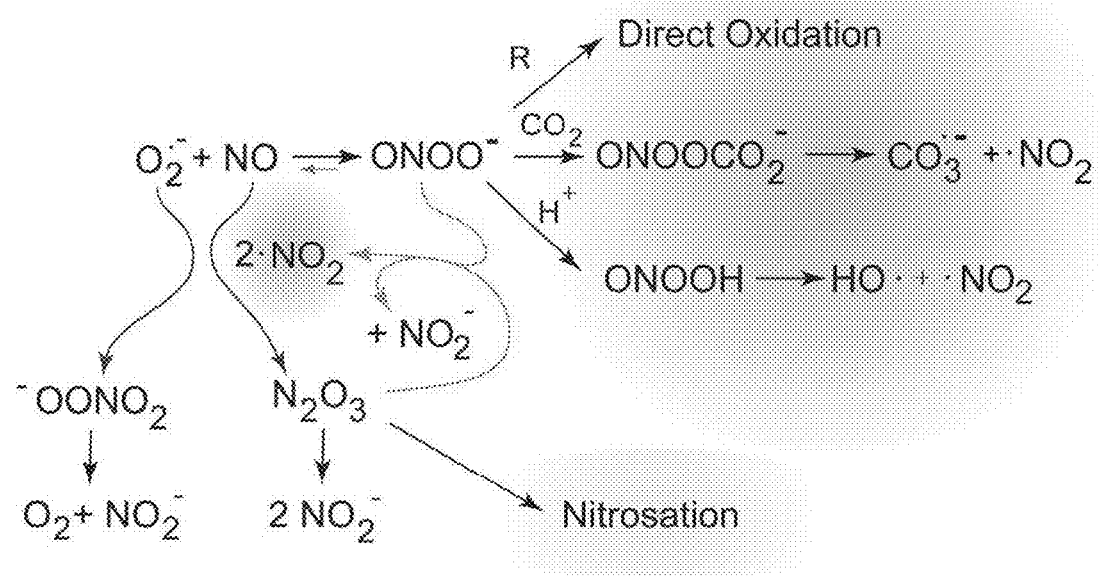
FIG. 1 schematically displays the interplay of nitric oxide, superoxide, peroxynitrite and nitrogen dioxide in a cell.

Before invention embodiments are disclosed and described, it is to be understood that no limitation to the particular structures, process steps, or materials disclosed herein is intended, but also includes equivalents thereof as would be recognized by those ordinarily skilled in the relevant arts. It should also be understood that terminology employed herein is used to describe particular examples only and is not intended to be limiting. The same reference numerals in different drawings represent the same element. Numbers provided in flow charts and processes are provided for clarity in illustrating steps and operations and do not necessarily indicate a particular order or sequence. Unless defined otherwise, all technical and scientific terms used herein have the same meaning as commonly understood by one of ordinary skill in the art to which this disclosure belongs. In the specification and the appended claims, the singular forms include plural referents unless the context clearly dictates otherwise.

As used in this specification, the singular forms "a," "an," and "the" specifically also plural referents, unless the content clearly dictates otherwise. For example, "an excipient" refers to one or more excipients.

Additionally, as used herein, unless specifically indicated otherwise, the word "or" is used in the "inclusive" sense of "and/or" and not the "exclusive" sense of "either/or."

The term "about" is used herein refers to a degree of deviation. It means approximately, in the region of, roughly, or around. When the term "about" is used in conjunction with a numerical range, it modifies that range by extending the boundaries above and below the numerical values set forth. It is understood that support in this specification for numerical values used in connection with the term "about" is also provided for the exact numerical value itself as though "about" were not used.

Concentrations, amounts, and other numerical data may be expressed or presented herein in a range format. It is to be understood that such a range format is used merely for convenience and brevity and thus should be interpreted flexibly to include not only the numerical values explicitly recited as the limits or endpoints of the range, but also to include all the individual numerical values and/or sub-ranges encompassed within that range as if each numerical value (including fractions) and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 2.6, 3, 3.8, and 4 and sub-ranges such as from 1-3, from 2-4, and from 3-5, etc., as well as 1, 2, 3, 4, and 5, individually.

Formulation or compositional ingredients included or recited herein are to be presumed to be in wt % unless specifically stated otherwise. In addition, ingredient amounts presented in the form of ratios are to be presumed to be in wt % (e.g. % w/w) ratios. As such, a composition containing four ingredients at a 1:1:1:1 ratio would indicate that each ingredient is present in an amount of 25 wt %. Accordingly, in some aspects, the amount of an ingredient in a composition or formulation in terms of wt % can be derived from a numerical ratio value.

As used herein, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the composition's nature or characteristics would be permissible if present under the "consisting essentially of" language, even though not expressly recited in a list of items following such terminology. When using an open ended term in the specification, like "comprising" or "including," it is understood that direct support should be afforded also to "consisting essentially of" language as well as "consisting of" language as if stated explicitly and vice versa.

As used herein, "substantial" or "substantially" when used in reference to a quantity or amount of a material, or a specific characteristic thereof, refers to an amount that is sufficient to provide an effect that the material or characteristic was intended to provide. The exact degree of deviation allowable may in some cases depend on the specific context. Similarly, "substantially free of" or the like refers to the lack of an identified element or agent in a composition. Particularly, elements that are identified as being "substantially free of" are either completely absent from the composition, or are included only in amounts which are small enough so as to have no measurable effect on the composition.

As used herein, "active agent," "active agent," and the like refer to a molecule, compound, mixture, or ingredient that has a measurable physiologic effect on a subject when administered thereto in an appreciable amount, such as an effective, or therapeutically effective amount. Like terms such as "active fraction," "active component," and "active constituent" can be used interchangeable therewith. When the activity of an "active agent" exerts or otherwise results in a therapeutic effect of benefit in a subject to which the agent has been administered, the "active agent" can be referred to as a "therapeutic agent".

"Bergamot" refers to bergamot orange (*Citrus bergamia* Risso). This citrus species, grows abundantly in the Calabria region of southern Italy, and has been used in Calabrian folk medicine to treat cardiovascular ailments for centuries. Bergamot comprises two 3-hydroxymethylglutaryl (HMG) derivatives of naturally occurring flavonoid glycosides brutieridin and melitidin. These glycosides are the HMG derivatives of glucosylated hesperetin and naringenin, respectively, and have a structural similarity to the commercially available HMG-CoA reductase inhibitors known as the statins. As used herein bergamot can be used interchangeably to refer to the fruit and/or the extract.

As used herein a "concentrate" refers to dried powder derived from a component that does not include the use of any solvents during the concentration process.

The term "dosage unit" is understood to mean a unitary, i.e. a single dose which is capable of being administered to a subject or patient, and that may be readily handled and packed, remaining as a physically and chemically stable unit dose comprising either the active ingredient as such or a mixture of it with solid or liquid pharmaceutical vehicle materials. Dosages can be oral, nasal, enteral, parenteral, transdermal, transmucosal, etc.

The term "extract" refers to those substances prepared using a solvent, e.g., ethanol, water, steam, superheated water, methanol, hexane, chloroform liquid, liquid $CO_2$, liquid $N_2$, propane, supercritical $CO_2$ or any combination thereof. Extracts, as used herein, can refer to an extract in a liquid form, or can refer to a product obtained from further processing of the liquid form, such as a dried powder or other solid form. Extracts may take many forms including but not limited to: solid, liquid, particulate, chopped, distillate, etc. and may be performed by any number of procedures or protocols, such as chopping, grinding, pulverizing, boiling, steaming, soaking, steeping, infusing, applying a gas, etc., and may employ any suitable reagents, such as water, alcohol, steam, or other organic materials. Extracts typically have a given purity percentage and can be relatively to highly pure. In some embodiments, extracts can be phytoextracts made from specific parts of a source, such as the skin, pulp, leaves, flowers, fruits of a plant etc., or can be made from the whole source. In some aspects an extract may include one or more active fractions or active agents. In some extracts, maltodextrin can be added as a carrier. In some aspects, the purity of an extract can be controlled by, or be a function of the extraction process or protocol.

As used herein, "formulation" and "composition" can be used interchangeably and refer to a combination of at least two ingredients. In some embodiments, at least one ingredient may be an active agent or otherwise have properties that exert physiologic activity when administered to a subject.

As used herein, "increased or decreased concentration, secretion or biosynthesis," means an appreciable increase or decrease in amount (e.g. by at least 3%), concentration, rate of secretion or amount of biosynthesis of the referent compound.

As used herein, "linear inhibitory effect" or "dose-response" refers to a linear decrease in secretion or biosynthesis resulting from all concentrations of the inhibiting material over a dose-response curve. For example, inhibition at low concentrations followed by a failure of inhibition or increased secretion at higher concentrations represents a lack of a linear inhibitory effect.

As used herein, "Leaky Gut Syndrome (LGS)" is an increase in permeability of the intestinal mucosa to luminal macromolecules, antigens and toxins associated with inflammatory degenerative and/or atrophic mucosal damage. LGS can lead to any number of seemingly unrelated symptoms affecting every organ system in the body. LGS has also been linked with having a causative role in a large number of distinct illnesses. Many of these are autoimmune diseases, which means the immune system attacks the body's own cells. LGS plays a role in these types of illness because it increases immune reactions to food particles and then cross reactivity may occur meaning that the immune system attacks body tissues that are chemically similar to the foods to which it has become sensitized. A sampling of the many diseases in which leaky gut syndrome may have a role includes: rheumatoid arthritis, osteoarthritis, asthma, multiple sclerosis, vasculitis, Crohn's Disease, colitis, Addison's disease, lupus, thyroiditis, chronic fatigue syndrome, and fibromyalgia.

As used herein, "pharmaceutically acceptable" refers generally to materials which are suitable for administration to a subject in connection with an active agent or ingredient. For example, a "pharmaceutically acceptable carrier" can be any substance or material that can be suitably combined with an active agent to provide a composition or formulation suitable for administration to a subject. Excipients, diluents, and other ingredients used in or used to prepare a formulation or composition for administration to a subject can be used with such term.

As used herein the term "primary therapeutic agent" designates the presence of a therapeutic agent in a composition at an amount greater than the total combined amount of the extracts providing a synergistic effect in the composition.

The term "prevent" and its variants refer to prophylaxis against a particular undesirable physiological condition. The prophylaxis may be partial or complete. Partial prophylaxis may result in the delayed onset of a physiological condition. The person skilled in the art will recognize the desirability of delaying onset of a physiological condition, and will know to administer the compositions of the invention to subjects who are at risk for certain physiological conditions in order to delay the onset of those conditions. For example, the person skilled in the art will recognize that obese subjects are at elevated risk for coronary artery disease. Thus, the person skilled in the art can administer compositions to increase insulin sensitivity in an obese subject, whereby the onset of diabetes mellitus or dyslipemia may be prevented entirely or delayed.

As used herein, "oxidative stress" refers to an imbalance between the manifestations of reactive oxygen species (ROS) and a biological system's ability to readily detoxify the reactive intermediates. ROS result in the formation of free radicals. Free radicals (e.g. hydroxyl, nitric acid, superoxide) or the non-radicals (e.g. hydrogen peroxide, lipid peroxide) lead to damage (called oxidative damage) specific molecules with consequential injury to cells or tissue. Disturbances in the normal redox state of cells can cause toxic effects through the production of peroxides and free radicals that damage all components of the cell, including proteins, lipids, and DNA. While short term oxidative stress can be beneficial; over time oxidative stress can be involved in the etiology of many conditions and diseases. Increased production of ROS occurs as a result of fungal or viral infection, inflammation, aging, U.V. radiation, pollution, excessive alcohol consumption, cigarette smoking, etc. Removal or neutralization of ROS is achieved with antioxidants, endogenous (e.g. catalase, glutathione, superoxide dismutase) or exogenous (e.g. vitamins A, C, E, bioflavonoids, carotenoids).

As used herein "oxidative stress-associated pathologies" defines any condition that increases the cellular oxidation state to produce an oxidative stress response preceding a disease state. This generally results from increasing the production of reactive oxygen or reactive nitrogen species (ROS and RNS, respectively) (superoxide, hydrogen peroxide, hydroxyl radical, peroxynitrite, singlet oxygen) relative to cellular antioxidant defenses (antioxidants, antioxidant enzymes). Although an oxidative stress response does not necessarily result in disease, it is a critical component in the mechanism of many diseases. A non-limiting example of such disease includes metabolic syndrome, obesity, atherosclerosis, arterial hypertension, diabetes (types 1, 2 and 3), diminished exercise capacity, premature ejaculation, congestive cardiac failure, cardiovascular disease including cardiac arrest and myocardial infarction, motor dysfunctions, cataracts, cognitive disorders including Alzheimer's disease, Raynaud's phenomenon, essential hypertension, stroke, asthma, multiple sclerosis, vasculitis, Fragile X syndrome pancreatitis, various forms of inflammation including osteoarthritis, rheumatoid arthritis, inflammatory bowel disease, colitis, leaky gut syndrome, renal diseases and hemodialysis, shock, trauma, ischemia, Parkinson's disease, drug reactions, Crohn's disease, Addison's Disease, lupus, thyroiditis, chronic fatigue syndrome, fibromyalgia, many cancers including prostate and breast cancers, enhanced cancer chemotherapy, diseases associated with skin such as slow wound healing, wrinkles, and premature signs of aging.

As used herein the term "secondary therapeutic agent" designates the presence of a therapeutic agent in a composition at an amount less than the total combined amount of the extracts providing a synergistic effect in the composition.

The term, "subject," "subjects," or "subjects in need thereof" include humans as well as non-human subjects, particularly domesticated and farm animals. It will be understood that the subject to which a compound of the invention is administered need not suffer from a specific traumatic state. Indeed, the compounds of the invention may be administered prophylactically, prior to any development of symptoms. The term "therapeutic," "therapeutically," and the like are used to encompass therapeutic, palliative as well as prophylactic uses.

As used herein, the term "solvent" refers to a liquid or gaseous, aqueous or organic nature possessing the necessary characteristics to extract solid material from a plant product. Examples of solvents would include, but not limited to, water, steam, superheated water, methanol, ethanol, ethyl acetate, hexane, chloroform, liquid $CO_2$, liquid $N_2$, propane, or any combinations of such materials.

As used herein, "synergistic" means more than the additive effect of the individual components against a mechanism of action. For example if F1 produces response X, F2 produces response Y, then the combination of F1+F2>X+Y. In some situations F2 produces no response and the value for Y is equal to zero.

The phrase "effective amount," "therapeutically effective amount," or "therapeutically effective rate(s)" of an active ingredient refers to a non-toxic, but sufficient amount or delivery rates of the active ingredient, to achieve therapeutic results in treating a disease or condition for which the ingredient is being delivered. It is understood that various biological factors may affect the ability of a substance to perform its intended task. Therefore, an "effective amount," "therapeutically effective amount," or "therapeutically effective rate(s)" may be dependent in some instances on such biological factors. Further, while the achievement of therapeutic effects may be measured by a physician or other qualified medical personnel using evaluations known in the art, it is recognized that individual variation and response to treatments may make the achievement of therapeutic effects a subjective decision. The determination of a therapeutically effective amount or delivery rate is well within the ordinary skill in the art of pharmaceutical sciences and medicine.

The terms "treat," "treating," or "treatment" as used herein and as well understood in the art, mean an approach for obtaining beneficial or desired results, including without limitation clinical results in a subject being treated. Beneficial or desired results can include, but are not limited to, alleviation or amelioration of one or more signs or symptoms of a condition, diminishment of extent of disease, stabilizing (i.e. not worsening) the state of a disease or condition, delaying or slowing of disease progression, amelioration or palliation of the disease state, diminishment of the reoccurrence of disease, and remission (whether partial or total), whether detectable or undetectable. For example, where the physiological state is poor glucose tolerance, "treatment" refers to improving the glucose tolerance of a treated subject. As another example, where the physiological state is obesity, the term "treatment" refers to reducing the body fat mass, improving the body mass or improving the body fat ratio of a subject. Treatment of diabetes means improvement of blood glucose control. Treatment of inflammatory diseases means reducing the inflammatory response either systemically or locally within the body. "Treat," "treating," and "treatment" can also mean prolonging survival as compared to expected survival if not receiving treatment and can be prophylactic. Such prophylactic treatment can also be referred to as prevention or prophylaxis of a disease or condition. The prophylaxis may be partial or complete. Partial prophylaxis may result in the delayed onset of a physiological condition. The person skilled in the art will recognize that treatment may, but need not always, include remission or cure.

As used herein, "compounds" may be identified either by their chemical structure, chemical name, or common name. When the chemical structure, chemical name, or common name conflict, the chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated or identified compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures encompass all possible tautomeric forms of the illustrated or identified compounds. The compounds described also encompass isotopically labeled compounds where one or more atoms have an atomic mass different from the atomic mass conventionally found in nature. Examples of isotopes that may be incorporated into the compounds of the invention include, but are not limited to, $^2H$, $^3H$, $^{13}C$, $^{14}C$, $^{15}N$, $^{18}O$, $^{17}O$, etc. Compounds may exist in un-solvated forms as well as solvated forms, including hydrated forms and as N-oxides. In general, compounds may be hydrated, solvated or N-oxides. Certain compounds may exist in multiple crystalline or amorphous forms. Also contemplated are congeners, analogs, hydrolysis products, metabolites and precursor or prodrugs of the compound. In general, all physical forms are equivalent for the uses contemplated herein and are intended to be within the scope of the present disclosure.

Comparative terms such as "more effectively," "greater than," "improved," "enhanced," and like terms can be used to state a result achieved or property present in a formulation or process that has a measurably better or more positive outcome than the thing to which comparison is made. In some instances comparison may be made to the prior art.

Reference is made hereinafter in detail to specific embodiments of the invention. While the invention will be described in conjunction with these specific embodiments, it will be understood that it is not intended to limit the invention to such specific embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail, in order not to unnecessarily obscure the present invention.

All forms of life maintain a reducing environment within their cells. This reducing environment is preserved by enzymes that maintain the reduced state through a constant input of metabolic energy. Disturbances in this normal redox state can cause toxic effects through the production of peroxides and free radicals that damage all components of the cell, including proteins, lipids and DNA.

In humans, oxidative stress is involved in the etiology of many diseases. For example, oxidative stress is implicated in metabolic syndrome, obesity, atherosclerosis, arterial hypertension, diabetes (types I, II, and III), diminished exercise capacity, premature ejaculation, congestive cardiac failure, cardiovascular disease including cardiac arrest and myocardial infarction, motor dysfunctions, cataracts, cognitive disorders including Alzheimer's disease, Raynaud's phenomenon, essential hypertension, stroke, asthma, multiple sclerosis, vasculitis, Fragile X syndrome pancreatitis, various forms of inflammation including osteoarthritis, rheumatoid arthritis, inflammatory bowel disease, colitis, leaky gut syndrome, renal diseases and hemodialysis, shock, trauma, ischemia, Parkinson's disease, drug reactions, Crohn's disease, Addison's Disease, lupus, thyroiditis, chronic fatigue syndrome, fibromyalgia, many cancers including prostate and breast cancers, enhanced cancer chemotherapy, diseases associated with skin such as slow wound healing, wrinkles, premature signs of aging, as well as others.

Reactive oxygen species (ROS), reactive nitrogen species (RNS), other free radicals, and oxidant sources (collectively i.e. $O_2^-$, $1O_2$, $HO^-$, $NO^-$, $ONOO^-$, $HOCl$, $RO(O)^-$, $O(O)^-$), can cause severe damage to cells of the body. For example, this damage can be to the DNA, proteins, and other macromolecules and forms the basis for a wide variety of inflammation-based diseases.

Experimental evidence directly or indirectly suggests that there are six major reactive oxygen species that cause oxidative damage in the human body. These species include superoxide anion (O), hydrogen peroxide ($H_2O_2$), peroxyl radicals ($ROO^-$), hydroxyl radical ($HO^-$), singlet oxygen ($1O_2$), and peroxynitrite ($ONOO^-$). In order to combat this damage, antioxidants inhibit the oxidation and prevent the formation of free radicals. Within biological systems, there are at least four general sources of antioxidants: (1) enzymes, (i.e. superoxide dismutase, glutathione peroxidase, and catalase); (2) large molecules (i.e. albumin, ceruloplasmin, ferritin, other proteins); (3) small molecules, (ascorbic acid, glutathione, uric acid, tocopherol, carotenoids, (poly) phenols); and (4) some hormones (estrogen, angiotensin, melatonin, etc.).

Oxidants and antioxidants can have different chemical and physical characteristics. Individual antioxidants can act by multiple mechanisms in a single system or by a different single mechanism and can respond in a different manner to different radicals or oxidant sources. For example, carotenoids are not particularly good quenchers of peroxyl radicals relative to phenolics and other antioxidants; however, carotenoids are exceptional in quenching singlet oxygen, at which most other phenolics and antioxidants are relatively ineffective. Singlet oxygen is not a radical and does not react via radical mechanisms but reacts mostly by the addition to double bonds, forming endo-peroxides that can be reduced to alkoxyl radicals that initiate radical chain reactions. Due to the multiple reaction characteristics and mechanisms as well as different phase localizations are usually involved, no single assay will accurately reflect all of the radical sources or all antioxidants in a mixed or complex system.

Living cells have a biological defense system composed of enzymatic antioxidants that convert ROS/RNS to harmless species. For example, $H_2O_2$ can be converted to water and oxygen by catalase. In another example, $O^-$ is converted to oxygen and hydrogen peroxide by superoxide dismutase (SOD) or reacts with nitric oxide ($NO^-$) to form peroxynitrite. When nitric oxide and superoxide are both present, they may also react with nitrogen dioxide to form $N_2O_3$ and peroxynitrate (See FIG. 1). Peroxynitrate decomposes to give nitrite and oxygen, while $N_2O_3$ can react with thiols to give nitrosothiols or with hydroxide anion to give nitrite. Peroxynitrate also reacts at a diffusion-limited rate with peroxynitrite to yield two molecules of nitrogen dioxide and one of nitrite. This creates a cycle to generate more nitrogen dioxide when bolus additions of peroxynitrite are added at neutral pH and substantially increases the number of potential reactions occurring. These same reactions will also occur in vivo, particularly when nitric oxide is produced faster than superoxide.

Figure 2:
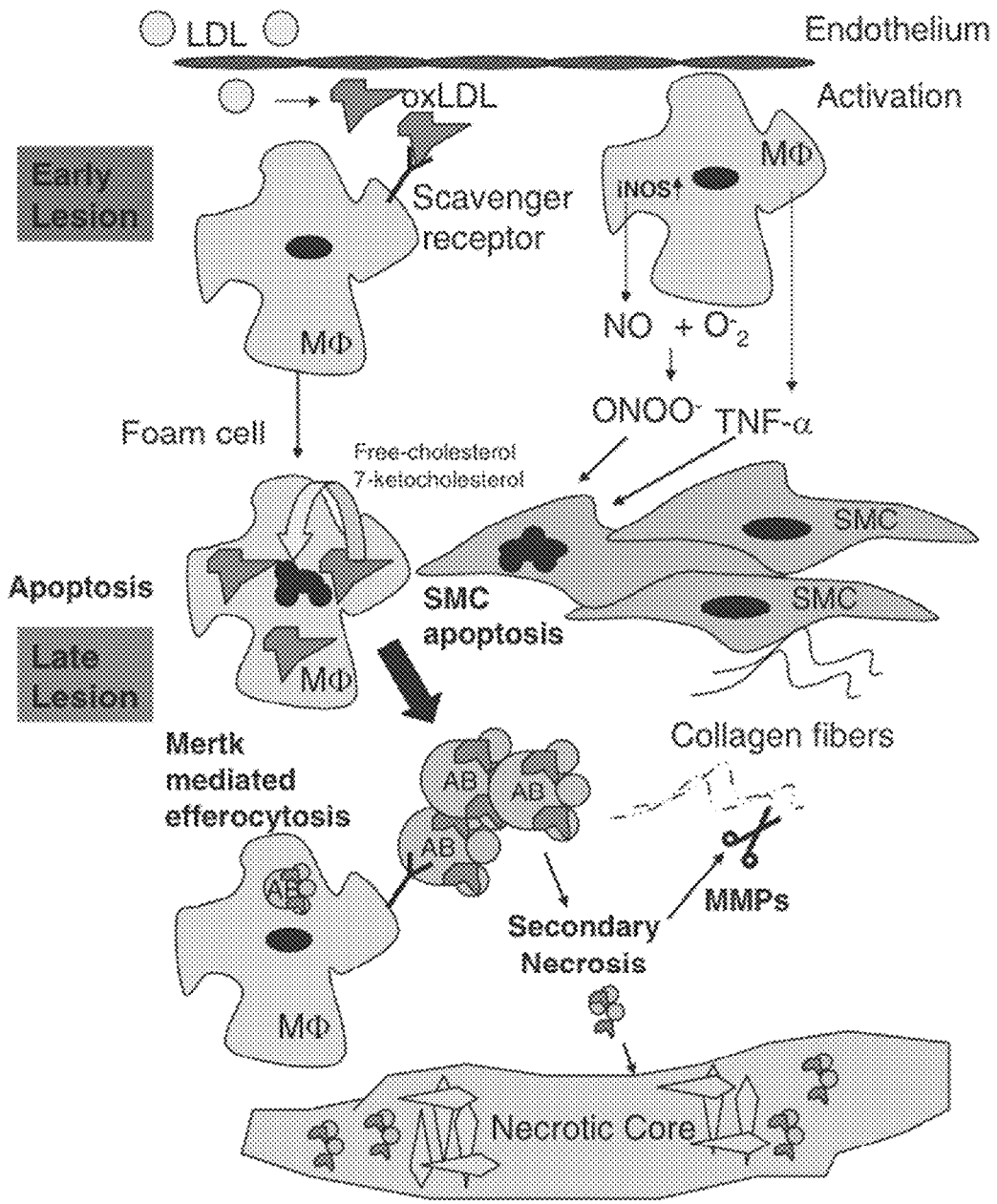
FIG. 2 schematically displays the roles played by macrophage (M) during early lesion development within an atherosclerotic plaques of the vascular endothelium.

Peroxynitrite can also be naturally produced by alveolar macrophages (See FIG. 2). When alveolar macrophages are stimulated to produce both superoxide and nitric oxide, peroxynitrite is quantitatively produced as evidenced by the amount of nitric oxide and superoxide produced and the amount of oxygen consumed. Extracellular addition of superoxide dismutase (SOD) in high concentrations does not significantly reduce the amount of peroxynitrite formed and instead serves as a catalyst of tyrosine nitration. This suggests that superoxide produced at the membrane surface and nitric oxide diffusing through the membrane react at the membrane interface so quickly that SOD in the bulk phase cannot compete.

Nitric oxide (NO) and peroxynitrite play significant roles in cardiovascular pathophysiology. NO can activate the soluble guanylate cyclase (sGC)-cGMP signal transduction pathway which mediates various physiological/beneficial effects in the cardiovascular system including vasodilatation, inhibition of platelet aggregation, anti-inflammatory, anti-remodeling, and anti-apoptotic effects. Under pathological conditions associated with increased oxidative stress and inflammation (myocardial infarction, ischemic heart disease, myocarditis, cardiomyopathy, hypertension, etc.), NO and superoxide (02) react to form peroxynitrite ($ONOO^-$) which induces cell damage via lipid peroxidation, inactivation of enzymes and other proteins by oxidation and nitration, and also activation of stress signaling, matrix metalloproteinases (MMPs) among others.

Peroxynitrite also triggers the release of proapoptotic factors such as cytochrome c and apoptosis-inducing factor (AIF) from the mitochondria, which mediate caspase-dependent and -independent apoptotic death pathways. Moreover, peroxynitrite, in concert with other oxidants, causes stand breaks in DNA, activating the nuclear enzyme poly (ADP-ribose) polymerase-1 (PARP-1). Mild damage of DNA activates the DNA repair machinery. In contrast, once excessive oxidative and nitrosative stress-induced DNA damage occurs, like in various forms of myocardial reperfusion injury and heart failure, over activated PARP initiates an energy-consuming cycle by transferring ADP-ribose units from nicotinamide adenine dinucleotide (NAD+) to nuclear proteins, resulting in rapid depletion of the intracellular $NAD^+$ and ATP pools, slowing the rate of glycolysis and mitochondrial respiration, eventually leading to cellular dysfunction and death. Poly(ADP-ribose) glycohydrolase (PARG) degrades poly(ADP-ribose) (PAR) polymers, generating free PAR polymer and ADP-ribose. Over activated PARP also facilitates the expression of a variety of inflammatory genes leading to increased inflammation and associated oxidative stress, thus facilitating the progression of cardiovascular dysfunction and heart.

Peroxynitrite also functions to amplify the inflammatory signaling in chronic inflammatory conditions. Moreover, inflammation is triggered by the activation of multiple signaling cascades culminating in the up regulated production of an array of pro-inflammatory cytokines and chemokines. Those initiate a more complex inflammatory reaction characterized by the activation of inflammatory cells and the stimulated activity of enzymes, including inducible NO synthase (iNOS), which produces high amounts of NO, and the superoxide ($O_2^-$) producing enzymes NADPH oxidase (NADPHox) and xanthine oxidase (XO). The simultaneous production of NO and $O_2^-$ results in the generation of peroxynitrite ($ONOO^-$), which in turn damages target molecules including proteins, glutathione (GSH), mitochondria, and DNA. DNA damage can initiate apoptotic cell death and is also the obligatory trigger for the activation of poly(ADP-ribose) polymerase (PARP), which may induce cell necrosis by ATP depletion. Both $ONOO^-$ and PARP further participate to the up regulation of pro-inflammatory signal transduction pathways, thereby producing a self-amplifying cycle of inflammatory cell injury.

Figure 3:
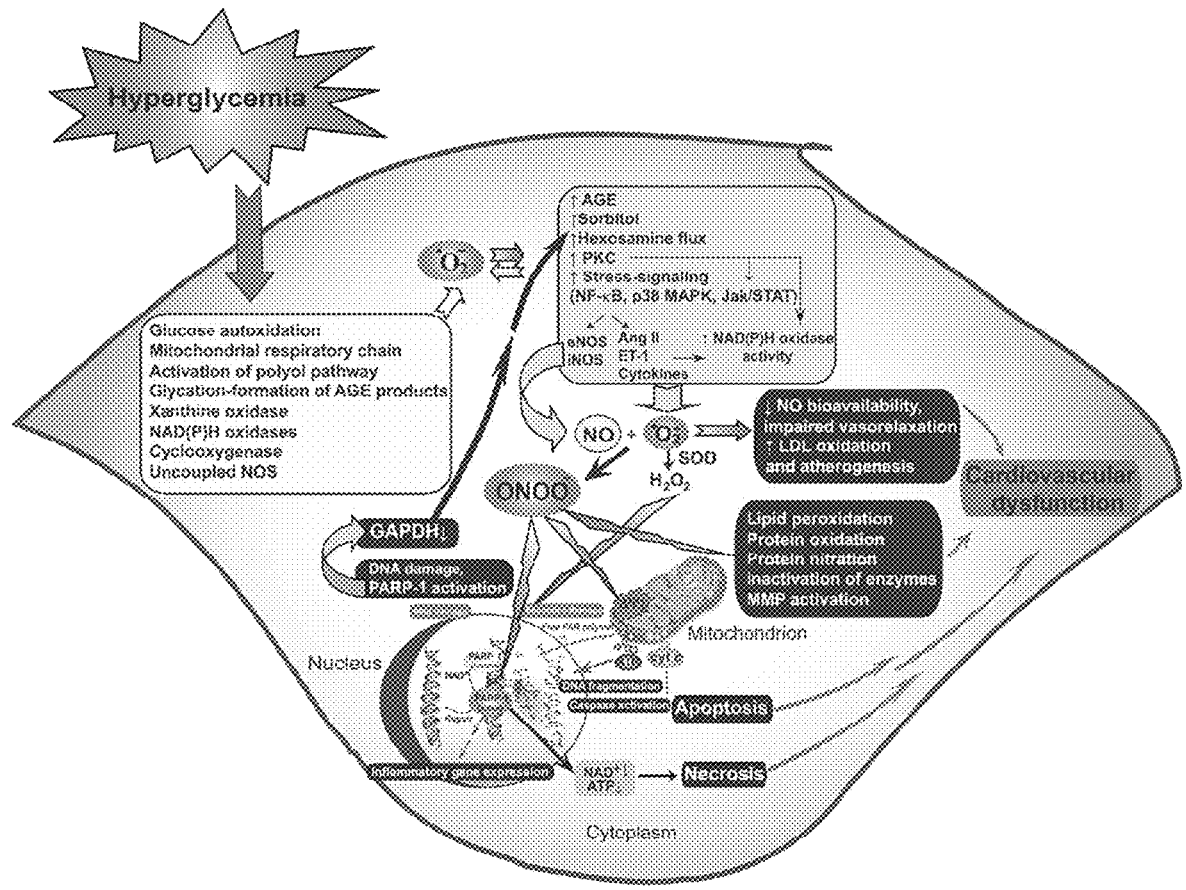
FIG. 3 schematically displays the mechanisms of cardiovascular dysfunction in diabetes illustrating the role of superoxide, peroxynitrite and specific kinase signalling cascades.

Superoxide and peroxynitrite also coordinate cardiovascular dysfunction in diabetes (See FIG. 3). Hyperglycemia induces increased superoxide anion ($O_2^-$) production via activation of multiple pathways including xanthine and NAD(P)H oxidases, cyclooxygenase, uncoupled nitric oxide synthase (NOS), glucose autoxidation, mitochondrial respiratory chain, polyol pathway, and formation of advanced glycation end products (AGE). Superoxide activates AGE, protein kinase C (PKC), polyol (sorbitol), hexosamine, and stress-signaling pathways leading to increased expression of inflammatory cytokines, angiotensin II (Ang II), endothelin-1 (ET-1), and NAD(P)H oxidases, which in turn generate more superoxide via multiple mechanisms. Hyperglycemia-induced increased superoxide generation may also favor an increased expression of nitric oxide synthases (NOS) through the activation of NFκB, which may increase the generation of nitric oxide (NO). Superoxide anion may quench NO, thereby reducing the efficacy of a potent endothelium-derived vasodilator system. Superoxide can also be converted to hydrogen peroxide ($H_2O_2$) by superoxide dismutase (SOD) and interact with NO to form a reactive oxidant peroxynitrite ($ONOO^-$), which induces cell damage via lipid peroxidation, inactivation of enzymes and other proteins by oxidation and nitration, and activation of matrix metalloproteinases (MMPs) among others.

Peroxynitrite can also act on mitochondria [decreasing the membrane potential (Ψ)], triggering the release of proapoptotic factors such as cytochrome c (Cyt c) and apoptosis-inducing factor (AIF). These factors mediate caspase-dependent and caspase-independent apoptotic death pathways.

Peroxynitrite, in concert with other oxidants (e.g., $H_2O_2$), can cause strand breaks in DNA, activating the nuclear enzyme poly(ADP-ribose) polymerase-1 (PARP-1). Mild damage to DNA activates the DNA repair machinery. Once excessive oxidative and nitrosative stress-induced DNA damage occurs, overactivated PARP-1 initiates an energy-consuming cycle by transferring ADP-ribose units (small red spheres) from $NAD^+$ to nuclear proteins, resulting in rapid depletion of the intracellular $NAD^+$ and ATP pools, slowing the rate of glycolysis and mitochondrial respiration, and eventually leading to cellular dysfunction and death. Poly (ADP-ribose) glycohydrolase (PARG) degrades poly(ADP-ribose) (PAR) polymers, generating free PAR polymer and ADP-ribose, which may signal to the mitochondria to induce AIF release. PARP-1 activation also leads to the inhibition of cellular glyceraldehyde-3-phosphate dehydrogenase (GAPDH) activity, which in turn favors the activation of PKC, AGE, and hexosamine pathway leading to increased superoxide generation. PARP-1 also regulates the expression of a variety of inflammatory mediators, which might facilitate the progression of diabetic cardiovascular complications.

Additional conditions in which the reaction products of peroxynitrite have been detected and in which pharmacological inhibition of its formation or its decomposition have been shown to be of benefit include vascular diseases, ischaemia-reperfusion injury, circulatory shock, pain and neurodegeneration.

No enzymatic action is presently known that scavenges $ROO^-$, $HO^-$, $1O_2$, and $ONOO^-$. Therefore, the burden of defense relies on a variety of non-enzymatic antioxidants such as vitamins C and E and many phytochemicals that have the property of scavenging oxidants and free radicals. To comprehensively evaluate the oxidant-scavenging capacity of a food sample, assays have to be designed to include these ROS (i.e. ORAC (Oxygen Radical Absorbance Capacity) Assay).

At the cellular level, signal transduction refers to the movement of a signal or signaling moiety from outside of the cell to the cell interior. The signal, upon reaching its receptor target, may initiate ligand-receptor interactions requisite to many cellular events, some of which may further act as a subsequent signal. Such interactions serve to not only as a series cascade but moreover an intricate interacting network or web of signal events capable of providing fine-tuned control of homeostatic processes. This network however can become dysregulated, thereby resulting in an alteration in cellular activity and changes in the program of genes expressed within the responding cell.

Signal transducing receptors are generally classified into three classes. The first class of receptors are receptors that penetrate the plasma membrane and have some intrinsic enzymatic activity. Representative receptors that have intrinsic enzymatic activity include: tyrosine kinases (e.g. PDGF, insulin, EGF and FGF receptors), tyrosine phosphatases (e.g. CD45 [cluster determinant-45] protein of T cells and macrophages), guanylate cyclases (e.g. natriuretic peptide receptors) and serine/threonine kinases (e.g. activin and TGF-β receptors). Receptors with intrinsic tyrosine kinase activity are capable of autophosphorylation as well as phosphorylation of other substrates.

Receptors of the second class are those that are coupled, inside the cell, to GTP-binding and hydrolyzing proteins (termed G-proteins). Receptors of this class that interact with G-proteins have a structure that is characterized by seven trans-membrane spanning domains. These receptors are termed serpentine receptors. Examples of this class are the adrenergic receptors, odorant receptors, and certain hormone receptors (e.g. glucagon, angiotensin, vasopressin and bradykinin).

The third class of receptors may be described as receptors that are found intracellularly and upon ligand binding, migrate to the nucleus where the ligand-receptor complex directly affects gene transcription.

The proteins which encode for receptor tyrosine kinases (RTK) contain four major domains, those being: a) a trans-membrane domain, b) an extracellular ligand binding domain, c) an intracellular regulatory domain, and d) an intracellular tyrosine kinase domain. The amino acid sequences of RTKs are highly conserved with those of cAMP-dependent protein kinase (within the ATP and substrate binding regions). RTK proteins are classified into families based upon structural features in their extracellular portions which include the cysteine rich domains, immunoglobulin-like domains, cadherin domains, leucine-rich domains, Kringle domains, acidic domains, fibronectin type III repeats, discoidin I-like domains, and EGF-like domains. Based upon the presence of these various extracellular domains the RTKs have been sub-divided into at least 14 different families.

Many receptors have intrinsic tyrosine kinase activity upon phosphorylation and can interact with other proteins of the signaling cascade. These other proteins contain a domain of amino acid sequences that are homologous to a domain first identified in the c-Src proto-oncogene; these domains are termed SH2 domains. The interactions of SH2 domain containing proteins with RTKs or receptor associated tyrosine kinases leads to tyrosine phosphorylation of the SH2 containing proteins. The resultant phosphorylation produces an alteration (either positively or negatively) in that activity. Several SH2 containing proteins that have intrinsic enzymatic activity include phospholipase C-γ (PLC-γ), the proto-oncogene c-Ras associated GTPase activating protein (rasGAP), phosphatidylinositol-3-kinase (PI-3K), protein tyrosine phosphatase-1C (PTP1C), as well as members of the Src family of protein tyrosine kinases (PTKs).

Non-receptor protein tyrosine kinases (PTK) by and large couple to cellular receptors that lack enzymatic activity themselves. An example of receptor-signaling through protein interaction involves the insulin receptor (IR). This receptor has intrinsic tyrosine kinase activity but does not directly interact, following autophosphorylation, with enzymatically active proteins containing SH2 domains (e.g. PI-3K or PLC-γ). Instead, the principal IR substrate is a protein termed IRS-1.

The receptors for the TGF-β superfamily represent the prototypical receptor serine/threonine kinase (RSTK). Multifunctional proteins of the TGF-β superfamily include the activins, inhibins and the bone morphogenetic proteins (BMPs). These proteins can induce and/or inhibit cellular proliferation or differentiation and regulate migration and adhesion of various cell types. One major effect of TGF-β is a regulation of progression through the cell cycle. Additionally, one nuclear protein involved in the responses of cells to TGF-β is c-Myc, which directly affects the expression of genes harboring Myc-binding elements. PKA, PKC, and MAP kinases represent three major classes of non-receptor serine/threonine kinases.

There can be a relationship between kinase activity and disease states. Such relationships can be either causative of the disease itself or intimately related to the expression and progression of disease-associated symptomology and pathology. For example, kinase activity is thought to be implicated in cognitive disorders, including Alzheimer's disease, congestive cardiac failure, pulmonary hypertension, cardiomyopathies, motor dysfunction, Raynaud's phenomenon, essential hypertension, stroke, asthma, multiple sclerosis, vasculitis, various forms of inflammation including osteoarthritis, rheumatoid arthritis, type I and type II diabetes, metabolic syndrome, obesity, inflammatory bowel disease, Crohn's disease, Addison's Disease, lupus, thyroiditis, chronic fatigue syndrome, and fibromyalgia among others.

Autoimmune diseases result from a dysfunction of the immune system in which the body produces auto-antibodies that attack its own organs, tissues and cells—a process mediated via protein phosphorylation. Over 80 clinically distinct autoimmune diseases have been identified and collectively afflict approximately 24 million people in the U.S. Autoimmune diseases can affect any tissue or organ of the body. Because of this variability, they can cause a wide range of symptoms and organ injuries, depending upon the site of autoimmune attack. Although treatments exist for many autoimmune diseases, there are no definitive cures for any of them. Treatments to reduce the severity often have adverse side effects.

The etiology and pathogenesis of autoimmune diseases in humans is still poorly understood, but is viewed to progress in three phases, an initation phase, an effector phase, and an activation phase. In the initiation phase, dendritic cells present self-antigens to autoreactive T cells. The T cells activate autoreactive B cells via cytokines resulting in the production of autoantibodies, which in turn form immune complexes in joints. In the effector phase, the immune complexes bind Fcf receptors on macrophages and mast cells, resulting in release of cytokines and chemokines, inflammation and pain. In the activation phase, the final phase, cytokines and chemokines activate and recruit synovial fibroblasts, osteoclasts and polymorphonuclear neutrophils that release proteases, acids, and ROS such as $O_2^-$, resulting in irreversible cartilage and bone destruction. B cell activation signals through spleen tyrosine kinase (Syk) and phosphoinositide 3-kinase (PI3K) following antigen receptor triggering. After the engagement of antigen receptors on B cells, Syk is phosphorylated on three tyrosines. Syk is a 72-kDa protein-tyrosine kinase that plays a central role in coupling immune recognition receptors to multiple downstream signaling pathways. This function is a property of both its catalytic activity and its ability to participate in interactions with effector proteins containing SH2 domains. Phosphorylation of Tyr-317, -342, and -346 create docking sites for multiple SH2 domain containing proteins. Association of the 72-kDa protein-tyrosine kinase Ptk72 with the B-cell antigen receptor. In one invention aspect, there is provided a safe, long-term treatment approach for pain relief in these patients suffering from autoimmune disorders. Since inducers of COX-2 and iNOS synthesis signal through the Syk, PI3K, p38, ERK1/2, and NF-kB dependent pathways, inhibitors of these pathways may be therapeutic in autoimmune conditions and in particular in the inflamed and degenerating joints of rheumatoid arthritis (RA) or osteoarthritis (OA) patients.

Syk has been shown to be required for the activation of PI3K in response to a variety of signals including engagement of the B cell antigen receptor (BCR) and macrophage or neutrophil Fc receptors. In B cells, the BCR-stimulated activation of PI3K can be accomplished through the phosphorylation of adaptor proteins such as BCAP, CD19, or Gab 1, which creates binding sites for the p85 regulatory subunit of PI3K. Signals transmitted by many IgG receptors require the activities of both Syk and PI3K and their recruitment to the site of the clustered receptor. In neutrophils and monocytes, a direct association of PI3K with phosphorylated immuno-receptor tyrosine based activation motif sequences on FcgRIIA was proposed as a mechanism for the recruitment of PI3K to the receptor. A direct molecular interaction between Syk and PI3K has been reported.

The cdc-like kinase CLK1 is involved in cell proliferation as a dual-specificity kinase acting on both serine/threonine and tyrosine-containing substrates; it phosphorylates serine- and arginine-rich proteins of the spliceosomal complex and may be a constituent of a network of regulatory mechanisms that enable SR proteins to control RNA splicing. The Clks also regulate the alternative splicing of microtubule-associated protein tau and are implicated in frontotemporal dementia and Parkinson's disease through the phosphorylation of splicing factors. Inhibitors of Clk isoforms may alter these events and could prove to be useful agents in disease phenotypes characterized by abnormal splicing.

The signaling pathways identified for the insulin receptor (IR) include G-protein coupled receptor signaling pathways, activation of MAPK activity, activation of protein kinase B activity, carbohydrate metabolic process, cellular response to growth factor stimulus, exocrine pancreas development, glucose homeostasis, positive regulation of glucose import, positive regulation of glycogen biosynthetic process, and positive regulation of glycolysis.

Glycogen synthase kinase 3 (GSK3) was initially described as a key enzyme involved in glycogen metabolism, but is now known to regulate a diverse array of cell functions. Two forms of the enzyme, GSK-3a and GSK-3b, have been previously identified. Small molecules inhibitors of GSK-3 may, therefore, have several therapeutic uses, including the treatment of neurodegenerative diseases, diabetes type II, bipolar disorders, stroke, cancer, and chronic inflammatory disease. Glycogen synthase kinase 3 (GSK-3) inhibitors as new promising drugs for diabetes, neurodegeneration, cancer, and inflammation.

AMP-activated protein kinase (AMPK) plays a key role as a master regulator of cellular energy homeostasis. The kinase is activated in response to stresses that deplete cellular ATP supplies such as low glucose, hypoxia, ischemia, and heat shock. Due to its role as a central regulator of both lipid and glucose metabolism, AMPK is considered to be a potential therapeutic target for the treatment of type II diabetes mellitus, obesity, and cancer. AMPK has also been implicated in a number of species as a critical modulator of aging through its interactions with mTOR and sirtuins.

In one invention embodiment, there is presented oxidative stress modulating compositions and associated methods. An exemplary composition can comprise a combination of apple, grape, green tea, and olive extracts in amounts that provide a greater antioxidant activity than provided by an equivalent amount of any one extract or a sum of the extracts. In one example, the apple, grape, green tea, and olive extracts can comprise extracts formulated from the leaves, skin, rind, pulp, juice, seeds, or combinations of these raw materials.

In one example, the apple extract can comprise an extract derived from a member selected from the group consisting of *Malus domestica, Malus sieversii, Malus sylvestris, Malus pumila*, and combinations thereof. In one example the apple extract can be derived from the species *Malus pumila*. In one example the apple extract can be derived from a combination of *Malus domestica* and *Malus pumila*. In some embodiments the apple extract can comprise any or all parts of the apple, including but not limited to the skin, flesh/fruit (exocarp, mesocarp, and/or endocarp), seed, stalk, stem, leaf, or a combination thereof. In one example, the apple extract comprises the skin and fruit of the apple. In some embodiments, the extract can be derived from immature apples. In one embodiment, an extraction solvent can be ethanol.

In one example, the grape extract can comprise a member selected from the group consisting of *Vitis vinifera, Vitis labrusca, Vitis riparia, Vitis rotundifolia, Vitis rupestris, Vitis aestivalis, Vitis mustangensis*, and combinations thereof. In one example, the grape extract can be derived from *Vitis vinifera*. In some embodiments, the grape extract can comprise any or all parts of the grape including but not limited to the skin, flesh/fruit, seed, vascular bundles, vine, leaves, or combination thereof. In one embodiment, the grape extract can be derived from the seeds. In another embodiment, the grape extract can be derived from the skin. In yet another embodiment, the grape extract can be derived from the seeds and skin of the grape. In some embodiments, the grape extract comprises from about 75 wt % to about 95 wt % phenolics on a dry weight basis. In other embodiments, the grape extract can comprise from about 80 wt % to 97 wt % phenolics on a dry weight basis. In one example, the extraction solvent can be ethanol, water, or a mixture thereof.

In one example, the green tea extract can be derived from *Camellia sinensis*. In some embodiments, the green tea extract can comprise any or all parts of the tea including but not limited to the leaf, seed, stem, flower, or combination thereof. In one embodiment, the green tea extract can be derived from the leaves. In another example, the extract solvent can be water, ethanol, ethyl acetate, or combinations thereof.

In one example, the olive extract comprises a subspecies of *Olea europea* selected from the group consisting of the subspecies *europea, cuspidiata, guanchica, cerasiformis, maroccana, laperrinei, cerasiformis,* or a combination thereof. In some embodiments, the olive extract can comprise any or all parts of the olive including but not limited to the leaf, seed, pulp, fruit, stem, or combination thereof. In one embodiment, the olive extract can be derived from the leaves. In another example, the extraction solvent can be an ethanol and water solution.

In some embodiments, the plant or herb to extract ratio can range from about 1 to about 10. In other examples, the raw plant or herb to extract ratio can be from about 2 to about 5, from about 4 to about 7, or from about 8 to about 10. Moreover, the ratio of the extracts can be present in the formulation at any ratio to the other extracts that provides a greater antioxidant activity than provided by an equivalent amount of any one extract or a sum of the extracts. In one example, at least one of the extracts in the composition can be present in a different amount than the other extracts. In another example, the extracts can all be present in the composition at the same amount.

By way of example, in some embodiments, each extract can be present at a ratio of from about 1 to about 50 times the amount of another extract. This applies to each and every extract in the formulation, including those listed in the examples below. In one aspect, the apple extract can be present in the formulation at a ratio of from 1 to 50 times the amount of a grape, green tea, or olive extract. In another aspect, the apple extract can be present in the formulation at a ratio of from about 1 to 25 times the amount of a grape, green tea, or olive extract. In a further aspect, the apple extract in the formulation can be present at a ratio of from 1 to 10 times the amount of a grape, green tea, or olive extract. In an additional aspect, the apple extract can be present in at a ratio of from 1 to 5 times the amount of a grape, green tea, or olive extract. In yet another aspect, the apple extract can be present in the formulation at a ratio of 1 times the amount of a grape, green tea, or olive extract. Any specific numerical value within the numerical range is included. In fact, each of the apple, grape, green tea, and olive extracts may be present in a ratio of anywhere between 1 to 50 times and 1 times the amount of the other extracts. For example, the amount of apple extract to grape extract to green tea extract to olive extract may in some embodiments be 1-25:1-25:1-25:1-25 respectively. As such, any number given specific ratio that yields a synergistic effect as recited herein can be used, for example 25:1:1:1 or 1:25:1:1, or 1:1:25:1, 1:1:1:25. When considered in terms of wt %, this would equate to one ingredient being present in an amount of 89.28 wt % and the other three ingredients being present in amounts of 3.57 wt %. This can be considered either in terms of the formulation as a whole (when only these four ingredients are present), or in terms of the synergistic extract or enhancer portion of the formulation only. For example, in a formulation containing only these four extracts, at a 1:1:1:1 ratio the relative amount of each would be 25 wt % each (i.e. 100/4=25). However, in a formulation where the amount of apple, grape, green tea an olive extracts was only 20 wt % of the total formulation and the extracts of each were present in a 1:1:1:1 ratio respectively, it can be considered that each extract is present in the overall formulation in an amount of 5 wt % each (25×20×0.001=5 wt %).

As mentioned, any number of ratios of one extract to another that results in a synergistic effect (i.e. more than an equal amount of activity provided by any one extract, or more than the simple sum of the activity provided by the total extracts) can be used. For example, keeping in the order of the extracts listed above, in one embodiment, the ratios can be any number within the range of 1-50 for each extract, such as 1-10:1-10:1-10:1-10, which would include without limitation, 1:1:1:1, 1:2:1:2, 1:5:6:1, 10:1:5:2, 3:7:2:4, and 1:3:5:8 for example. Additionally, these ratios and ranges of ratios can be applied to not only the four ingredients of apple, grape, green tea, and olive extracts, but also to the other extracts listed in the examples below as PC 4.1, 4.2, 8, 9, or 10. In some embodiments, the extracts can all be present at a weight ratio of about 1:1:1:1. In other embodiments, the apple, grape, green tea, and olive extracts can be present at a weight ratio of about 6:1:3:1.

In some embodiments, the composition further comprises a primary or a secondary therapeutic agent. In one embodiment, the primary or secondary therapeutic agent can comprise a member selected from the group consisting of bergamot, mangosteen, berberine, arginine, citrulline, glutamine, zinc, beet, loclo, protein, curcumin, phytosterols, fish oil, CoQ10, vitamins, fiber, inulin, aminogen®, biotin, black bean powder, copper citrate, ferrous fumarate, fructose, garbanzo bean, gum arabic, magnesium oxide, manganese citrate, medium chain triglycerides, pea fiber, pea protein isolate, potassium citrate, vitamin B6, riboflavin, rice bran, rice protein, sodium citrate, sodium selenate, thiamin HCl, vitamin D2, vitamin E, zinc citrate, adzuki bean, D-calcium pantothenate, lycopene, polyphenols, ascorbic acid, β-glucans, lutein, blueberry, borage oil, broccoli flowers, carrot root, cranberry fruit, chromium nicotinate, cyanocobalamin, flax seed/*Linum usitatissimum*, folic acid, lo han extract, niacinamide, pomegranate fruit, vitamin A, carotentiods, vitamin E, phytosterols, lignin, CoQ10, glutathione, and combinations thereof.

In another embodiment, the primary or secondary therapeutic agent can comprise a member selected from the group consisting of bergamot, mangosteen, berberine, arginine, citrulline, glutamine, zinc, beet, loclo, protein, curcumin, phytosterols, fish oil, CoQ10, vitamins, fiber, inulin, and combinations thereof. In one embodiment, the primary or secondary therapeutic agent can be bergamot extract. In another example, the primary or secondary therapeutic agent can be mangosteen extract. The mangosteen extract can be a mangosteen fruit extract and/or mangosteen pericarp extract. In a further embodiment, the primary or secondary therapeutic agent can comprise a mangosteen pericarp extract and a bergamot extract. In yet another example, the primary or secondary therapeutic agent can comprise berberine. In another example, the primary or secondary therapeutic agent can comprise arginine and beet or citrulline and beet. In a further embodiment, the primary or secondary therapeutic agent can comprise phytosterols. In another embodiment, the primary or secondary therapeutic agent can comprise protein. The protein can be a whey protein, soy protein, pea protein, a calcium caseinate protein, or a combination thereof. In yet another example the primary or secondary therapeutic agent comprises curcumin. In a further embodiment, the primary or secondary therapeutic agent comprises a fiber source and/or inulin.

In one embodiment, the bergamot extract can be derived from *Citrus bergamia Risso*. In one embodiment, the mangosteen extract can be derived from *Garcinia mangosana*. In one example, the mangosteen extract can be an extract of the fruit, the pericarp, or both the fruit and the pericarp. The fruit extract can be derived from any part of the fruit including but not limited to the pulp, the rind, the seeds, or a combination thereof. In one embodiment the mangosteen pericarp extract is derived solely from the rind of the fruit.

In some embodiments, the apple, grape, green tea, and olive extract composition further comprises blueberry extract/concentrate, capsicum extract, and turmeric extract. In one example, the blueberry extract/concentrate can be obtained from *Vaccinium angustifolium*. In one example the blueberry concentrate can be a dried powder created without the use of a solvent. In one embodiment, it can take about 5 kg, about 8 kg, about 10 kg, or about 12 kg of blueberries to obtain 1 kg of dried powder. In one embodiment, the capsicum extract can be obtained from *Capsicum annuum*. In some embodiments, capsicum extract can be derived from powdered dried ripe fruits. In one example the turmeric extract can be obtained from *Curcuma longa*. In some embodiments, the turmeric extract can comprise an extract of the root, the rhizome, or a combination thereof. In another embodiment, the turmeric extract can be derived from a turmeric powder. In on embodiment, the turmeric powder can have from about 1 to about 10% curcuminoids, from about 3 to about 5% curcuminoids, from about 2% to about 8% curcuminoids, or from about 4% to about 12% curcuminoids. In some embodiments, the grape extract can comprise an extract of a grape skin and a grape seed extract. In one embodiment, the composition comprising the blueberry concentrate, capsicum extract, and turmeric extract in addition to the apple, grape, green tea, and olive extract can further comprise a mangosteen extract. The mangosteen extract can comprise a *Garcinia mangostana* extract and can be a fruit extract, a pericarp extract, or a combination thereof. In other embodiments, the composition comprising the blueberry concentrate, capsicum extract, and turmeric extract in addition to the apple, grape, green tea, and olive extract can further comprise a bergamot extract. In another embodiment, the composition comprising the blueberry concentrate, capsicum extract, and turmeric extract in addition to the apple, grape, green tea, and olive extract can further comprise a mangosteen extract and a bergamot extract.

The antioxidant compositions can have a variety of mechanisms of action. In one embodiment the antioxidant composition can quench free radicals. In another embodiment, the antioxidant composition can modulate peroxynitrate formation. In one example, the antioxidant composition modulates stress signaling enzymes such as matrix metalloproteinases and myeloperoxidase.

The antioxidant compositions can be used for modulating oxidative stress in a mammal in need thereof. Oxidative stress related conditions can include, but without limitation, metabolic syndrome, type I, type II and type III diabetes, obesity, high cholesterol levels accompanied by increased oxidized LDL cholesterol, various forms of inflammation including osteoarthritis, rheumatoid arthritis, endotoxemia, inflammatory bowel disease, leaky gut, Crohn's disease, prostate hyperplasia, lower urinary tract symptoms (LUTS), pulmonary arterial hypertension, diminished exercise capacity, premature ejaculation, low female sex drive, congestive disorders, cardiac failure, pulmonary hypertension, various cardiovascular diseases, motor dysfunction, cognitive disorders including Alzheimer's disease, Raynaud's phenomenon, essential hypertension, stroke, asthma, multiple sclerosis, vasculitis, Addison's Disease, lupus, thyroiditis, chronic fatigue syndrome, fibromyalgia skin disorders such as wrinkles, discolorations and sagging, as well as cancers arising from oxidized damage to DNA, and other disorders associated with tissue-specific modulation of protein kinase activity stimulated through the propagation of reactive species of oxygen and nitrogen. In one example, the mammal in need thereof has increased oxidized LDL(oxLDL) cholesterol. In another example, the mammal in need thereof has at least one of metabolic syndrome, type I, II, or II diabetes. In another example, the mammal in need thereof has at least one of leaky gut, endotoxemia, or inflammatory bowel disease.

The antioxidant compositions can be useful for treating a spectrum of physiological disorders in which oxidative stress participates through etiology, expression, or progression. The phytocomplexes and various combinations thereof that may be used to regulate oxidative stress to treat numerous disease-related signs and symptoms with a concomitant increase in the quality of life. The resulting compositions can be consumed as a dietary supplement to address the risk factors associated with oxidative stress, benign prostate hyperplasia, obesity, metabolic syndrome, diabetes, increasing exercise endurance or other inflammatory-based pathologies.

In some embodiments, the antioxidant activity can have a greater antioxidant activity than provided by an equivalent amount of any one extract or a sum of the extracts. The synergistic antioxidant activity can be greater than or about 1.1 times, about 1.2 times, about 1.3 times, about 1.5, about 1.75 times, about 2 times, about 2.5 times or about 3 times greater than the antioxidant activity provided by an equivalent amount of any one extract or a sum of the extracts. In one embodiment a composition comprising blueberry concentrate, capsicum, turmeric, apple, grape, green tea, olive and mangosteen fruit extract can have equal to or greater than 1.2 times antioxidant activity provided by an equivalent amount of any one extract or a sum of the extracts. In some embodiments this composition can have greater than 1.5 times the antioxidant activity provided by an equivalent amount of any one extract or a sum of the extracts. In another embodiment a composition comprising blueberry concentrate, capsicum, turmeric, apple, grape, green tea, olive and mangosteen pericarp extract can have equal to or greater than 1.3 times antioxidant activity provided by an equivalent amount of any one extract or a sum of the extracts. In yet another embodiment, a composition comprising blueberry concentrate, capsicum, turmeric, apple, grape, green tea, olive, mangosteen fruit, and bergamot extract can have equal to or greater than 2.5 times antioxidant activity provided by an equivalent amount of any one extract or a sum of the extracts. In a further embodiment, a composition comprising blueberry concentrate, capsicum, turmeric, apple, grape, green tea, olive, mangosteen pericarp, and bergamot extract can have equal to or greater than 1.5 times antioxidant activity provided by an equivalent amount of any one extract or a sum of the extracts.

Also presented herein is a protein kinase modulating composition, comprising a combination of apple, grape, green tea, and olive extracts in amounts that provide a greater protein kinase modulating activity than provided by an equivalent amount of any one extract or a sum of the extracts. The composition can further comprise the additional extracts, primary therapeutic agent, and/or secondary therapeutic agents as identified above. The extracts, amounts of the components, primary therapeutic agents, and/or secondary therapeutic agents can be as identified above.

The protein kinase modulating composition can dramatically and synergistically modulate kinase signaling of any of the protein kinases shown in Table 14. In one example the protein kinase modulating composition modulates the expression of Abl, ACK1, ALK, Aurora, AMPK, CaMKII, EGFR, EphA, FAK, FGFR, GSK3, IGF-1(activated), IKK, IR, MAPK1, Met, MTOR, NEK1/2/6, PAK1/4/5/6, PDGFR, PI3K, PKC, ROCKI/II, RSK1/2/34, SRC, Syk and combinations thereof. In one embodiment, the protein kinase modulating activity can comprise PI3 kinase. In another embodiment, the protein kinase modulating activity can comprise MET kinase. In yet another embodiment, the protein kinase modulating activity can comprise at least one of the Aurora kinases, Aurora-A, Aurora-B, and Aurora-C. In some embodiments, the protein kinase activity can be modulated in selected target tissue for treating signs and symptoms associated with diseases or conditions selected from the group consisting of prostate cancer, LUTS, pulmonary arterial hypertension, diminished exercise capacity, congestive cardiac failure, pulmonary hypertension, various cardiovascular diseases, motor dysfunction, cognitive disorders including Alzheimer's disease, Raynaud's phenomenon, essential hypertension, stroke, asthma, multiple sclerosis, vasculitis, various forms of inflammation including osteoarthritis, rheumatoid arthritis, type I and type II diabetes, metabolic syndrome, obesity, endotoxemia, inflammatory bowel disease, leaky gut, Crohn's disease, Addison's Disease, lupus, thyroiditis, chronic fatigue syndrome, fibromyalgia and other disorders associated with tissue-specific modulation of protein kinase activity.

The modulation of the protein kinase can reduce, minimize, or inhibit production or presence of oxidized LDL (oxLDL) cholesterol in the subject, can ameliorate at least one of metabolic syndrome, type I diabetes, type II diabetes, or type III diabetes, can ameliorates at least one of leaky gut, endotoxemia, or inflammatory bowel disease, can ameliorates at least one of obesity, inflammation conditions including osteoarthritis and rheumatoid arthritis, Crohn's disease, prostate hyperplasia, lower urinary tract symptoms, pulmonary arterial hypertension, diminished exercise capacity, premature ejaculation, low female sex drive, congestive disorders, cardiac failure, pulmonary hypertension, cardiovascular diseases, motor dysfunction, cognitive disorders including Alzheimer's disease, Raynaud's phenomenon, essential hypertension, stroke, asthma, multiple sclerosis, vasculitis, Addison's Disease, lupus, thyroiditis, chronic fatigue syndrome, fibromyalgia and skin disorders including skin wrinkles, skin discolorations and skin sagging, or can results at least one of in stimulation of skeletal muscle fatty acid oxidation and muscle glucose uptake, hepatic fatty acid oxidation and ketogenesis, inhibition of cholesterol synthesis, lipogenesis, triglyceride synthesis, inhibition of adipocyte lipolysis and lipogenesis, and modulation of insulin secretion by pancreatic beta-cells.

In one embodiment, the modulation of the protein kinases can ameliorate at least one of obesity, inflammation conditions including osteoarthritis and rheumatoid arthritis, Crohn's disease, prostate hyperplasia, lower urinary tract symptoms, pulmonary arterial hypertension, diminished exercise capacity, premature ejaculation, low female sex drive, congestive disorders, cardiac failure, pulmonary hypertension, cardiovascular diseases, motor dysfunction, cognitive disorders including Alzheimer's disease, Raynaud's phenomenon, essential hypertension, stroke, asthma, multiple sclerosis, vasculitis, Addison's Disease, lupus, thyroiditis, chronic fatigue syndrome, fibromyalgia and skin disorders including skin wrinkles, skin discolorations and skin sagging. In another embodiment, the modulation of the protein kinases can ameliorate at least one of leaky gut, endotoxemia, and inflammatory bowel disease. In a further embodiment, the modulation of the protein kinases can ameliorates at least one of at least one of metabolic syndrome, type I diabetes, type II diabetes, and type III diabetes. In another embodiment, the modulation of the protein kinase reduces, minimizes, or inhibits production or presence of oxidized LDL (oxLDL) cholesterol in the subject.

In some embodiments, the protein kinase modulating activity can have a greater protein kinase modulating activity than provided by an equivalent amount of any one extract or a sum of the extracts. The synergistic protein kinase modulating activity can be greater than or about 1.1 times, about 1.2 times, about 1.3 times, about 1.5, about 1.75 times, about 2 times, about 2.5 times or about 3 times greater than the protein kinase modulating activity provided by an equivalent amount of any one extract or a sum of the extracts.

Further presented herein are therapeutic compositions comprising a primary therapeutic agent and a combination of apple, grape, green tea, and olive extracts in amounts that increase a therapeutic effect of the primary therapeutic agent more than an increase in therapeutic effect provided by an equivalent amount of any one extract. The compositions can further comprise the additional extracts, and/or secondary therapeutic agents as identified above. The extracts, amounts, and secondary therapeutic agents can be as identified above.

The primary therapeutic agent can be any antioxidant, metabolic agent, or kinase pathway signal transducer. In one embodiment, the primary therapeutic agent can be an antioxidant. In another embodiment the primary therapeutic agent can be a metabolic agent. In yet another embodiment the primary therapeutic agent can be a kinase pathway signal transducer. In other embodiments the primary therapeutic agent can be an agent that enhances NO production. In one embodiment, the primary therapeutic agent can comprise a member selected from the group consisting of bergamot, mangosteen, berberine, arginine, citrulline, glutamine, zinc, beet, loclo, protein, curcumin, phytosterols, fish oil, CoQ10, vitamins, fiber, inulin, aminogen®, biotin, black bean powder, copper citrate, ferrous fumarate, fructose, garbanzo bean, gum arabic, magnesium oxide, manganese citrate, medium chain triglycerides, pea fiber, pea protein isolate, potassium citrate, vitamin B6, riboflavin, rice bran, rice protein, sodium citrate, sodium selenate, thiamin HCl, vitamin D2, vitamin E, zinc citrate, adzuki bean, D-calcium pantothenate, lycopene, polyphenols, ascorbic acid, β-glucans, lutein, blueberry, borage oil, broccoli flowers, carrot root, cranberry fruit, chromium nicotinate, cyanocobalamin, flax seed/*Linum usitatissimum*, folic acid, lo han extract, niacinamide, pomegranate fruit, vitamin A, carotentiods, vitamin E, phytosterols, lignin, CoQ10, glutathione, and combinations thereof.

In one example the primary therapeutic agent regulates metabolic dysfunction. In some embodiments, the primary therapeutic agent which regulates metabolic dysfunction comprises a member selected from the group consisting of aminogen®, biotin, black bean powder, copper citrate, ferrous fumarate, fructose, garbanzo bean, gum arabic, inulin, magnesium oxide, manganese citrate, medium chain triglycerides, pea fiber, pea protein isolate, potassium citrate, vitamin B6, riboflavin, rice bran, rice protein, sodium citrate, sodium selenate, thiamin HCl, vitamin D2, vitamin E, zinc citrate, adzuki bean, D-calcium pantothenate, and combinations thereof. In another embodiment, the therapeutic agent can be aminogen®. In another example, the primary therapeutic agent can be inulin.

In another example, the primary therapeutic agent can be an antioxidant. In some embodiments the antioxidant comprises a member selected from the group consisting of lycopene, polyphenols, ascorbic acid, β-glucans, lutein, blueberry, borage oil, broccoli flowers, carrot root, cranberry fruit, chromium nicotinate, cyanocobalamin, flax seed/*Linum usitatissimum*, folic acid, lo han extract, niacinamide, pomegranate fruit, vitamin A, carotentiods, vitamin E, zinc, sodium selenate, phytosterols, lignin, CoQ10, glutathione, and combinations thereof. In one embodiment, the antioxidant comprises a member selected from the group consisting of ascorbic acid, β-glucans, blueberry, borage oil, broccoli flowers, carrot root, cranberry fruit, chromium nicotinate, cyanocobalamin, flax seed/*Linum usitatissimum*, folic acid, lo han extract, niacinamide, pomegranate fruit, vitamin A, phytosterols, and combinations thereof.

In one example, the primary therapeutic agent can comprise fish oil. In one example, the fish oil can lower TG, LDLc, oxLDLc, raise HDLc, or any combination thereof. The extracts when combined with the fish oil can enhance the TG lowering properties of the fish oil, improve NO formation, and lower blood pressure. In one example the fish oil can be included in the composition at between 1-5 grams.

In another example, the primary therapeutic agent can be berberine. In one example the berberine can influence endotoxemia and inflammation in the body. In one example, this formulation can inhibit or down-regulate MPO an enzyme known to in turn inhibit or remove eNOS and NO production. Endotoxemia and inflammation are initiators of metabolic dysfunction/CVD and obesity. The therapeutic composition comprising berberine as the primary therapeutic agent can be used to combat metabolic dysfunction.

The oxidative stress modulating compositions, protein kinase modulating compositions, and/or the therapeutic compositions discussed above can be provided in any convenient form. These compositions can be provided as dietary supplement in capsule or tablet form. They can be formulated into a food or drink, and provided, for example, as a snack bar, a cereal, a drink, a gum, or in any other easily ingested form. They can also be provided as a cream or lotion for topical application. In one example, the composition can be an oral composition in the form of discrete units as capsules, sachets, tablets, soft gels or lozenges, each containing a predetermined amount of the active ingredient; in the form of a powder or granules; in the form of a solution or a suspension in an aqueous liquid or non-aqueous liquid, such as ethanol or glycerol; or in the form of an oil-in-water emulsion or a water-in-oil emulsion. Such oils may be edible oils, such as e.g. cottonseed oil, sesame oil, coconut oil, sunflower oil, or peanut oil. Suitable dispersing or suspending agents for aqueous suspensions include synthetic or natural gums such as tragacanth, alginate, gum arabic, dextran, sodium carboxymethylcellulose, gelatin, methylcellulose and polyvinylpyrrolidone. In another embodiment, the oral dosage form can comprise a capsule, a tablet, a powder, a beverage, a syrup, a suspension, or a food.

In addition, the compositions can be formulated as a depot preparation. Such long-acting compositions may be administered by implantation (e.g. subcutaneously, intra-abdominally, or intramuscularly) or by intramuscular injection. Thus, for example, the active ingredient may be formulated with suitable polymeric or hydrophobic materials (for example, as an emulsion in a pharmaceutically acceptable oil), or an ion exchange resin.

In some embodiments, the oxidative stress modulating compositions, protein kinase modulating compositions, and/or the therapeutic compositions discussed above can further comprise a pharmaceutically acceptable carrier. In some embodiments, the formulations can comprise pharmaceutically acceptable excipients. Exemplary pharmaceutically acceptable excipients can be selected from the group consisting of coatings, isotonic and absorption delaying agents, binders, adhesives, lubricants, disintergrants, coloring agents, flavoring agents, sweetening agents, absorbents, detergents, and emulsifying agents.

When the formulation includes an emulsifying agent, the emulsifiers can be added to improve the stability of the final product. Exemplary emulsifiers include, but are not limited to, lecithin (e.g., from egg or soy), or mono- and diglycerides. Other emulsifiers are readily apparent to the skilled artisan and selection of suitable emulsifier(s) will depend, in part, upon the formulation and final product.

The formulation can further include flavorings, coloring agents, spices, nuts, preservatives, antioxidants, vitamins, minerals, proteins, fats, and/or carbohydrates. The amount of other ingredients can vary based on the particular design, intended dosage, and method of administration. The total amount of other ingredients can also depend, in part, upon the condition and weight of the subject.

Flavors, coloring agents, spices, nuts and the like can be incorporated into the product. Flavorings can be in the form of flavored extracts, volatile oils, chocolate flavorings (e.g., non-caffeinated cocoa or chocolate, chocolate substitutes such as carob), peanut butter flavoring, cookie crumbs, crisp rice, vanilla or any commercially available flavoring. Flavorings can be protected with mixed tocopherols. Examples of useful flavorings include but are not limited to pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; or volatile oils, such as balm oil, bay oil, bergamot oil, cedarwood oil, cherry oil, walnut oil, cinnamon oil, clove oil, or peppermint oil; peanut butter, chocolate flavoring, vanilla cookie crumb, butterscotch or toffee. In one embodiment, the formulation can contain berry or other fruit flavors. The food compositions may further be coated, for example with a yogurt coating.

Preservatives or stabilizers can be added to the formulation to extend the shelf life of the product. Exemplary preservatives include potassium sorbate, sodium sorbate, potassium benzoate, sodium benzoate, or calcium disodium EDTA.

The formulation can also include natural or artificial sweeteners. In one embodiment, the potential sweeteners can include glucose, sucrose, fructose, saccharides, cyclamates, aspartamine, sucralose, aspartame, acesulfame K, sorbitol, or a combination thereof.

The formulation can further include pharmaceutically acceptable forms of vitamins, minerals, and other nutrients. The nutrients chosen for inclusion in the formulation can vary depending on the particular design, intended dosage, method of administration, and condition of the subject. Individuals skilled in the art are aware of vitamins, minerals, and other nutrients that can be incorporated into formulations and how to incorporate these.

The components in the formulation can be included as salts. In particular, pharmaceutically acceptable salts of the components are contemplated. A "pharmaceutically acceptable salt" is a combination of a compound and either an acid or a base that forms a salt (such as, for example, the magnesium salt, denoted herein as "Mg" or "Mag") with the compound. Pharmaceutically acceptable salts can be tolerated by a subject under therapeutic conditions. In general, a pharmaceutically acceptable salt of a compound will have a therapeutic index (the ratio of the lowest toxic dose to the lowest therapeutically effective dose) of 1 or greater. Those skilled in the art recognize that the lowest therapeutically effective dose will vary from subject to subject and from indication to indication, and will thus adjust the formulation accordingly.

In addition, polymers may be added according to standard methodologies in the art for sustained release of a given compound.

Any compositions used to treat a disease or condition will use a pharmaceutical grade compound and that the composition will further comprise a pharmaceutically acceptable carrier. It is further contemplated that these compositions of the invention may be prepared in unit dosage forms appropriate to both the route of administration and the disease and patient to be treated. The compositions may conveniently be presented in dosage unit form be prepared by any of the methods well known in the art of pharmacy. All methods include the step of bringing the active ingredient into association with the vehicle that constitutes one or more auxiliary constituents. In general, the compositions are prepared by uniformly and intimately bringing the active ingredient into association with a liquid vehicle or a finely divided solid vehicle or both, and then, if necessary, shaping the product into the desired composition.

Also presented herein are methods of regulating oxidative stress in a subject. The method can comprise administering to the subject a therapeutically effective combination of apple, grape, green tea, and olive extracts, in amounts that provide a combined antioxidant activity that is greater than an antioxidant activity provided by an equivalent amount of any one extract or a sum of the extracts. In one example, the method can further comprise administering to the subject at least one secondary therapeutic agent. The secondary therapeutic agent can be co-administered in a single formulation, administered separately, or administered sequentially with the administration of the apple, grape, green tea, and olive extracts. The method can comprise administering any of the additional extracts, and/or secondary therapeutic agents as identified above. The extracts, amounts, and secondary therapeutic agents can be as identified above.

The method can regulate stress related pathologies and metabolic disorders comprise at least one member selected from the group consisting of metabolic syndrome, type 1 diabetes, type 2 diabetes, obesity, high cholesterol levels, oxidized LDL cholesterol, inflammation, osteoarthritis, rheumatoid arthritis, endotoxemia, inflammatory bowel disease, leaky gut, Crohn's disease, prostate hyperplasia, lower urinary tract symptoms, pulmonary arterial hypertension, diminished exercise capacity, premature ejaculation, low female sex drive, congestive disorders, cardiac failure, pulmonary hypertension, various cardiovascular diseases, motor dysfunction, cognitive disorders including Alzheimer's disease, Raynaud's phenomenon, essential hypertension, stroke, asthma, multiple sclerosis, vasculitis, Addison's Disease, lupus, thyroiditis, chronic fatigue syndrome, fibromyalgia skin disorders, wrinkles, skin discoloration, sagging skin, cancers arising from oxidized damage to DNA, and combinations thereof.

Further presented herein is a method of regulating disease-associated protein kinase activity in a subject comprising administering to the subject a therapeutically effective combination of an apple extract, a grape extract, a green tea extract, and an olive extract, in amounts that provide a combined kinase regulating activity that is greater than an a kinase regulating activity provided by an equivalent amount of any one extract or a sum of the extracts. In one example the method can further comprise administering to the subject at least one secondary therapeutic agent. The secondary therapeutic agent can be co-administered in a single formulation, administered separately, or administered sequentially with the administration of the apple, grape, green tea, and olive extracts. The method can comprise administering any of the additional extracts, and/or secondary therapeutic agents as identified above. The extracts, amounts, and secondary therapeutic agents can be as identified above.

The method can modulate activity of protein kinases of any of the protein kinases shown in Table 14. In one example the method modulates the expression of: Abl, ACK1, ALK, Aurora, AMPK, CaMKII, EGFR, EphA, FAK, FGFR, GSK3, IGF-1(activated), IKK, IR, MAPK1, Met, MTOR, NEK1/2/6, PAK1/4/5/6, PDGFR, PI3K, PKC, ROCKI/II, RSK1/2/34, SRC, Syk and combinations thereof. In one embodiment the protein kinase modulating activity can comprise PI3 kinase. In another embodiment, the protein kinase modulating activity can comprise MET kinase. In yet another embodiment, the protein kinase modulating activity can comprise at least one of the Aurora kinases, Aurora-A, Aurora-B, and Aurora-C.

The administration step of the method of regulating oxidative stress and method of regulating disease-associated protein kinase activity can be administered to a subject in need of such activity. The formulation in the method can be administered in the form of an oral, transdermal, transmucosal, rectal, ophthalmic (including intravitreal or intracameral), nasal, nasal by inhalation, topical (including buccal and sublingual), vaginal, parenteral (including subcutaneous, intramuscular, intravenous, intradermal, and intratracheal), by implantation, or intramuscularly. In one exemplary embodiment the method administers the formulation orally.

The amount administered can coincide with the recommended daily amounts of each ingredient. The actual amount of each ingredient per unit dosage will depend upon the number of units administered daily to the individual in need thereof. This is a matter of product design and is well within the skill of the nutritional supplement formulator.

Additionally presented are methods of enhancing the therapeutic effect of a primary therapeutic agent. In one example, the method can comprise combining a primary therapeutic agent with apple, grape, green tea, and olive extracts in amounts that increase the therapeutic effect of the primary therapeutic agent more than an increase provided by an equivalent amount of any one extract. In one example, the method can further comprise administering the formulation to a subject in need thereof. In one embodiment the method additionally comprises administering a secondary therapeutic agent can be co-administered in a single formulation, administered separately, or administered sequentially with the administration of the apple, grape, green tea, and olive extracts. The method can comprise administering any of the additional extracts, and/or secondary therapeutic agents as identified above. The extracts, amounts, primary therapeutic agents, and secondary therapeutic agents can be as identified above.

Further presented herein are methods of making an activity-enhanced compositions for regulating oxidative stress, methods of making protein kinase modulating compositions, and making therapeutic, including therapeutic-specific compositions. The methods of making the oxidative stress modulating compositions and protein kinase modulating compositions can comprise combining apple, grape, green tea, and olive extracts in amounts that provide a greater antioxidant activity than provided by an equivalent amount of any one extract or a sum of the extracts. The method of making the therapeutic composition further comprises providing a primary therapeutic agent and combining the primary therapeutic agent with apple, grape, green tea, and olive extracts.

In any or all of the methods above, the extracts can be created from the raw ingredients. When formulation from raw ingredients, the apple, grape, green tea and olive extracts can be extracted using an extraction solvent selected from the group consisting of water, ethanol, ethyl acetate, and combinations thereof. In an example, the extraction process can include forming a pulp concentrate of the raw material, extracting the raw materials, purifying the raw materials, eluting the raw materials, collecting the eluted material, concentrating the material, and spray drying material. In another example, the extraction process can further comprise filtering the material.

In one example, the method can further comprise combining at least one secondary therapeutic agent to the apple, grape, green tea, and olive extracts. The extracts, amounts, primary therapeutic agents, and secondary therapeutic agents can be as identified above.

In some embodiments the compositions, methods of use, and methods of making the oxidative stress modulating compositions, protein kinase modulating compositions, and/or the therapeutic compositions discussed above can include formulating the compositions in the form of a pharmaceutical pack or kit. The pharmaceutical pack or kit can comprise one or more containers filled with one or more of the ingredients of the compositions of the invention (e.g., nutritional supplement in the form of a powder and capsules). Optionally associated with such container(s) can be a notice in the form prescribed by a government agency regulating the manufacture, use or sale of pharmaceutical products, which notice reflects approval by the agency of manufacture, use of sale for human administration. The pack or kit can be labeled with information regarding mode of administration, sequence of administration (e.g., separately, sequentially or concurrently), or the like. The pack or kit may also include means for reminding the patient to take the therapy. The pack or kit can be a single unit dosage of the combination therapy or it can be a plurality of unit dosages. In particular, the agents can be separated, mixed together in any combination, present in a formulation or tablet.

Embodiments

In one embodiment there is provided, an oxidative stress modulating composition comprising a combination of apple, grape, green tea, and olive extract in amounts that provide a greater antioxidant activity than provided by an equivalent amount of any one extract or a sum of the extracts.

In one embodiment of the oxidative stress modulating composition, the apple extract comprises an extract of a species *Malus pumila.*

In one embodiment of the oxidative stress modulating composition, the apple extract in the composition comprises both a skin and a fruit of the *Malus pumila.*

In one embodiment of the oxidative stress modulating composition, the grape extract comprises an extract of a species *Vitis vinifera.*

In one embodiment of the oxidative stress modulating composition, the grape extract in the composition comprises seeds of the *Vitis vinifera.*

In one embodiment of the oxidative stress modulating composition, the grape extract in the composition comprises from about 75 wt % to about 95 wt % phenolics on a dry weight basis.

In one embodiment of the oxidative stress modulating composition, the green tea extract comprises an extract of leaves of a species *Camellia sinensis.*

In one embodiment of the oxidative stress modulating composition, the olive extract comprises an extract of a subspecies *Olea europaea europaea.*

In one embodiment of the oxidative stress modulating composition, the olive extract in the composition comprises leaves of the *Olea europaea europaea.*

In one embodiment of the oxidative stress modulating composition, at least one of the extracts in the composition is present in a different amount than an amount of at least one of another extract.

In one embodiment of the oxidative stress modulating composition, the apple, grape, green tea, and olive extracts are present in the composition at a weight ratio of about 1:1:1:1.

In one embodiment of the oxidative stress modulating composition, the apple, grape, green tea, and olive extracts are present in the composition at a weight ratio of about 6:1:3:1

In one embodiment of the oxidative stress modulating composition, the apple, grape, green tea, and olive extracts comprise extracts of the leaves, skin, rind, pulp, juice, seeds, or combinations thereof.

In one embodiment, the oxidative stress modulating composition further comprises at least one primary or secondary therapeutic agent.

In one embodiment of the oxidative stress modulating composition, the at least one primary or secondary therapeutic agent comprises a member selected from the group consisting of bergamot, mangosteen, berberine, arginine, citrulline, glutamine, zinc, beet, loclo, protein, curcumin, phytosterols, fish oil, CoQ10, vitamins, fiber, inulin, and combinations thereof.

In one embodiment of the oxidative stress modulating composition, the at least one primary or secondary therapeutic agent comprises bergamot.

In one embodiment of the oxidative stress modulating composition, the at least one primary or secondary therapeutic agent comprises mangosteen.

In one embodiment of the oxidative stress modulating composition, the at least one primary or secondary therapeutic agent comprises berberine.

In one embodiment of the oxidative stress modulating composition, the composition comprising a combination of apple, grape, green tea, and olive extract further comprises at least one secondary therapeutic agent.

In one embodiment of the oxidative stress modulating composition, the at least one primary or secondary therapeutic agent comprises arginine and beet.

In one embodiment of the oxidative stress modulating composition, the at least one primary or secondary therapeutic agent comprises citrulline and beet.

In one embodiment of the oxidative stress modulating composition, the at least one primary or secondary therapeutic agent comprises phytosterols.

In one embodiment of the oxidative stress modulating composition, the at least one primary or secondary therapeutic agent comprises protein.

In one embodiment of the oxidative stress modulating composition, the protein comprises at least one member selected from the group consisting of whey protein, soy protein, pea protein, calcium caseinate protein, and combinations thereof.

In one embodiment of the oxidative stress modulating composition, the at least one primary or secondary therapeutic agent comprises curcumin.

In one embodiment of the oxidative stress modulating composition, the at least one primary or secondary therapeutic agent comprises a fiber source and inulin.

In one embodiment of the oxidative stress modulating composition, the composition further comprises a pharmaceutically acceptable carrier.

In one embodiment of the oxidative stress modulating composition, the composition is an oral dosage formulation.

In one embodiment of the oxidative stress modulating composition, the oral dosage form comprises a capsule, a tablet, a powder, a beverage, a syrup, a suspension, or a food.

In one embodiment of the oxidative stress modulating composition, the antioxidant activity modulates stress related pathologies and metabolic disorders.

In one embodiment of the oxidative stress modulating composition, the composition the antioxidant activity of the oxidative stress modulating composition modulates stress related pathologies and metabolic disorders.

In one embodiment of the oxidative stress modulating composition, the stress related pathologies and metabolic disorders comprise at least one member selected from the group consisting of metabolic syndrome, type 1 diabetes, type 2 diabetes, obesity, high cholesterol levels, oxidized LDL cholesterol, inflammation, osteoarthritis, rheumatoid arthritis, endotoxemia, inflammatory bowel disease, leaky gut, Crohn's disease, prostate hyperplasia, lower urinary tract symptoms, pulmonary arterial hypertension, diminished exercise capacity, premature ejaculation, low female sex drive, congestive disorders, cardiac failure, pulmonary hypertension, various cardiovascular diseases, motor dysfunction, cognitive disorders including Alzheimer's disease, Raynaud's phenomenon, essential hypertension, stroke, asthma, multiple sclerosis, vasculitis, Addison's Disease, lupus, thyroiditis, chronic fatigue syndrome, fibromyalgia skin disorders, wrinkles, skin discoloration, sagging skin, cancers arising from oxidized damage to DNA, and combinations thereof.

In one embodiment of the oxidative stress modulating composition, the antioxidant activity modulates oxidized LDL.

In one embodiment of the oxidative stress modulating composition, the antioxidant activity modulates at least one of metabolic syndrome, type I diabetes, type II diabetes, or type III diabetes.

In one embodiment of the oxidative stress modulating composition, the antioxidant activity modulates at least one of leaky gut, endotoxemia, or inflammatory bowel disease.

In one embodiment of the oxidative stress modulating composition, the oxidative stress modulating composition further comprises blueberry concentrate, capsicum extract, and turmeric extract.

In one embodiment of the oxidative stress modulating composition further comprising blueberry concentrate, capsicum extract, and turmeric extract, the blueberry concentrate comprises *Vaccinium angustifolium*, the capsicum extract comprises *Capsicum annuum*, and the turmeric extract comprises *Curcuma longa*.

In one embodiment of the oxidative stress modulating composition, the grape extract comprises grape skin and grape seed from *Vitis vinifera* in the oxidative stress modulating composition further comprises blueberry concentrate, capsicum extract, and turmeric extract.

In one embodiment of the oxidative stress modulating composition, the oxidative stress modulating composition further comprises blueberry concentrate, capsicum extract, turmeric extract, and mangosteen fruit extract.

In the embodiment of the oxidative stress modulating composition above, the composition comprises greater than 1.5 times the antioxidant activity of an equivalent amount of any one extract or concentrate or a sum of the extracts and concentrate.

In one embodiment of the oxidative stress modulating composition, the oxidative stress modulating composition further comprises blueberry concentrate, capsicum extract, turmeric extract, and bergamot extract.

In the embodiment of the oxidative stress modulating composition above, the composition comprises greater than 1.5 times the antioxidant activity of an equivalent amount of any one extract or concentrate or a sum of the extracts and concentrate.

In one embodiment of the oxidative stress modulating composition the bergamont extract comprises *Citrus bergamia Risso*.

In one embodiment of the oxidative stress modulating composition, the oxidative stress modulating composition further comprises blueberry concentrate, capsicum extract, turmeric extract, and mangosteen pericarp extract.

In the embodiment of the oxidative stress modulating composition above, the composition comprises greater than 1.25 times the antioxidant activity of an equivalent amount of any one extract or concentrate or a sum of the extracts and concentrate.

In one embodiment of the oxidative stress modulating composition, the oxidative stress modulating composition further comprises blueberry concentrate, capsicum extract, turmeric extract, mangosteen pericarp extract, and bergamot extract.

In one embodiment, the oxidative stress modulating composition further comprises blueberry concentrate, capsicum extract, turmeric extract, mangosteen pericarp extract and bergamot extract modulates oxidized LDL.

In one embodiment, a protein kinase modulating composition comprising a combination of apple, grape, green tea, and olive extracts in amounts that provide a greater protein kinase modulating activity than provided by an equivalent amount of any one extract or a sum of the extracts.

In one embodiment of the protein kinase modulating composition, the apple extract comprises an extract of a species *Malus pumila*.

In one embodiment of the protein kinase modulating composition, the apple extract comprises both skin and fruit of the *Malus pumila*.

In one embodiment of the protein kinase modulating composition, the grape extract comprises an extract of a species *Vitis vinifera*.

In one embodiment of the protein kinase modulating composition, the grape extract comprises seeds of the *Vitis vinifera*.

In one embodiment of the protein kinase modulating composition, the grape extract comprises from about 75 wt % to about 95 wt % phenolics on a dry weight basis.

In one embodiment of the protein kinase modulating composition, the green tea extract comprises an extract of leaves of a species *Camellia sinensis*.

In one embodiment of the protein kinase modulating composition, the olive extract comprises an extract of a subspecies *Olea europea europaea*.

In one embodiment of the protein kinase modulating composition, the olive extract comprises leaves of the *Olea europea europea*.

In one embodiment of the protein kinase modulating composition, at least one of the extracts in the composition is present in a different amount than an amount of at least one of another extract.

In one embodiment of the protein kinase modulating composition, the apple, grape, green tea, and olive extracts are present at a weight ratio of about 1:1:1:1.

In one embodiment of the protein kinase modulating composition, the apple, grape, green tea, and olive extracts are present at a weight ratio of about 6:1:3:1

In one embodiment of the protein kinase modulating composition, the apple, grape, green tea, and olive extracts comprise leaves, skin, rind, pulp, juice, seeds, or combinations thereof.

In one embodiment, the protein kinase modulating composition further comprises at least one primary or secondary therapeutic agent.

In one embodiment of the protein kinase modulating composition, the at least one primary or secondary therapeutic agent comprises a member selected from the group consisting of bergamot, mangosteen, berberine, arginine, citrulline, glutamine, beet, protein, curcumin, phytosterols, fish oil, CoQ10, vitamins, fiber, inulin, and combinations thereof.

In one embodiment of the protein kinase modulating composition, the at least one primary or secondary therapeutic agent comprises bergamot.

In one embodiment of the protein kinase modulating composition, the at least one primary or secondary therapeutic agent comprises mangosteen.

In one embodiment of the protein kinase modulating composition, the at least one primary or secondary therapeutic agent comprises berberine.

In one embodiment of the protein kinase modulating composition, the at least one primary or secondary therapeutic agent comprises arginine and beet.

In one embodiment of the protein kinase modulating composition, the at least one primary or secondary therapeutic agent comprises citrulline and beet.

In one embodiment of the protein kinase modulating composition, the at least one primary or secondary therapeutic agent comprises phytosterols.

In one embodiment of the protein kinase modulating composition, the at least one primary or secondary therapeutic agent comprises protein.

In one embodiment of the protein kinase modulating composition, the protein comprises at least one member selected from the group consisting of whey protein, soy protein, pea protein, calcium caseinate protein, and combinations thereof.

In one embodiment of the protein kinase modulating composition, the at least one primary or secondary therapeutic agent comprises curcumin.

In one embodiment of the protein kinase modulating composition, the at least one primary or secondary therapeutic agent comprises a fiber source and inulin.

In one embodiment, the protein kinase modulating composition further comprises a pharmaceutically acceptable carrier.

In one embodiment, the protein kinase modulating composition is an oral dosage formulation.

In one embodiment of the protein kinase modulating composition, the oral dosage form comprises a capsule, a tablet, a powder, a beverage, a syrup, a suspension, or a food.

In one embodiment of the protein kinase modulating composition, the protein kinase modulating activity is a member selected from the group consisting of: Abl, ACK1, ALK, Aurora, AMPK, CaMKII, EGFR, EphA, FAK, FGFR, GSK3, IGF-1(activated), IKK, IR, MAPK1, Met, MTOR, NEK1/2/6, PAK1/4/5/6, PDGFR, PI3K, PKC, ROCKI/II, RSK1/2/34, SRC, Syk and combinations thereof.

In one embodiment of the protein kinase modulating composition, the modulation of the protein kinase ameliorates at least one of obesity, inflammation conditions including osteoarthritis and rheumatoid arthritis, Crohn's disease, prostate hyperplasia, lower urinary tract symptoms, pulmonary arterial hypertension, diminished exercise capacity, premature ejaculation, low female sex drive, congestive disorders, cardiac failure, pulmonary hypertension, cardiovascular diseases, motor dysfunction, cognitive disorders including Alzheimer's disease, Raynaud's phenomenon, essential hypertension, stroke, asthma, multiple sclerosis, vasculitis, Addison's Disease, lupus, thyroiditis, chronic fatigue syndrome, fibromyalgia and skin disorders including skin wrinkles, skin discolorations and skin sagging.

In one embodiment of the protein kinase modulating composition, the modulation of the protein kinase ameliorates at least one of leaky gut, endotoxemia, and inflammatory bowel disease.

In one embodiment of the protein kinase modulating composition, the modulation of the protein kinase results ameliorates at least one of metabolic syndrome, type I diabetes, type II diabetes, and type III diabetes.

In one embodiment of the protein kinase modulating composition, the modulation of the protein kinase reduces, minimizes, or inhibits production or presence of oxidized LDL (oxLDL) cholesterol in the subject.

In one embodiment, the protein kinase modulating composition, further comprises blueberry concentrate, capsicum extract, and turmeric extract.

In one embodiment, the protein kinase modulating composition further comprises blueberry concentrate, capsicum extract, and turmeric extract, the blueberry concentrate comprises *Vaccinium angustifolium*, the capsicum extract comprises *Capsicum annuum*, and the turmeric extract comprises *Curcuma longa*.

In one embodiment, the protein kinase modulating composition further comprises blueberry concentrate, capsicum extract, and turmeric extract, the grape extract comprises grape skin and grape seed from *Vitis vinifera*.

In one embodiment, the protein kinase modulating composition further comprises blueberry concentrate, capsicum extract, turmeric extract, and a mangosteen fruit extract.

In one embodiment, the protein kinase modulating composition further comprises blueberry concentrate, capsicum extract, turmeric extract, and bergamot extract *Citrus bergamia Risso*.

In one embodiment, the protein kinase modulating composition further comprises blueberry concentrate, capsicum extract, turmeric extract, and a mangosteen pericarp extract.

In one embodiment, the protein kinase modulating composition further comprises blueberry concentrate, capsicum extract, turmeric extract, mangosteen pericarp extract, and bergamot extract *Citrus bergamia Risso*.

In one embodiment, the protein kinase modulating composition further comprising blueberry concentrate, capsicum extract, turmeric extract, mangosteen pericarp extract, and bergamot extract *Citrus bergamia* Risso, has a protein kinase modulating activity comprising a member selected from the group consisting of: Abl, ACK1, ALK, Aurora, AMPK, CaMKII, EGFR, EphA, FAK, FGFR, GSK3, IGF-1(activated), IKK, IR, MAPK1, Met, MTOR, NEK1/2/6, PAK1/4/5/6, PDGFR, PI3K, PKC, ROCKI/II, RSK1/2/34, SRC, Syk and combinations thereof.

In one embodiment, the protein kinase modulating composition further comprising blueberry concentrate, capsicum extract, turmeric extract, mangosteen pericarp extract, and bergamot extract *Citrus bergamia Risso*, has a protein kinase modulating activity comprising modulating PI3 kinase.

In one embodiment, the protein kinase modulating composition further comprising blueberry concentrate, capsicum extract, turmeric extract, mangosteen pericarp extract, and bergamot extract *Citrus bergamia Risso*, has a protein kinase modulating activity comprising modulating MET kinase.

In one embodiment, the protein kinase modulating composition further comprising blueberry concentrate, capsicum extract, turmeric extract, mangosteen pericarp extract, and bergamot extract *Citrus bergamia Risso*, has a protein kinase modulating activity comprising modulating comprises at least one of the Aurora kinases, Aurora-A, Aurora-B, and Aurora-C. In one embodiment presented herein is a therapeutic composition comprising a primary therapeutic agent and a combination of apple, grape, green tea, and olive extracts in amounts that increase a therapeutic effect of the primary therapeutic agent more than an increase in therapeutic effect provided by an equivalent amount of any one extract.

In one embodiment of the therapeutic composition, the apple, grape, green tea, and olive extracts are present in the composition at a weight ratio of about 1:1:1:1.

In one embodiment of the therapeutic composition, the apple, grape, green tea, and olive extracts are present in the composition at a weight ratio of about 6:1:3:1

In one embodiment the therapeutic composition, further comprises at least one secondary therapeutic agent.

In one embodiment of the therapeutic composition, the at least one secondary therapeutic agent comprises a member selected from the group consisting of bergamot, mangosteen, berberine, arginine, citrulline, glutamine, zinc, beet, loclo, protein, curcumin, phytosterols, fish oil, CoQ10, vitamins, fiber, inulin, and combinations thereof.

In one embodiment of the therapeutic composition, the at least one secondary therapeutic agent comprises mangosteen and the mangosteen comprises a mangosteen fruit extract, a mangosteen pericarp extract, or a combination thereof.

In one embodiment of the therapeutic composition, the at least one secondary therapeutic agent comprises bergamot.

In one embodiment of the therapeutic composition, the composition further comprise arginine and citrulline.

In one embodiment of the therapeutic composition, the therapeutic agent regulates metabolic dysfunction.

In one embodiment of the therapeutic composition, the therapeutic agent comprises a member selected from the group consisting of aminogen®, biotin, black bean powder, copper citrate, ferrous fumarate, fructose, garbanzo bean, gum arabic, inulin, magnesium oxide, manganese citrate, medium chain triglycerides, pea fiber, pea protein isolate, potassium citrate, vitamin B6, riboflavin, rice bran, rice protein, sodium citrate, sodium selenate, thiamin HCl, vitamin D2, vitamin E, zinc citrate, adzuki bean, D-calcium pantothenate, and combinations thereof.

In one embodiment of the therapeutic composition, the therapeutic agent comprises an antioxidant.

In one embodiment of the therapeutic composition, the therapeutic agent comprises an antioxidant selected from the group consisting of ascorbic acid, β-glucans, blueberry, borage oil, broccoli flowers, carrot root, cranberry fruit, chromium nicotinate, cyanocobalamin, flax seed/*Linum usitatissimum*, folic acid, lo han extract, niacinamide, pomegranate fruit, vitamin A, phytosterols, and combinations thereof.

In one embodiment presented herein is a method of regulating oxidative stress in a subject comprising, administering to the subject a therapeutically effective combination of apple, grape, green tea, and olive extracts, in amounts that provide a combined antioxidant activity that is greater than an antioxidant activity provided by an equivalent amount of any one extract or a sum of the extracts.

In one embodiment of the method of regulating oxidative stress in a subject, the apple extract comprises an extract of skin and fruit of *Malus pumila*; the grape extract comprises an extract of seeds of *Vitis vinifera*; the green tea extract comprises an extract of leaves of *Camellia sinensis*; and the olive extract comprises leaves of *Olea europea europaea*.

In one embodiment of the method of regulating oxidative stress in a subject, the apple, grape, green tea, and olive extracts are present at a weight ratio of about 1:1:1:1.

In one embodiment of the method of regulating oxidative stress in a subject, the apple, grape, green tea, and olive extracts are present at a weight ratio of about 6:1:3:1

In one embodiment of the method of regulating oxidative stress in a subject, the method further comprises administering to the subject at least one primary or secondary therapeutic agent.

In one embodiment of the method of regulating oxidative stress in a subject, the at least one primary or secondary therapeutic agent is co-administered to the subject with the therapeutically effective combination of apple, grape, green tea, and olive extracts.

In one embodiment of the method of regulating oxidative stress in a subject, the at least one primary or secondary therapeutic agent comprises a member selected from the group consisting of bergamot, mangosteen, berberine, arginine, citrulline, glutamine, zinc, beet, loclo, protein, curcumin, phytosterols, fish oil, CoQ10, vitamins, fiber, inulin, and combinations thereof.

In one embodiment of the method of regulating oxidative stress in a subject, the antioxidant activity modulates stress related pathologies and metabolic disorders.

In one embodiment of the method of regulating oxidative stress in a subject, the antioxidant activity modulates stress related pathologies and metabolic disorders and the stress related pathologies and metabolic disorders comprise at least one member selected from the group consisting of metabolic syndrome, type 1 diabetes, type 2 diabetes, obesity, high cholesterol levels, oxidized LDL cholesterol, inflammation, osteoarthritis, rheumatoid arthritis, endotoxemia, inflammatory bowel disease, leaky gut, Crohn's disease, prostate hyperplasia, lower urinary tract symptoms, pulmonary arterial hypertension, diminished exercise capacity, premature ejaculation, low female sex drive, congestive disorders, cardiac failure, pulmonary hypertension, various cardiovascular diseases, motor dysfunction, cognitive disorders including Alzheimer's disease, Raynaud's phenomenon, essential hypertension, stroke, asthma, multiple sclerosis, vasculitis, Addison's Disease, lupus, thyroiditis, chronic fatigue syndrome, fibromyalgia skin disorders, wrinkles, skin discoloration, sagging skin, cancers arising from oxidized damage to DNA, and combinations thereof.

In one embodiment of the method of regulating oxidative stress in a subject, the method further comprises administering to the subject a blueberry concentrate, a capsicum extract, and a turmeric extract.

In one embodiment of the method of regulating oxidative stress in a subject, the method further comprises administering to the subject mangosteen fruit extract.

In one embodiment of the method of regulating oxidative stress in a subject, the method further comprises administering to the subject bergamot extract.

In one embodiment of the method of regulating oxidative stress in a subject, the method further comprises administering to the subject a mangosteen pericarp extract.

In one embodiment of the method of regulating oxidative stress in a subject, the method further comprises administering to the subject mangosteen pericarp extract and bergamot extract.

In one embodiment presented herein is a method of regulating disease-associated protein kinase activity in a subject comprising: administering to the subject a therapeutically effective combination of an apple extract, a grape extract, a green tea extract, and an olive extract, in amounts that provide a combined kinase regulating activity that is greater than an a kinase regulating activity provided by an equivalent amount of any one extract or a sum of the extracts.

In one embodiment of the method of regulating disease-associated protein kinase activity in a subject, the apple extract comprises an extract of skin and fruit of *Malus pumila*; the grape extract comprises an extract of seeds of *Vitis vinifera*; the green tea extract comprises an extract of leaves of *Camellia sinensis*; and the olive extract comprises leaves of *Olea europea europaea*.

In one embodiment of the method of regulating disease-associated protein kinase activity in a subject, the apple, grape, green tea, and olive extracts are present at a weight ratio of about 1:1:1:1.

In one embodiment of the method of regulating disease-associated protein kinase activity in a subject, the apple, grape, green tea, and olive extracts are present at a weight ratio of about 6:1:3:1

In one embodiment of the method of regulating disease-associated protein kinase activity in a subject, the method further comprises administering to the subject at least one primary or secondary therapeutic agent.

In one embodiment of the method of regulating disease-associated protein kinase activity in a subject, the at least one primary or secondary therapeutic agent is co-administered to the subject with the therapeutically effective combination of apple, grape, green tea, and olive extracts.

In one embodiment of the method of regulating disease-associated protein kinase activity in a subject, the at least one primary or secondary therapeutic agent comprises a member selected from the group consisting of bergamot, mangosteen, berberine, arginine, citrulline, glutamine, zinc, beet, loclo, protein, curcumin, phytosterols, fish oil, CoQ10, vitamins, fiber, inulin, and combinations thereof.

In one embodiment of the method of regulating disease-associated protein kinase activity in a subject, the protein kinase modulating activity is a member selected from the group consisting of: Abl, ACK1, ALK, Aurora, AMPK, CaMKII, EGFR, EphA, FAK, FGFR, GSK3, IGF-1(activated), IKK, IR, MAPK1, Met, MTOR, NEK1/2/6, PAK1/4/5/6, PDGFR, PI3K, PKC, ROCKI/II, RSK1/2/34, SRC, Syk and combinations thereof.

In one embodiment of the method of regulating disease-associated protein kinase activity in a subject, the method further comprises administering to the subject a blueberry concentrate, a capsicum extract, and a turmeric extract.

In one embodiment of the method of regulating disease-associated protein kinase activity in a subject, the method further comprises administering to the subject mangosteen fruit extract.

In one embodiment of the method of regulating disease-associated protein kinase activity in a subject, the method further comprises administering to the subject bergamot extract.

In one embodiment of the method of regulating disease-associated protein kinase activity in a subject, the method further comprises administering to the subject a mangosteen pericarp extract.

In one embodiment of the method of regulating disease-associated protein kinase activity in a subject, the method further comprises administering to the subject mangosteen pericarp extract and bergamot extract.

In one embodiment presented herein is a method of enhancing a therapeutic effect provided by a primary therapeutic agent comprising: combining the primary therapeutic agent with apple, grape, green tea, and olive extracts in amounts that increase the therapeutic effect of the primary therapeutic agent more than an increase provided by an equivalent amount of any one extract.

In one embodiment of the method of enhancing a therapeutic effect provided by a primary therapeutic agent, the apple extract comprises an extract of skin and fruit of *Malus pumila*; the grape extract comprises an extract of seeds of *Vitis vinifera*; the green tea extract comprises an extract of leaves of *Camellia sinensis*; and the olive extract comprises leaves of *Olea europea europaea*.

In one embodiment of the method of enhancing a therapeutic effect provided by a primary therapeutic agent, the apple, grape, green tea, and olive extracts are combined at a weight ratio of about 1:1:1:1.

In one embodiment of the method of enhancing a therapeutic effect provided by a primary therapeutic agent, the apple, grape, green tea, and olive extracts are combined at a weight ratio of about 6:1:3:1.

In one embodiment of the method of enhancing a therapeutic effect provided by a primary therapeutic agent, the method further comprises combining the primary therapeutic agent and the apple, grape, green tea, and olive extracts with at least one secondary therapeutic agent.

In one embodiment of the method of enhancing a therapeutic effect provided by a primary therapeutic agent, wherein the at least one secondary therapeutic agent comprises a member selected from the group consisting of bergamot, mangosteen, berberine, arginine, citrulline, glutamine, zinc, beet, loclo, protein, curcumin, phytosterols, fish oil, CoQ10, vitamins, fiber, inulin, and combinations thereof.

In one embodiment of the method of enhancing a therapeutic effect provided by a primary therapeutic agent, the method further comprises combining the primary therapeutic agent and the apple, grape, green tea, and olive extracts with a blueberry concentrate, a capsicum extract, and a turmeric extract.

In one embodiment of the method of enhancing a therapeutic effect provided by a primary therapeutic agent, the method further comprises combining the primary therapeutic agent, the blueberry concentrate and the apple, grape, green tea, olive, capsicum, and turmeric extracts with a mangosteen fruit extract.

In one embodiment of the method of enhancing a therapeutic effect provided by a primary therapeutic agent, the method further comprises combining the primary therapeutic agent, the blueberry concentrate and the apple, grape, green tea, olive, capsicum, and turmeric extracts with a bergamot extract.

In one embodiment of the method of enhancing a therapeutic effect provided by a primary therapeutic agent, the method further comprises combining the primary therapeutic agent, the blueberry concentrate and the apple, grape, green tea, olive, capsicum, and turmeric extracts with a mangosteen pericarp extract.

In one embodiment of the method of enhancing a therapeutic effect provided by a primary therapeutic agent, the method further comprises combining the primary therapeutic agent, the blueberry concentrate and the apple, grape, green tea, olive, capsicum, and turmeric extracts with mangosteen pericarp extract and bergamot extract.

In one embodiment presented herein is a method of making an activity-enhanced composition for regulating oxidative stress in a subject, comprising: combining apple, grape, green tea, and olive extracts in amounts that provide a greater antioxidant activity than provided by an equivalent amount of any one extract or a sum of the extracts.

In one embodiment of the method of making an activity-enhanced composition for regulating oxidative stress in a subject, the apple, grape, green tea and olive extracts are extracted using an extraction solvent selected from the group consisting of water, ethanol, ethyl acetate, and combinations thereof.

In one embodiment of the method of making an activity-enhanced composition for regulating oxidative stress in a subject, the apple, grape, green tea, and olive extracts are present combined at a weight ratio of about 1:1:1:1.

In one embodiment of the method of making an activity-enhanced composition for regulating oxidative stress in a subject, the apple, grape, green tea, and olive extracts are combined at a weight ratio of about 6:1:3:1.

In one embodiment of the method of making an activity-enhanced composition for regulating oxidative stress in a subject, the method further comprises combining the apple, grape, green tea, and olive extracts with at least one primary or secondary therapeutic agent.

In one embodiment of the method of making an activity-enhanced composition for regulating oxidative stress in a subject, the at least one primary or secondary therapeutic agent comprises a member selected from the group consisting of bergamot, mangosteen, berberine, arginine, citrulline, glutamine, zinc, beet, loclo, protein, curcumin, phytosterols, fish oil, CoQ10, vitamins, fiber, inulin, and combinations thereof.

In one embodiment of the method of making an activity-enhanced composition for regulating oxidative stress in a subject, the method further comprises combining the apple, grape, green tea, and olive extracts with a blueberry concentrate, a capsicum extract, and a turmeric extract.

In one embodiment of the method of making an activity-enhanced composition for regulating oxidative stress in a subject, the method further comprises combining the blueberry concentrate and the apple, grape, green tea, olive, capsicum, and turmeric extracts with a mangosteen fruit extract.

In one embodiment of the method of making an activity-enhanced composition for regulating oxidative stress in a subject, the method further comprises combining the blueberry concentrate and the apple, grape, green tea, olive, capsicum, and turmeric extracts with a bergamot extract.

In one embodiment of the method of making an activity-enhanced composition for regulating oxidative stress in a subject, the method further comprises combining the blueberry concentrate and the apple, grape, green tea, olive, capsicum, and turmeric extracts with a mangosteen pericarp extract.

In one embodiment of the method of making an activity-enhanced composition for regulating oxidative stress in a subject, the method further comprises combining the blueberry concentrate and the apple, grape, green tea, olive, capsicum, and turmeric extracts with mangosteen pericarp extract and bergamot extract.

In one embodiment presented herein is a method of making an activity-enhanced composition for regulating disease-associated protein kinase activity in a subject, comprising: combining apple, grape, green tea, and olive extracts in amounts that provide a greater protein kinase regulating activity than provided by an equivalent amount of any one extract or a sum of the extracts.

In one embodiment of the method of making an activity-enhanced composition for regulating disease-associated protein kinase activity in a subject, the apple, grape, green tea and olive extracts are extracted using an extraction solvent selected from the group consisting of water, ethanol, ethyl acetate, and combinations thereof.

In one embodiment of the method of making an activity-enhanced composition for regulating disease-associated protein kinase activity in a subject, the apple, grape, green tea, and olive extracts are present combined at a weight ratio of about 1:1:1:1.

In one embodiment of the method of making an activity-enhanced composition for regulating disease-associated protein kinase activity in a subject, the apple, grape, green tea, and olive extracts are combined at a weight ratio of about 6:1:3:1.

In one embodiment of the method of making an activity-enhanced composition for regulating disease-associated protein kinase activity in a subject, the method further comprises combining the apple, grape, green tea, and olive extracts with at least one secondary therapeutic agent.

In one embodiment of the method of making an activity-enhanced composition for regulating disease-associated protein kinase activity in a subject, the at least one secondary therapeutic agent comprises a member selected from the group consisting of bergamot, mangosteen, berberine, arginine, citrulline, glutamine, zinc, beet, loclo, protein, curcumin, phytosterols, fish oil, CoQ10, vitamins, fiber, inulin, and combinations thereof.

In one embodiment of the method of making an activity-enhanced composition for regulating disease-associated protein kinase activity in a subject, the method further comprises combining the apple, grape, green tea, and olive extracts with a blueberry concentrate, a capsicum extract, and a turmeric extract.

In one embodiment of the method of making an activity-enhanced composition for regulating disease-associated protein kinase activity in a subject, the method further comprises combining the blueberry concentrate and the apple, grape, green tea, olive, capsicum, and turmeric extracts with a mangosteen fruit extract.

In one embodiment of the method of making an activity-enhanced composition for regulating disease-associated protein kinase activity in a subject, the method further comprises combining the blueberry concentrate and the apple, grape, green tea, olive, capsicum, and turmeric extracts with a bergamot extract.

In one embodiment of the method of making an activity-enhanced composition for regulating disease-associated protein kinase activity in a subject, the method further comprises combining the blueberry concentrate and the apple, grape, green tea, olive, capsicum, and turmeric extracts with a mangosteen pericarp extract.

In one embodiment of the method of making an activity-enhanced composition for regulating disease-associated protein kinase activity in a subject, the method further comprises combining the blueberry concentrate and the apple, grape, green tea, olive, capsicum, and turmeric extracts with mangosteen pericarp extract and bergamot extract.

In one embodiment presented herein is a method of making a therapeutic composition comprising: providing a primary therapeutic agent; and combining apple, grape, green tea, and olive extracts with the primary therapeutic agent in amounts that increase a therapeutic effect of the primary therapeutic agent more than an increase in therapeutic effect provided by an equivalent amount of any one of the extracts alone.

In one embodiment of the method of making a therapeutic composition, the method further comprises first extracting the apple, grape, green tea and olive extracts using an extraction solvent selected from the group consisting of water, ethanol, ethyl acetate, and combinations thereof.

In one embodiment of the method of making a therapeutic composition, the apple, grape, green tea, and olive extracts are present combined at a weight ratio of about 1:1:1:1.

In one embodiment of the method of making a therapeutic composition, the apple, grape, green tea, and olive extracts are combined at a weight ratio of about 6:1:3:1.

In one embodiment of the method of making a therapeutic composition, the method further comprises combining the apple, grape, green tea, and olive extracts with at least one secondary therapeutic agent.

In one embodiment of the method of making a therapeutic composition, the at least one secondary therapeutic agent comprises a member selected from the group consisting of bergamot, mangosteen, berberine, arginine, citrulline, glutamine, zinc, beet, loclo, protein, curcumin, phytosterols, fish oil, CoQ10, vitamins, fiber, inulin, and combinations thereof.

In one embodiment of the method of making a therapeutic composition, the method further comprises combining the primary therapeutic agent, the apple, grape, green tea, and olive extracts with a blueberry concentrate, a capsicum extract, and a turmeric extract.

In one embodiment of the method of making a therapeutic composition, the method further comprises combining the primary therapeutic agent, the blueberry concentrate, and the apple, grape, green tea, olive, capsicum, and turmeric extracts with a mangosteen fruit extract.

In one embodiment of the method of making a therapeutic composition, the method further comprises combining the primary therapeutic agent, the blueberry concentrate, and the apple, grape, green tea, olive, capsicum, and turmeric extracts with a bergamot extract.

In one embodiment of the method of making a therapeutic composition, the method further comprises combining the primary therapeutic agent, the blueberry concentrate, and the apple, grape, green tea, olive, capsicum, and turmeric extracts with a mangosteen pericarp extract.

In one embodiment of the method of making a therapeutic composition, the method further comprises combining the primary therapeutic agent, the blueberry concentrate, and the apple, grape, green tea, olive, capsicum, and turmeric extracts with mangosteen pericarp extract and bergamot extract.

Embodiments of the present disclosure will be described with reference to the following examples, which are provided for illustrative purposes only and should not be used to limit the scope of or construe the invention.

EXAMPLES

Example 1

A Ten-Component Phytocomplex ("PC10") Exhibits Synergy in Oxygen Radical Absorbance Capacity A 10-component phytocomplex (PC10) that exhibits synergy in its ability to absorb oxygen radicals using the oxygen radical absorbance capacity (ORAC) assay is prepared as set forth below.

Chemicals—All chemicals were purchased from standard chemical suppliers (e.g. Sigma, St. Louis, Mo.) and were of the highest purity commercially available. Reagents used included 75 mM potassium phosphate (KH2PO4) (pH=7.4); 0.64M AAPH (2'2'-Azobis (2-amidino-propane)dihydrochloride);10 mM Trolox (6-Hydroxy-2,5,7,8-tetramethyl-chroman-2-carboxylic acid); 4.4 x10-6 M stock fluorescein, sodium salt; and 1:1 acetone/water.

PC10 Materials—Ten commercial samples apple fruit extract (R11309), bergamot fruit extract (R 13216), blueberry fruit concentrate (R10990), capsicum fruit (R11505), grape seed extract (R13545), grape skin extract (R13555), green tea leaf extract (R13568), mangosteen pericarp extract (R26699), olive leaf extract (R15020), and turmeric root & rhizome extract (R17065) were tested individually and in various combinations for their oxygen radical scavenging activity.

Sample preparation—Samples were ground to fine powder and mixed thoroughly. Fifty mg (accurate to 0.1 mg) of sample was transferred into a 35 ml centrifuge tube and mixed with 25 ml of acetone/water (50:50, v/v) extraction solution. Samples were then sonicated for 60 min (shaken from 20 to 40 min) and centrifuged at 3.5K rpm for 10 min.

The PC10 material was formulated by combining apple fruit extract, bergamot fruit extract, blueberry fruit concentrate, capsicum fruit, grape seed extract, grape skin extract, green tea leaf extract, mangosteen pericarp extract, olive leaf extract, and turmeric root & rhizome extract in a number of ratios beginning with 1:1:1:1:1:1:1:1:1:1 and increasing or decreasing the relative amount of a component based upon ORAC activity and cost of ingredient.

Assay methodology—Cuvettes for blank, standard and samples were placed in dry bath at 28±1° C. and 100 µL 8.8×10-8 M fluorescein and 2.50 ml buffer were added into each cuvette and 50 µL buffer was added for the blank. Fifty µL sample solution was added to the sample cuvette. Cuvettes were capped and mixed briefly. Cuvettes were placed into the holder of an RF-150 Spectrofluorophotometer and the initial florescence was recorded as f0. One-hundred µL AAPH was added to each cuvette at time t=0. The cuvette was capped and vortexed briefly. Fluorescence (RFU) was measured at five minute intervals until the fluorescence decay ceased or the value of fluorescence was <5% of the initial fluorescence reading. RFU were recorded as f1, f2, etc. Fluorescence decay was complete in 60 min.

Calculations—The median inhibitory concentration ($IC_{50}$) for oxygen radical scavenging activity in this example was calculated by interpolating the concentration required for the inhibition of the fluorescence decay by 50 percent within 20 minutes. Synergy of test components was then quantified using the combination index (CI) parameter. This parameter defines only the additive effect rather than synergism or antagonism. Synergy, however, was defined as a more than expected additive effect (CI>1), and antagonism as a less than expected additive effect (CI<1) as described below.

Expected median inhibitory concentrations of any multi-component combination were estimated using the relationship:

$$[1/\text{Expected IC}_{50}]=[\text{Fa}/\text{IC}_{50}A]+[\text{Fb}/\text{IC}_{50}]+\ldots+[\text{Fn}/\text{IC}_{50}N] \text{ and } \text{Fa}+\text{Fb}+\ldots+\text{Fn}=1$$

where Fa=mole fraction of component A in the combination and Fn=the mole fraction of the $n^{th}$ component combination and $IC_{50}$=the observed $IC_{50}$ of the component A. The CI was then calculated thusly, CI=Expected $[IC_{50}]$/Observed $[IC_{50}]$. Using the designation of CI=1 as the additive effect, for mutually exclusive compounds that have the same mode of action or for mutually non-exclusive drugs that have totally independent modes of action the following relationships are defined: CI<1,=1, and >1 indicating antagonism, additivity and synergy, respectively.

Results—As seen in Table 1, the observed $IC_{50}$ of the ten-component phytocomplex was 18.6 mg/L, while the calculated, expected $IC_{50}$ value was 26.5 mg/L resulting in a CI=1.43. This level of difference was unexpected and constitutes a novel, unexpected finding for the PC10 formulation oxygen radical scavenging activity.

TABLE 1

Determining Combination Index for Oxygen Radical Absorbance Capacity of an Ten-component Phytocomplex (PC10)

| Test Material | Observed $IC_{50}$ [mg/L] | Relative Amount [F] | Fn/[$IC_{50}$] [μg/mL]$^{-1}$ |
|---|---|---|---|
| Apple fruit† | 6.8 | 0.085 | 0.0124 |
| Bergamot fruit† | 46.3 | 0.704 | 0.0152 |
| Blueberry fruit* | 1,283 | 0.014 | 0.000011 |
| Capsicum fruit† | 887 | 0.014 | 0.000016 |
| Grape seed* | 10.2 | 0.014 | 0.0014 |
| Grape skin† | 373 | 0.014 | 0.000038 |
| Green tea leaf† | 67.4 | 0.042 | 0.00063 |
| Mangosteen pericarp† | 49.6 | 0.014 | 0.00028 |
| Olive leaf† | 101 | 0.014 | 0.000140 |
| Turmeric root† | 11.2 | 0.085 | 0.0076 |
| Phytocomplex(10)** | 18.6 | 1.000 | 0.0377 |

†extract/
*concentrate/
**Phytocomplex (10) contains relative amounts of each of the ten test ingredients; Expected IC50 for PC10 = 1/[0.0377] = 26.5 μg/mL.

Conclusion—The ten-component phytocomplex (PC10) in the ratios of about 6:50:1:1:1:1:3:1:1:6 exhibited an unexpected increase of 1.42-times the oxygen radical scavenging activity relative to the sum of its individual components.

Example 2

An Eight-Component Phytocomplex Exhibits Synergy in Oxygen Radical Absorbance Capacity A nine-component phytocomplex relative to the sum of the expected contributions of its components in the standard ORAC Assay is prepared as set forth below.

Chemicals—All chemicals used in this example were those previously described in Example 1.

PC8 Materials—With the exclusion of bergamot and mangosteen pericarp, the test materials used in this example included those previously described for Example 1.

Assay methodology—The methodology was generally as described in Example 1 with the exception that assays were performed in 96-well microplates fluorimeter at wavelength 493 nm (excitation)/520 nm (emission) every 2 minute for 20 minutes.

Calculations—The median inhibitory concentration (IC50) for oxygen radical scavenging activity was calculated using CalcuSyn (BIOSOFT, Ferguson, Mo.). This statistical package performs multiple drug dose-effect calculations using the median effect methods described by T-C Chou and P. Talaly [(1984) Quantitative analysis of dose-effect relationships: the combined effects of multiple drugs or enzyme inhibitors. Adv Enzyme Regul 22, 27-55.] hereby incorporated by reference.

Briefly, the analysis correlates the "Dose" and the "Effect" in the simplest possible form: fa/fu=(C/Cm)m, where C is the concentration or dose of the compound and Cm is the median-effective dose signifying the potency. Cm is determined from the x-intercept of the median-effect plot. The fraction affected by the concentration of the test material is fa and the fraction unaffected by the concentration is fu (fu=1−fa). The exponent m is the parameter signifying the sigmoidicity or shape of the dose-effect curve; it is estimated by the slope of the median-effect plot.

The median-effect plot is a graph of x=log(C) vs y=log (fa/fu) and is based on the logarithmic form of Chou's median-effect equation. The goodness of fit for the data to the median-effect equation is represented by the linear correlation coefficient r of the median-effect plot. Usually, the experimental data from enzyme or receptor systems have an r >0.96, from tissue culture an r>0.90 and from animal systems r>0.85.

Synergy of test components was quantified using the combination index (CI) parameter as defined in Example 1.

Expected median inhibitory concentrations of any multi-component combination were estimated using the relationship:

$$[1/\text{Expected IC}_{50}]=[\text{Fa}/\text{IC}_{50A}]+[\text{Fb}/\text{IC}_{50}]+\ldots+[\text{Fn}/\text{IC}_{50}N] \text{ and and } \text{Fa}+\text{Fb}+\ldots+\text{Fn}=1$$

where Fa=mole fraction of component A in the combination and Fn=the mole fraction of the $n^{th}$ component combination and $IC_{50A}$=the observed $IC_{50}$ of the component A. The CI was then calculated thusly, CI=Expected $[IC_{50}]$/Observed $[IC_{50}]$.

Using the designation of CI=1 as the additive effect, we obtain for mutually exclusive compounds that have the same mode of action or for mutually non-exclusive drugs that have totally independent modes of action the following relationships: CI<1, =1, and >1 indicating antagonism, additivity and synergy, respectively.

Results—The median inhibitory concentration ($IC_{50}$) of PC8 was 0.0350 μg/mL, while the calculated, expected $IC_{50}$ was 0.0436 μg/mL resulting in a CI=1.31. Thus, PC8 synergistically produced 1.3-times the oxygen radical scavenging activity than expected from the sum of the activity of its components.

TABLE 2

Determining Combination Index for Oxygen Radical Absorbance Capacity of an Eight-component Phytocomplex (PC8)

| Test Material | Observed $IC_{50}$ [μg/mL] | Relative Amount [F] | Fn/[$IC_{50}$] [μg/mL]$^{-1}$ |
|---|---|---|---|
| Apple fruit† | 0.02 | 0.300 | 15 |
| Blueberry fruit* | 25.55 | 0.050 | 0.002 |
| Capsicum fruit† | 111 | 0.050 | 0.000450 |
| Grape seed* | 0.0413 | 0.050 | 1.212 |

TABLE 2-continued

Determining Combination Index for Oxygen Radical Absorbance Capacity of an Eight-component Phytocomplex (PC8)

| Test Material | Observed $IC_{50}$ [μg/mL] | Relative Amount [F] | $Fn/[IC_{50}]$ [μg/mL]$^{-1}$ |
|---|---|---|---|
| Grape skin† | 0.233 | 0.050 | 0.215 |
| Green tea leaf† | 0.04 | 0.150 | 3.75 |
| Olive leaf† | 0.08 | 0.050 | 0.625 |
| Turmeric root† | 0.43 | 0.300 | 0.698 |
| Phytocomplex(PC8)** | 0.0350 | 1.000 | 21.58 |

†extract/
*concentrate/
**Phytocomplex PC8 contains relative amounts [F] of each of the eight test materials; Expected $IC_{50}$ for PC8 = 1/[21.58] = 0.046 μg/mL.

Conclusion—With CI=1.31, PC8 unexpectedly produced 1.31-times the oxygen radical scavenging activity than expected from the sum of its components.

Example 3

A Nine-Component Phytocomplex Containing Mangosteen Fruit ("PC9f") Exhibits Synergy in Oxygen Radical Absorbance Capacity A nine-component phytocomplex relative to the sum of the expected contributions of the relative components in the standard ORAC Assay is prepared as set forth below.

All Chemicals, Methods and Calculations were performed as described in Example 2.

PC9f Material—The test material used in this example contained the ingredients and relative amounts listed in Table 3.

Results—The $IC_{50}$ of PC9f was 0.0410 μg/mL, while the calculated, expected $IC_{50}$ was 0.0.049 μg/mL resulting in a CI=1.20. Thus, PC9f synergistically produced 1.20-times the oxygen radical scavenging activity than expected from the activity of the sum of its components.

TABLE 3

Determining Combination Index for Oxygen Radical Absorbance Capacity of a Nine-component Phytocomplex Containing Mangosteen Fruit (PC9f)

| Test Material | Observed $IC_{50}$ [μg/mL] | Relative Amount [F] | $Fn/[IC_{50}]$ [μg/mL]$^{-1}$ |
|---|---|---|---|
| Apple fruit† | 0.02 | 0.286 | 14.3 |
| Blueberry fruit* | 25.55 | 0.0476 | 0.002 |
| Capsicum fruit† | 111 | 0.0476 | 0.000432 |
| Grape seed* | 0.0413 | 0.0476 | 1.19 |
| Grape skin† | 0.233 | 0.0476 | 0.238 |
| Green tea leaf† | 0.04 | 0.1429 | 3.573 |
| Mangosteen fruit† | 3.99 | 0.0476 | 0.012 |
| Olive leaf† | 0.08 | 0.0476 | 0.595 |
| Turmeric root & rhizome† | 0.43 | 0.286 | 0.664 |
| Phytocomplex (PC9f) | 0.0410 | 1.000 | 20.56 |

†extract/
*concentrate/
**Phytocomplex PC9f contains relative amounts [F] of each of the nine test materials; Expected $IC_{50}$ for PC9f = 1/[20.56] = 0.049 μg/mL.

Conclusion—With CI=1.20, PC9f unexpectedly produced 1.2-times the oxygen radical scavenging activity than expected from the sum of its components.

Example 4

An Eight-Component Phytocomplex (PC8) Exhibits Synergy in Free Radical Quenching A eight-component phytocomplex relative to the sum of the expected contributions of its components to scavenge free radicals is prepared as set forth below.

Methodology—The 2,2-Diphenyl-1-picrylhydrazyl (DPPH) assay was used to assess scavenging of free radicals by the test materials. This assay is based on the theory that a hydrogen donor is an antioxidant. The assay measures compounds that are radical scavengers. The stable free radical DPPH* accepts hydrogen from an antioxidant. The antioxidant effect is proportional to the disappearance of DPPH$^-$ in test samples. The procedure as described by Dudonne was used with the modification that the assay was conducted in 96-well, microtiter plates [Dudonne, S., Vitrac, X., Coutiere, P., Woillez, M., and Merillon, J. M. (2009) Comparative Study of Antioxidant Properties and Total Phenolic Content of 30 Plant Extracts of Industrial Interest Using DPPH, ABTS, FRAP, SOD, and ORAC Assays, J Agric Food Chem 57, 1768-1774].

PC8 Material—The test material used in this study were as described in Example 2 and Tables 2 and 4.

Calculations—Calculations were performed as described in Example 2.

Results—The median inhibitory concentration ($IC_{50}$) of PC8 was 15.6 μg/mL, while the calculated, expected $IC_{50}$ was 17.9 μg/mL resulting in a CI=1.15. Thus, PC8 synergistically produced 1.2-times the free radical quenching activity of the sum of its components.

TABLE 4

Determining Combination Index for Free Radical Quenching Capacity of an Eight-component Phytocomplex (PC8)

| Test Material | Observed $IC_{50}$ [μg/mL] | Relative Amount [F] | $Fn/[IC_{50}]$ [μg/mL]$^{-1}$ |
|---|---|---|---|
| Apple fruit† | 14.1 | 0.300 | 0.0213 |
| Blueberry fruit* | 2713 | 0.050 | 0.0000184 |
| Capsicum fruit† | 7225 | 0.050 | 0.00000692 |
| Grape seed* | 5.52 | 0.050 | 0.00906 |
| Grape skin† | 107 | 0.050 | 0.000469 |
| Green tea leaf† | 6.89 | 0.150 | 0.0218 |
| Olive leaf† | 50.3 | 0.050 | 0.000993 |
| Turmeric root† | 137 | 0.300 | 0.00218 |
| Phytocomplex(PC8)** | 15.6 | 1.000 | 0.0558 |

†extract/
*concentrate/
**Phytocomplex PC8 contains relative amounts [F] of each of the eight test materials; Expected $IC_{50}$ for PC8 = 1/[0.0558] = 17.92 μg/mL.

Conclusion—With CI=1.15, PC8 unexpectedly produced 1.2-times the free radical quenching activity than the sum of its components.

Example 5

An Nine-Component Phytocomplex Containing Mangosteen Fruit ("PC9f") Exhibits Synergy in Free Radical Quenching A nine-component phytocomplex relative to the sum of the expected contribution of its components to scavenge free radicals is prepared as set forth below.

All Chemicals and Calculations were as described in Example 2 and the Methods were as previously presented in Example 4.

PC9f Material—the test material used in this example contained the ingredients and relative amounts listed in Tables 3 and 5.

Results—The $IC_{50}$ of PC9f was 16.2 µg/mL, while the calculated, expected $IC_{50}$ was 18.8 µg/mL resulting in a CI=1.16. Thus, PC9f synergistically produced 1.8-times the oxygen radical scavenging activity than expected from the activity of the sum of its components.

TABLE 5

Determining Combination Index for Free Radical Quenching Capacity of a Nine-component Phytocomplex Containing Mangosteen Fruit (PC9f)

| Test Material | Observed $IC_{50}$ [µg/mL] | Relative Amount [F] | Fn/[$IC_{50}$] [µg/mL]$^{-1}$ |
|---|---|---|---|
| Apple fruit† | 14.1 | 0.286 | 0.0202664 |
| Blueberry fruit* | 2713 | 0.048 | 0.0000175 |
| *Capsicum* fruit† | 7225 | 0.048 | 0.00000659 |
| Grape seed† | 5.52 | 0.048 | 0.0086269 |
| Grape skin† | 106.6 | 0.048 | 0.0004465 |
| Green tea leaf† | 6.89 | 0.143 | 0.0207460 |
| Mangosteen fruit† | 3527 | 0.048 | 0.0000135 |
| Olive leaf† | 50.3 | 0.048 | 0.0009455 |
| Turmeric root & rhizome† | 137 | 0.286 | 0.0020804 |
| Phytocomplex (PC9f) | 16.2 | 1.000 | 0.0531 |

†extract/
*concentrate/
**Phytocomplex PC9f contains relative amounts [F] of each of the nine test materials; Expected $IC_{50}$ for PC9f = 1/[0.0531] = 18.8 µg/mL.

Conclusion—With CI=1.16, PC9f unexpectedly produced 1.2-times the oxygen radical scavenging activity than expected from the sum of its components.

Example 6

A Nine-Component Phytocomplex Containing Mangosteen Pericarp ("PC9p") Exhibits Synergy in Free Radical Quenching A nine-component phytocomplex relative to the sum of the expected contribution of its components to scavenge free radicals is prepared as set forth below.

Chemicals and Methods were as previously presented in Example 4, while Calculations were as described in Example 2.

PC9p Material—the test material used in this example contained the ingredients and relative amounts described in Table 6.

TABLE 6

Determining Combination Index for Free Radical Quenching Capacity of a Nine-component Phytocomplex Containing Mangosteen Pericarp (PC9p)

| Test Material | Observed $IC_{50}$ [µg/mL] | Relative Amount [F] | Fn/[$IC_{50}$] [µg/mL]$^{-1}$ |
|---|---|---|---|
| Apple fruit† | 14.1 | 0.286 | 0.0203 |
| Blueberry fruit* | 2713 | 0.0476 | 0.0000175 |
| *Capsicum* fruit† | 7225 | 0.0476 | 0.0000066 |
| Grape seed† | 5.52 | 0.0476 | 0.0086 |
| Grape skin† | 106.6 | 0.0476 | 0.000447 |
| Green tea leaf† | 6.89 | 0.143 | 0.0207 |

TABLE 6-continued

Determining Combination Index for Free Radical Quenching Capacity of a Nine-component Phytocomplex Containing Mangosteen Pericarp (PC9p)

| Test Material | Observed $IC_{50}$ [µg/mL] | Relative Amount [F] | Fn/[$IC_{50}$] [µg/mL]$^{-1}$ |
|---|---|---|---|
| Mangosteen pericarp† | 26.7 | 0.0476 | 0.00178 |
| Olive leaf† | 50.3 | 0.0476 | 0.000945 |
| Turmeric root & rhizome† | 137 | 0.286 | 0.0021 |
| Phytocomplex (PC9p) | 13.4 | 1.000 | 0.0549 |

†extract/
*concentrate/
**Phytocomplex PC9p contains relative amounts [F] of each of the nine test materials; Expected $IC_{50}$ for PC9p = 1/[0.0549] = 18.2 µg/mL.

Results—The $IC_{50}$ of PC9p was 013.4 µg/mL, while the calculated, expected $IC_{50}$ was 18.2 µg/mL resulting in a CI=1.36. Thus, PC9p synergistically produced 1.4-times the free radical quenching activity than expected from the activity of the sum of its components.

Conclusion—With CI=1.36, PC9p unexpectedly produced 1.4-times the free radical quenching activity than the sum of its components.

Example 7

A Nine-Component Phytocomplex ("PC9b") Exhibits Synergy in Peroxynitrite (ONOO$^-$) Scavenging Capacity The potential for synergy of a nine-component phytocomplex relative to the sum of the expected contributions of its components in scavenging peroxynitrite is prepared as set forth below.

Methodology—Peroxynitrite (ONOO$^-$) scavenging capacity was measured according to the procedure described by Kim et al. [Kim, J. Y., Kim, H. S., Kang, H. S., Choi, J. S., Yokozawa, T., and Chung, H. Y. (2008) Antioxidant potential of dimethyl lithospermate isolated from Salvia miltiorrhiza (red sage) against peroxynitrite, J Med Food 11, 21-28] with the modification that assays were conducted in 96-well microtiter plates instead of cuvettes. Calculations were as described in Example 2.

PC9b Material—In addition to the bergamot extract as described in Example 1, the remaining test material used in this study were as described in Example 2 and Tables 2 and 4 as PC8. The $IC_{50}$ of PC9b was 0.974 µg/mL, while the calculated, expected $IC_{50}$ was 1.67 µg/mL resulting in a CI=1.71. Thus, PC9b synergistically produced 1.7-times the peroxynitrite-scavenging capacity than expected from the sum of its components.

TABLE 7

Determining Combination Index for Peroxynitrite (ONOO$^-$) Scavenging Capacity of a Nine-component Phytocomplex (PC9b) Containing Bergamot

| Test Material | Observed $IC_{50}$ [µg/mL] | Relative Amount [F] | Fn/[$IC_{50}$] [µg/mL]$^{-1}$ |
|---|---|---|---|
| Apple fruit† | 0.875 | 0.0857 | 0.0979 |
| Bergamot | 3.34 | 0.714 | 0.214 |
| Blueberry fruit* | 35.7 | 0.0143 | 0.000401 |
| *Capsicum* fruit† | 31.0 | 0.0143 | 0.000461 |
| Grape seed* | 0.472 | 0.0143 | 0.0303 |
| Grape skin† | 3.11 | 0.0143 | 0.00460 |
| Green tea leaf† | 0.185 | 0.0429 | 0.232 |

TABLE 7-continued

Determining Combination Index for Peroxynitrite (ONOO$^-$) Scavenging Capacity of a Nine-component Phytocomplex (PC9b) Containing Bergamot

| Test Material | Observed IC$_{50}$ [µg/mL] | Relative Amount [F] | Fn/[IC$_{50}$] [µg/mL]$^{-1}$ |
|---|---|---|---|
| Olive leaf† | 1.17 | 0.0143 | 0.0122 |
| Turmeric root† | 10.3 | 0.0857 | 0.00834 |
| Phytocomplex(PC9b)** | 0.974 | 1.000 | 0.600 |

†extract/
*concentrate/
**Phytocomplex PC9b contains relative amounts [F] of each of the nine test materials; Expected IC$_{50}$ for PC9b = 1/[0.600] = 1.67 µg/mL.

Conclusion—With CI=1.71, PC9b unexpectedly produced 1.7-times the peroxynitrite-scavenging capacity than expected from the sum of its components.

Example 8

A Nine-Component Phytocomplex ("PC9f") Exhibits Synergy in Peroxynitrite (ONOO$^-$) Scavenging Capacity The potential for synergy of a novel, nine-component phytocomplex containing mangosteen fruit relative to the sum of the expected contributions of its components in scavenging peroxynitrite was evaluated.

Methodology—Methods and Calculations were as previously described in Example 7, while Calculations were as described in Example 2.

PC9f Material—PC9f and components as described in Example 3 and Tables 3 and 8 were the test materials in this example. The IC$_{50}$ of PC9f was 0.486 µg/mL, while the calculated, expected IC$_{50}$ was 0.777 µg/mL resulting in a CI=1.60. Thus, PC9f synergistically produced 1.6-times the peroxynitrite-scavenging capacity than expected from the sum of its components.

TABLE 8

Determining Combination Index for Peroxynitrite (ONOO$^-$) Scavenging Capacity of a Nine-component Phytocomplex (PC9f)

| Test Material | Observed IC$_{50}$ [µg/mL] | Relative Amount [F] | Fn/[IC$_{50}$] [µg/mL]$^{-1}$ |
|---|---|---|---|
| Apple fruit† | 0.875 | 0.286 | 0.326 |
| Blueberry fruit* | 35.7 | 0.0476 | 0.001 |
| Capsicum fruit† | 31.0 | 0.0476 | 0.002 |
| Grape seed† | 0.472 | 0.0476 | 0.101 |
| Grape skin† | 3.11 | 0.0476 | 0.015 |
| Green tea leaf† | 0.185 | 0.143 | 0.773 |
| Mangosteen fruit† | 68.3 | 0.0476 | 0.001 |
| Olive leaf† | 1.17 | 0.0476 | 0.041 |
| Turmeric root & rhizome† | 10.3 | 0.286 | 0.028 |
| Phytocomplex (PC9f) | 0.486 | 1.000 | 1.29 |

†extract/
*concentrate/
**Phytocomplex PC9f contains relative amounts [F] of each of the nine test materials; Expected IC$_{50}$ for PC9f = 1/[1.29] = 0.777 µg/mL.

Conclusion—With CI=1.60, PC9f unexpectedly produced 1.6-times the peroxynitrite-scavenging capacity than expected from the sum of its components.

Example 9

A Nine-Component Phytocomplex (PC9f) Plus Bergamot Exhibits Synergy in Peroxynitrite (ONOO$^-$) Scavenging Capacity The potential for synergy of a novel, nine-component phytocomplex containing mangosteen fruit and bergamot relative to the sum of the expected contributions of its components in scavenging peroxynitrite was evaluated.

Methodology—Methods and Calculations were as previously described in Examples 7 and 2, respectively.

PC9f Plus Bergamot Material—PC9f and components as described in Example 3 and Tables 3 and 9 were the test materials in this example along with the bergamot extract as described in Example 1. The IC$_{50}$ of PC9f plus bergamot fruit extract was 0.556 µg/mL, while the calculated, expected IC$_{50}$ was 1.69 µg/mL resulting in a CI=3.04. Thus, PC9f plus bergamot fruit extract synergistically produced 3.0-times the peroxynitrite-scavenging capacity than expected from the sum of its components.

TABLE 9

Determining Combination Index for Peroxynitrite (ONOO$^-$) Scavenging Capacity of a Nine-component Phytocomplex (PC9f) plus Bergamot Fruit Extract

| Test Material | Observed IC$_{50}$ [µg/mL] | Relative Amount [F] | Fn/[IC$_{50}$] [µg/mL]$^{-1}$ |
|---|---|---|---|
| Apple fruit† | 0.875 | 0.0845 | 0.097 |
| Bergamot fruit† | 3.34 | 0.7042 | 0.211 |
| Blueberry fruit* | 35.7 | 0.0141 | 0.000395 |
| Capsicum fruit† | 31.0 | 0.0141 | 0.000455 |
| Grape seed† | 0.472 | 0.0141 | 0.0299 |
| Grape skin† | 3.11 | 0.0141 | 0.00454 |
| Green tea leaf† | 0.185 | 0.0423 | 0.229 |
| Mangosteen fruit† | 68.3 | 0.0141 | 0.000206 |
| Olive leaf† | 1.17 | 0.0141 | 0.0121 |
| Turmeric root & rhisome† | 10.3 | 0.0845 | 0.00822 |
| Phytocomplex (PC9f) + Bergamot | 0.556 | 1.000 | 0.592 |

†extract/
*concentrate/
**Phytocomplex PC9f + Bergamot contains relative amounts [F] of each of the nine test materials; Expected IC$_{50}$ for PC9f + Bergamot = 1/[0.592] = 1.69 µg/mL.

Conclusion—With CI=3.04, PC9f+bergamot fruit extract unexpectedly produced 3.0-times the peroxynitrite-scavenging capacity than expected from the sum of its components

Example 10

A Nine-Component Phytocomplex (PC9p) Exhibits Synergy in Peroxynitrite (ONOO$^-$) Scavenging Capacity The potential for synergy of a novel, nine-component phytocomplex containing mangosteen pericarp (PC9p) relative to the sum of the expected contributions of its components in scavenging peroxynitrite was evaluated.

Methodology—Methods and Calculations were as previously described in Examples 7 and 2, respectively.

PC9p Material—PC9p and components as described in Table 10 were the test materials in this example. The IC$_{50}$ of PC0p was 0.523 µg/mL, while the calculated, expected IC$_{50}$ was 0.768 µg/mL resulting in a CI=1.47. Thus, PC9p synergistically produced 1.5-times the peroxynitrite-scavenging capacity than expected from the sum of its components.

TABLE 10

Determining Combination Index for Peroxynitrite (ONOO⁻) Scavenging Capacity of a Nine-component Phytocomplex (PC9p)

| Test Material | Observed $IC_{50}$ [µg/mL] | Relative Amount [F] | $Fn/[IC_{50}]$ [µg/mL]$^{-1}$ |
|---|---|---|---|
| Apple fruit† | 0.875 | 0.286 | 0.326 |
| Blueberry fruit* | 35.7 | 0.048 | 0.00133 |
| *Capsicum* fruit† | 31.0 | 0.048 | 0.00154 |
| Grape seed† | 0.472 | 0.048 | 0.101 |
| Grape skin† | 3.11 | 0.048 | 0.0153 |
| Green tea leaf† | 0.185 | 0.143 | 0.773 |
| Mangosteen pericarp† | 3.26 | 0.048 | 0.0146 |
| Olive leaf† | 1.17 | 0.048 | 0.0408 |
| Turmeric root & rhizome† | 10.3 | 0.286 | 0.0278 |
| Phytocomplex (PC9p) | 0.523 | 1.00 | 1.30 |

†extract/
*concentrate/
**Phytocomplex PC9p + Bergamot contains relative amounts [F] of each of the nine test materials; Expected $IC_{50}$ for PC9p + Bergamot = 1/[1.30] = 0.768 µg/mL.

Conclusion—With CI=1.47, PC9p unexpectedly produced 1.5-times the peroxynitrite-scavenging capacity than expected from the sum of its components.

Example 11

A Ten-Component Phytocomplex (PC10) Exhibits Synergy in Peroxynitrite (ONOO⁻) Scavenging Capacity The potential for synergy of a novel, ten-component phytocomplex (PC10) relative to the sum of the expected contributions of its components in scavenging peroxynitrite was evaluated.

Methodology—Methods and Calculations were as previously described in Examples 7 and 2, respectively.

PC10 Material—PC10 and components as described in Example 1 and Table 1 were the test materials in this example.

Conclusion—The $IC_{50}$ of PC10 was 1.02 µg/mL, while the calculated, expected $IC_{50}$ was 1.68 µg/mL resulting in a CI=1.64. Thus, PC10 synergistically produced 1.6-times the peroxynitrite-scavenging capacity than expected from the sum of its components.

TABLE 11

Determining Combination Index for Peroxynitrite (ONOO⁻) Scavenging Capacity of a Ten-component Phytocomplex (PC10)

| Test Material | Observed $IC_{50}$ [µg/mL] | Relative Amount [F] | $Fn/[IC_{50}]$ [µg/mL]$^{-1}$ |
|---|---|---|---|
| Apple fruit† | 0.875 | 0.085 | 0.0965 |
| Bergamot fruit† | 3.34 | 0.704 | 0.211 |
| Blueberry fruit* | 35.7 | 0.0141 | 0.000395 |
| *Capsicum* fruit† | 31.0 | 0.0141 | 0.000455 |
| Grape seed† | 0.472 | 0.0141 | 0.0299 |
| Grape skin† | 3.11 | 0.0141 | 0.00454 |
| Green tea leaf† | 0.185 | 0.0423 | 0.229 |
| Mangosteen pericarp† | 3.26 | 0.0141 | 0.00432 |
| Olive leaf† | 1.17 | 0.0141 | 0.0121 |
| Turmeric root & rhizome† | 10.3 | 0.0845 | 0.00822 |
| Phytocomplex (PC10) | 1.02 | 1.00 | 0.596 |

†extract/
*concentrate/
**Phytocomplex PC10 contains relative amounts [F] of each of the ten test materials; Expected $IC_{50}$ for PC10 = 1/[0.596] = 1.68 µg/mL.

Conclusion—With CI=1.64, PC10 unexpectedly produced 1.6-times the peroxynitrite-scavenging capacity than expected from the sum of its components

Example 12

Two Formulations of a Four-component Phytocomplex (PC4) Exhibit Synergy in Peroxynitrite (ONOO⁻) Scavenging Capacity The potential for synergy of a novel, four-component phytocomplex (PC4) relative to the sum of the expected contributions of its components in scavenging peroxynitrite when tested at two formulations was evaluated.

Methodology—Methods and Calculations were as previously described in Examples 7 and 2, respectively.

PC4 Material—PC4 consisted of components listed in Tables 12 and 13 and as described in Example 1. Relative amounts of the individual four components were 1:1:1:1=PC4.1 (Table 13) and 6:3:1:1=PC4.2.

Conclusion—The $IC_{50}$ of PC4.1 was 0.216 µg/mL, while the calculated, expected $IC_{50}$ was 0.420 µg/mL resulting in a CI=1.95. Thus, PC4.1 synergistically produced 2.0-times the peroxynitrite-scavenging capacity than expected from the sum of its components.

TABLE 12

Determining Combination Index for Peroxynitrite (ONOO⁻) Scavenging Capacity of a Four-component Phytocomplex (PC4.1)

| Test Material | Observed $IC_{50}$ [µg/mL] | Relative Amount [F] | $Fn/[IC_{50}]$ [µg/mL]$^{-1}$ |
|---|---|---|---|
| Apple fruit† | 0.875 | 0.250 | 0.286 |
| Grape seed† | 0.472 | 0.250 | 0.530 |
| Green tea leaf† | 0.185 | 0.250 | 1.352 |
| Olive leaf† | 1.17 | 0.250 | 0.214 |
| Phytocomplex (PC4.1) | 0.216 | 1.00 | 2.382 |

†extract/
*concentrate/
**Phytocomplex PC4.1 contains relative amounts [F] of each of the four test materials; Expected $IC_{50}$ for PC4.1 = 1/[2.382] = 0.420 µg/mL.

Conclusion—With CI=1.95, PC4.1 unexpectedly produced 2.0-times the peroxynitrite-scavenging capacity than expected from the sum of its components

TABLE 13

Determining Combination Index for Peroxynitrite (ONOO⁻) Scavenging Capacity of a Four-component Phytocomplex (PC4.2)

| Test Material | Observed $IC_{50}$ [µg/mL] | Relative Amount [F] | $Fn/[IC_{50}]$ [µg/mL]$^{-1}$ |
|---|---|---|---|
| Apple fruit† | 0.875 | 0.545 | 0.623 |
| Grape seed† | 0.472 | 0.0909 | 0.193 |
| Green tea leaf† | 0.185 | 0.273 | 1.475 |
| Olive leaf† | 1.17 | 0.0909 | 0.078 |
| Phytocomplex (PC4.2) | 0.201 | 1.000 | 2.369 |

†extract/
*concentrate/
**Phytocomplex PC4.2 contains relative amounts [F] of each of the four test materials; Expected $IC_{50}$ for PC4.2 = 1/(2.369) = 0.422 µg/mL.

Results—The $IC_{50}$ of PC4.2 was 0.201 µg/mL, while the calculated, expected $IC_{50}$ was 0.422 µg/mL resulting in a CI=2.10. Thus, PC4.2 synergistically produced 2.0-times the peroxynitrite-scavenging capacity than expected from the sum of its components.

Conclusion—With CI=2.10, PC4.2 unexpectedly produced 2.0-times the peroxynitrite-scavenging capacity than expected from the sum of its components Example 13

Synergistic Interactions of PC9p and Bergamot (PC10) on 295 Protein Kinases

Protein kinases represent a transferase class of enzymes that are able to transfer a phosphate group from a donor molecule (usually ATP) to an amino acid residue of a protein (usually threonine, serine or tyrosine). Kinases are used in signal transduction for the regulation of enzymes, i.e., they can inhibit or activate the activity of an enzyme, such as in cholesterol biosynthesis, amino acid transformations, or glycogen turnover. While most kinases are specialized to a single kind of amino acid residue, some kinases exhibit dual activity in that they can phosphorylate two different kinds of amino acids.

Methods—The inhibitory effect of the PC9p, bergamot and the combination of PC9p and bergamot (the PC10 formulation) were tested individually on human kinase activity in a panel of 295 kinases in the KinaseProfiler™ Assay (Millipore UK Ltd. Dundee, United Kingdom). The assay protocols for the specific kinases listed in Table 14 are summarized at http://www.millipore.com/techpublications/tech1/pf3036.

Median inhibitory concentrations ($IC_{50}$) were determined for the PC9p, bergamot, and PC10 by simple interpolation when a dose-response was observed over the three concentrations that captured the median effective concentration. The estimated $IC_{50}$ for the PC10 formulation was computed as described in Example 2 using the observed $IC_{50s}$ for PC9p and PC10 in the ratio of 3:7.

Synergy of test components was then quantified using the combination index (CI) parameter. This parameter defines only the additive effect rather than synergism or antagonism. Synergy, however, was defined as a more than expected additive effect (CI>1), and antagonism as a less than expected additive effect (CI<1) as described below.

Expected median inhibitory concentrations of any multi-component combination were estimated using the relationship:

$$[1/\text{Expected } IC_{50}] = [0.3/IC_{50}PC9p] + [0.7/IC_{50}\text{Bergamot}]$$

The CI was then calculated thusly, CI=Expected [$IC_{50}$]/Observed [$IC_{50}$]. Using the designation of CI=1 as the additive effect, for mutually exclusive compounds that have the same mode of action or for mutually non-exclusive drugs that have totally independent modes of action the following relationships are defined: CI<1, =1, and >1 indicating antagonism, additivity and synergy respectively. In these studies, CI>1.10 were considered evidence of synergy between the formulations.

TABLE 14

Combination Index for the Interaction of PC9f, Bergamot, and PC10 on 295 Kinases

| Kinase | PC9f $IC_{50}$ [µg/mL] | Bergamot $IC_{50}$ [µg/mL] | PC10 $IC_{50}$ [µg/mL] | Est PC10 $IC_{50}$† [µg/mL] | CI |
|---|---|---|---|---|---|
| PI3 Kinase (p110a/p85a) | 1068.73 | 5000 | 7.9 | 2377 | 002 |
| PI3 Kinase (p110a(H1047R)/p85a) | 5000.00 | 5000 | 25 | 5000 | 200 |
| Met(Y1248D) HGFR | 1.979 | 5000 | 0.05 | 6.59 | 132 |
| TrkC | 0.01 | 625 | 0.0002 | 0.02 | 86.1 |
| BTK(R28H) | 93.20 | 2.6 | 0.05 | 3.63 | 72.6 |
| PKCβII | 5000 | 5000 | 70 | 5000 | 71.9 |
| Fms | 4.18 | 9.0 | 0.12 | 6.70 | 54.0 |
| Met(Y1248H) | 0.73 | 5000 | 0.05 | 2.43 | 48.6 |
| Met(M1268T) HGFR | 0.500 | 187 | 0.05 | 1.66 | 33.2 |
| GRK6 (clotting) | 882.39 | 5000 | 63 | 2083 | 33.0 |
| ACK1 (also TNK2) | 0.05 | 65 | 0.01 | 0.166 | 24.9 |
| Met(D1246N) (HGFR) | 0.04 | 5000 | 0.005 | 0.133 | 24.4 |
| PRAK (stress induced) | 0.17 | 192 | 0.05 | 0.579 | 11.6 |
| CK2 | 46 | 0.07 | 0.01 | 0.100 | 11.4 |
| cKit(V654A) | 4.5 | 9.74 | 0.735 | 7.20 | 9.80 |
| PI3 Kinase (p110b/p85a) | 20.91 | 5000 | 7.2 | 69.0 | 9.65 |
| Rse (Toll-like receptors/NFKβ) | 24 | 5000 | 8.5 | 80.2 | 9.41 |
| PI3 Kinase (p120g) | 377.22 | 5000 | 120.29 | 1069 | 8.89 |
| PIP5K1g(h) | 0.02 | 5000 | 0.01 | 0.0780 | 8.33 |
| EGFR | 1.8 | 484 | 0.8 | 5.79 | 7.43 |
| PKCµ(h) | 163.46 | 5000 | 69.92 | 506 | 7.24 |
| PEK(h) | 3.3 | 5000 | 1.71 | 10.9 | 6.37 |
| GCK(h) | 0.01 | 20 | 0.01 | 0.0429 | 5.99 |
| IR activated | 6.35 | 197 | 3.54 | 19.7 | 5.56 |
| MSSK1(h) | 0.25 | 5000 | 0.16 | 0.848 | 5.42 |
| cKit(D816H) | 0.034 | 80 | 0.022 | 0.113 | 5.26 |
| PrKX(h) | 28.68 | 5000 | 18.65 | 94.3 | 5.06 |
| Pim-1(h) | 5.4 | 49 | 2.92 | 14.4 | 4.93 |
| DRAK1(h) | 21 | 131 | 11 | 50.7 | 4.63 |
| GSK3β(h) | 8.4 | 443 | 6.7 | 26.8 | 4.01 |
| Mnk2(h) | 0.51 | 19 | 0.41 | 1.60 | 3.93 |
| TAK1(h) | 316 | 1754 | 194 | 741 | 3.82 |
| MELK(h) | 0.78 | 55 | 0.66 | 2.51 | 3.80 |
| PRK2(h) | 11 | 5000 | 10 | 36.5 | 3.78 |
| CK1γ3(h) | 4.86 | 332 | 4.19 | 15.7 | 3.74 |
| JNK3(h) | 26 | 5000 | 23 | 84.1 | 3.73 |
| NEK11(h) | 1.6 | 5000 | 1.5 | 5.42 | 3.62 |

TABLE 14-continued

Combination Index for the Interaction of PC9f, Bergamot, and PC10 on 295 Kinases

| Kinase | PC9f IC$_{50}$ [μg/mL] | Bergamot IC$_{50}$ [μg/mL] | PC10 IC$_{50}$ [μg/mL] | Est PC10 IC$_{50}$† [μg/mL] | CI |
|---|---|---|---|---|---|
| cKit | 11.6 | 10 | 2.92 | 10.5 | 3.59 |
| Lyn(h) | 5.2 | 561 | 4.8 | 17.1 | 3.58 |
| PKCδ(h) | 50 | 5000 | 45 | 162 | 3.58 |
| CSK(h) | 2.3 | 411 | 2.17 | 7.62 | 3.51 |
| PhKγ2(h) | 0.9 | 5000 | 0.85 | 2.94 | 3.44 |
| LOK(h) | 6.3 | 5000 | 6.27 | 21.0 | 3.35 |
| TBK1(h) | 5.0 | 625 | 4.89 | 16.4 | 3.35 |
| PKCζ(h) | 5.0 | 5000 | 4.98 | 16.6 | 3.34 |
| Met(D1246H)(h) | 0.05 | 59744 | 0.050 | 0.167 | 3.33 |
| Met(Y1248C)(h) | 0.05 | 4356 | 0.050 | 0.167 | 3.33 |
| Syk(h) | 0.05 | 231 | 0.050 | 0.167 | 3.33 |
| CLK1(h) | 0.05 | 37.7 | 0.050 | 0.166 | 3.32 |
| Flt4(h) | 0.05 | 26.3 | 0.050 | 0.166 | 3.32 |
| PDGFRα(D842V)(h) | 0.05 | 18.4 | 0.050 | 0.166 | 3.31 |
| DYRK2(h) | 0.05 | 14.1 | 0.050 | 0.165 | 3.31 |
| RIPK2(h) | 0.05 | 13.5 | 0.050 | 0.165 | 3.30 |
| MLK1(h) | 0.05 | 7.64 | 0.050 | 0.164 | 3.28 |
| PKCα(h) | 175 | 5000 | 165 | 539 | 3.27 |
| BrSK1(h) | 11.7 | 130 | 9.9 | 32.2 | 3.25 |
| EphA4 | 4.36 | 5000 | 4.50 | 14.51 | 3.22 |
| AMPKα2 | 15.8 | 5000 | 16.6 | 52.3 | 3.16 |
| CHK2(R145W)(h) | 2.99 | 689 | 3.16 | 9.86 | 3.13 |
| eEF-2K(h) | 24.4 | 5000 | 25.8 | 80.3 | 3.12 |
| Flt3(D835Y)(h) | 0.05 | 1.33 | 0.050 | 0.153 | 3.06 |
| LKB1(h) | 101 | 5000 | 105 | 321 | 3.06 |
| SRPK2(h) | 5.46 | 5000 | 5.98 | 18.1 | 3.03 |
| Flt3(h) | 0.05 | 0.83 | 0.050 | 0.146 | 2.92 |
| HIPK2(h) | 4.85 | 25.0 | 3.85 | 11.1 | 2.89 |
| MSK2(h) | 12.9 | 5000 | 15.0 | 42.6 | 2.85 |
| BrSK2(h) | 17.3 | 43 | 10.8 | 29.6 | 2.74 |
| CaMKI(h) | 30.7 | 5000 | 37.4 | 101 | 2.70 |
| Ros(h) | 19.4 | 5000 | 24.9 | 64.2 | 2.57 |
| FGFR1(h) | 20.3 | 434 | 23.8 | 61.0 | 2.56 |
| EphB1 | 12.6 | 625 | 16.0 | 40.2 | 2.50 |
| Fyn(h) | 0.655 | 328 | 0.872 | 2.17 | 2.49 |
| mTOR(h) | 27.9 | 5000 | 37.7 | 91.9 | 2.44 |
| Pim-2(h) | 5.72 | 63 | 6.57 | 15.7 | 2.39 |
| cSRC(h) | 21.5 | 866 | 28.6 | 67.7 | 2.37 |
| CDK1/cyclinB(h) | 6.57 | 5000 | 9.45 | 21.8 | 2.31 |
| IGF-1R(h), activated | 19.8 | 391 | 25.8 | 59.1 | 2.29 |
| CHK2(I157T)(h) | 3.89 | 4412 | 5.7 | 12.9 | 2.26 |
| CK1γ1(h) | 16.9 | 5000 | 24.7 | 55.8 | 2.26 |
| PKBβ(h) | 23.6 | 5000 | 34.6 | 77.8 | 2.24 |
| CDK3/cyclinE(h) | 20.1 | 5000 | 29.7 | 66.4 | 2.24 |
| AMPKα1 | 6.88 | 1769 | 10.2 | 22.7 | 2.23 |
| EphB3 | 26.9 | 5000 | 39.9 | 88.5 | 2.22 |
| PAR-1Bα(h) | 15.4 | 5000 | 23.1 | 51.0 | 2.20 |
| Tec(h) activated | 5.04 | 5000 | 7.6 | 16.8 | 2.19 |
| DAPK2(h) | 22.9 | 123 | 24 | 53.2 | 2.19 |
| IRAK4(h) | 7.67 | 764 | 12 | 25.0 | 2.16 |
| PAK5(h) | 19.7 | 5000 | 30 | 65.1 | 2.16 |
| TAO1(h) | 13.2 | 5000 | 20 | 43.6 | 2.15 |
| IRAK1(h) | 14.5 | 3679 | 22 | 47.9 | 2.15 |
| ULK2(h) | 151 | 5000 | 219 | 469 | 2.15 |
| CDK2/cyclinE(h) | 19.0 | 5000 | 29.2 | 62.7 | 2.14 |
| MuSK(h) | 15.5 | 5000 | 24.0 | 51.4 | 2.14 |
| MAPK1(h) | 19.4 | 5000 | 29.9 | 64.0 | 2.14 |
| NEK2(h) | 21.5 | 5000 | 33.5 | 71.0 | 2.12 |
| PDGFRα(h) | 35.2 | 2843 | 53.9 | 114 | 2.11 |
| PAK1(h) | 37.6 | 5000 | 58.4 | 123 | 2.11 |
| Tie2(Y897S)(h) | 32.2 | 5000 | 50.6 | 106 | 2.09 |
| PDGFRβ(h) | 24.7 | 5000 | 39.0 | 81.5 | 2.09 |
| SRPK1(h) | 3.65 | 5000 | 5.85 | 12.2 | 2.08 |
| EphA7 | 44.3 | 5000 | 70.3 | 145 | 2.06 |
| Pyk2(h) | 30.8 | 5000 | 49.3 | 101 | 2.05 |
| Tie2 (h) | 26.8 | 5000 | 43.3 | 88.3 | 2.04 |
| MINK(h) | 8.85 | 5000 | 14.4 | 29.4 | 2.04 |
| CHK1(h) | 29.2 | 5000 | 47.2 | 96.0 | 2.03 |
| Arg(h) | 9.13 | 3417 | 15.1 | 30.3 | 2.01 |
| ULK3(h) | 19.4 | 5000 | 32.0 | 64.0 | 2.00 |
| cKit(D816V) | 7.43 | 5000 | 12.4 | 24.7 | 1.98 |
| FGFR4(h) | 3.52 | 5000 | 5.98 | 11.7 | 1.96 |
| Aurora-A | 11.1 | 91 | 14.8 | 28.9 | 1.95 |
| MST3(h) | 24.4 | 2027 | 40.7 | 79.2 | 1.95 |

TABLE 14-continued

Combination Index for the Interaction of PC9f, Bergamot, and PC10 on 295 Kinases

| Kinase | PC9f IC$_{50}$ [μg/mL] | Bergamot IC$_{50}$ [μg/mL] | PC10 IC$_{50}$ [μg/mL] | Est PC10 IC$_{50}$† [μg/mL] | CI |
|---|---|---|---|---|---|
| Mer(h) | 10.9 | 140 | 15.8 | 30.8 | 1.94 |
| CDK2/cyclinA(h) | 38.0 | 5000 | 64.1 | 125 | 1.94 |
| PASK(h) | 8.70 | 5000 | 14.9 | 28.9 | 1.94 |
| CaMKIIβ(h) | 16.8 | 1519 | 28.2 | 54.7 | 1.94 |
| Abl(T315I) | 5.47 | 801 | 9.26 | 17.9 | 1.94 |
| WNK2(h) | 13.7 | 5000 | 23.6 | 45.4 | 1.93 |
| CaMKIIγ(h) | 7.13 | 102 | 10.6 | 20.4 | 1.92 |
| Axl(h) | 17.4 | 5000 | 30.0 | 57.6 | 1.92 |
| KDR(h) | 1.94 | 5000 | 3.38 | 6.47 | 1.92 |
| PDK1(h) | 19.9 | 5000 | 34.3 | 65.8 | 1.92 |
| MST4(h) | 35.0 | 5000 | 60.2 | 115 | 1.91 |
| Rsk1(h) | 3.27 | 2483 | 5.72 | 10.9 | 1.90 |
| SGK3(h) | 29.5 | 5000 | 51.1 | 96.9 | 1.89 |
| MAPKAP-K2(h) | 29.8 | 5000 | 52.1 | 97.9 | 1.88 |
| PAK4(h) | 24.6 | 5000 | 43.3 | 81.2 | 1.88 |
| CDK6/cyclinD3(h) | 38.1 | 5000 | 66.5 | 125 | 1.88 |
| SGK(h) | 32.9 | 5000 | 57.9 | 108 | 1.87 |
| MKK7β(h) | 35.0 | 5000 | 61.7 | 115 | 1.86 |
| p70S6K(h) | 1.12 | 743 | 2.00 | 3.72 | 1.86 |
| TAO3(h) | 16.7 | 5000 | 29.8 | 55.3 | 1.86 |
| MST2(h) | 18.9 | 5000 | 33.7 | 62.4 | 1.85 |
| FGFR2(h) | 25.6 | 5000 | 45.6 | 84.5 | 1.85 |
| Fer(h) | 40.2 | 5000 | 71.5 | 132 | 1.84 |
| ZAP-70(h) | 11.7 | 5000 | 21.4 | 38.9 | 1.82 |
| Fgr(h) | 12.8 | 105 | 18.3 | 33.2 | 1.82 |
| EphA3 | 24.7 | 5000 | 44.9 | 81.4 | 1.81 |
| CDK5/p25(h) | 13.2 | 5578 | 24.5 | 43.8 | 1.79 |
| PKBα(h) | 33.4 | 5000 | 61.3 | 110 | 1.79 |
| IKKβ | 35.3 | 5000 | 65.5 | 116 | 1.77 |
| NLK(h) | 25.0 | 5000 | 46.7 | 82.4 | 1.77 |
| JAK3(h) | 18.6 | 5000 | 34.8 | 61.4 | 1.76 |
| WNK3(h) | 17.6 | 5000 | 33.0 | 58.1 | 1.76 |
| BTK(h) | 7.09 | 5000 | 13.5 | 23.6 | 1.75 |
| PKG1α(h) | 25.6 | 5000 | 48.2 | 84.2 | 1.75 |
| Ron(h) | 8.97 | 5000 | 17.1 | 29.8 | 1.74 |
| MARK1(h) | 6.66 | 5000 | 12.7 | 22.1 | 1.74 |
| Lck(h) | 24.0 | 444 | 41.0 | 71.1 | 1.74 |
| ROCK-I(h) | 55.9 | 5000 | 105 | 182 | 1.74 |
| TAO2(h) | 14.7 | 5000 | 28.2 | 48.7 | 1.73 |
| PKG1β(h) | 19.3 | 5000 | 37.0 | 63.8 | 1.73 |
| c-RAF(h) | 21.2 | 5000 | 40.5 | 69.9 | 1.72 |
| Fes(h) | 24.2 | 5000 | 46.4 | 79.7 | 1.72 |
| SGK2(h) | 28.3 | 5000 | 54.4 | 93.2 | 1.71 |
| DAPK1(h) | 83.1 | 5000 | 156 | 267 | 1.71 |
| LRRK2(h) | 36.6 | 327 | 56.5 | 96.7 | 1.71 |
| GSK3α(h) | 5.67 | 60.0 | 9.09 | 15.5 | 1.70 |
| ErbB4 | 27.2 | 5000 | 52.6 | 89.5 | 1.70 |
| EGFR(T790M) | 33.8 | 231 | 50.0 | 84.1 | 1.68 |
| Hck(h) | 17.3 | 97.1 | 24.3 | 40.8 | 1.68 |
| PKCγ(h) | 14.4 | 5000 | 28.6 | 47.8 | 1.67 |
| CLK4(h) | 0.0181 | 34.7 | 0.0363 | 0.0604 | 1.66 |
| ROCK-II(h) | 18.5 | 5000 | 36.7 | 61.0 | 1.66 |
| HIPK1(h) | 27.3 | 117 | 35.6 | 59.0 | 1.66 |
| Bmx(h) | 5.46 | 721 | 10.8 | 17.9 | 1.65 |
| TSSK2(h) | 30.2 | 5000 | 60.1 | 99.2 | 1.65 |
| MLCK(h) | 22.5 | 5000 | 45.3 | 74.2 | 1.64 |
| FGFR3(h) | 10.7 | 5000 | 21.6 | 35.4 | 1.64 |
| MSK1(h) | 52.3 | 5000 | 105 | 170 | 1.63 |
| TSSK1(h) | 21.5 | 5000 | 44.4 | å | 1.60 |
| GRK7 | 42.0 | 5000 | 86.4 | 137 | 1.59 |
| FGFR2(N549H)(h) | 22.4 | 388 | 41.4 | 65.9 | 1.59 |
| EphA5 | 32.4 | 5000 | 67.4 | 106 | 1.58 |
| Met(h) | 53.7 | 2538 | 108 | 171 | 1.57 |
| PKBγ(h) | 31.2 | 5000 | 65.2 | 102 | 1.57 |
| EGFR(T790M, L858R) | 16.9 | 60.1 | 21.8 | 34.1 | 1.56 |
| TYK2(h) | 31.7 | 82.7 | 35.8 | 55.8 | 1.56 |
| PAK6(h) | 29.3 | 5000 | 62.3 | 96.3 | 1.55 |
| IKKε | 37.2 | 5611 | 79.2 | 122 | 1.54 |
| ZIPK(h) | 16.8 | 5000 | 36.1 | 55.6 | 1.54 |
| EGFR(L858R) | 43.1 | 5000 | 92.3 | 141 | 1.53 |
| ALK4(insulin receptor family) | 136 | 5000 | 282 | 427 | 1.52 |
| PKCθ(h) | 28.6 | 5000 | 62.1 | 94.0 | 1.51 |
| EphA2 | 30.7 | 2613 | 65.9 | 100 | 1.51 |
| SIK(h) | 13.5 | 59.7 | 19.6 | 29.4 | 1.50 |

TABLE 14-continued

Combination Index for the Interaction of PC9f, Bergamot, and PC10 on 295 Kinases

| Kinase | PC9f IC$_{50}$ [µg/mL] | Bergamot IC$_{50}$ [µg/mL] | PC10 IC$_{50}$ [µg/mL] | Est PC10 IC$_{50}$† [µg/mL] | CI |
|---|---|---|---|---|---|
| IKKα | 46.2 | 5000 | 100 | 151 | 1.50 |
| ASK1(h) | 21.3 | 132 | 34.6 | 51.5 | 1.49 |
| SAPK4(h) | 75.8 | 5000 | 164 | 244 | 1.49 |
| CLK2(h) | 0.050 | 67.1 | 0.113 | 0.166 | 1.48 |
| NEK6(h) | 22.9 | 5000 | 51.2 | 75.4 | 1.47 |
| EphA1 | 20.6 | 76.2 | 28.9 | 42.1 | 1.46 |
| JAK1(h) | 11.1 | 165 | 22.0 | 31.9 | 1.45 |
| CHK2(h) | 1.98 | 468 | 4.50 | 6.53 | 1.45 |
| CDK9/cyclin T1(h) | 11.4 | 27.2 | 13.3 | 19.2 | 1.45 |
| TrkB(h) | 6.33 | 357 | 14.0 | 20.3 | 1.45 |
| CaMKIδ(h) | 34.8 | 5000 | 79.0 | 114 | 1.44 |
| Tie2(R849W)(h) | 17.2 | 5000 | 39.5 | 56.8 | 1.44 |
| MAPKAP-K3(h) | 50.6 | 5000 | 115 | 165 | 1.44 |
| HIPK3(h) | 7.53 | 51.4 | 13.1 | 18.7 | 1.43 |
| ALK(insulin receptor family) | 7.74 | 5000 | 18.0 | 25.7 | 1.43 |
| CDK7/cyclinH/MAT1(h) | 41.7 | 5000 | 96.0 | 136 | 1.42 |
| cKit(V560G) | 3.12 | 0.05 | 0.0500 | 0.0709 | 1.42 |
| LIMK1(h) | 28.0 | 72 | 34.4 | 48.8 | 1.42 |
| IR | 49.0 | 5128 | 113 | 160 | 1.41 |
| STK25(h) | 44.6 | 5000 | 104 | 146 | 1.41 |
| PTK5(h) | 33.5 | 60 | 34.8 | 48.6 | 1.40 |
| Fms(Y969C)(h) | 23.4 | 18 | 14.0 | 19.4 | 1.39 |
| mTOR/FKBP12(h) | 39.5 | 5000 | 92.9 | 129 | 1.39 |
| MRCKβ(h) | 31.2 | 5000 | 73.9 | 102 | 1.39 |
| EGFR(L861Q) | 17.4 | 77 | 27.6 | 37.9 | 1.37 |
| SAPK3(h) | 123 | 5000 | 284 | 389 | 1.37 |
| FAK(h) | 64.9 | 5000 | 153 | 210 | 1.37 |
| Ret(V804M)(h) | 3.13 | 2320 | 7.61 | 10.4 | 1.37 |
| EphB2 | 0.91 | 89 | 2.19 | 2.96 | 1.35 |
| Abl (H396P) | 5.15 | 127 | 11.7 | 15.7 | 1.34 |
| Txk(h) | 8.00 | 168 | 18.0 | 24.0 | 1.33 |
| CK1γ2(h) | 3.14 | 111 | 7.4 | 9.8 | 1.33 |
| MRCKα(h) | 52.2 | 5000 | 129 | 170 | 1.32 |
| FGFR1(V561M)(h) | 17.7 | 668 | 42.5 | 55.4 | 1.31 |
| EphA8 | 51.5 | 5000 | 129 | 168 | 1.30 |
| Src(1-530)(h) | 7.60 | 37 | 13.2 | 17.2 | 1.30 |
| Wee1(h) | 52.9 | 5000 | 133 | 172 | 1.29 |
| PKCι(h) | 14.6 | 5000 | 38.2 | 48.4 | 1.27 |
| CDK5/p35(h) | 14.4 | 5000 | 37.6 | 47.5 | 1.26 |
| CK1δ(h) | 19.0 | 5000 | 50.9 | 62.8 | 1.23 |
| Aurora-B | 0.0181 | 10 | 0.0500 | 0.0602 | 1.20 |
| PKA(h) | 44.3 | 5000 | 121 | 145 | 1.20 |
| CaMKIIδ(h) | 2.53 | 59 | 6.40 | 7.66 | 1.20 |
| B-Raf(h) | 41.2 | 5000 | 114 | 135 | 1.18 |
| DDR2(h) | 32.9 | 5000 | 91.9 | 108 | 1.18 |
| Itk(h) | 0.967 | 5000 | 2.78 | 3.22 | 1.16 |
| PI3 Kinase (p110a(E542K)/p85a)(h) | 25.0 | 5000 | 71.5 | 82.4 | 1.15 |
| CaMKIV(h) | 50.7 | 5000 | 144 | 165 | 1.14 |
| Abl(Y253F) | 4.28 | 93.4 | 11.4 | 12.9 | 1.13 |
| Abl | 5.24 | 4975 | 15.5 | 17.4 | 1.12 |
| MST1(h) | 27.8 | 5000 | 81.7 | 91.6 | 1.12 |
| Aurora-C | 48.3 | 13.4 | 15.4 | 17.1 | 1.11 |
| Rsk4(h) | 7.68 | 5000 | 23.5 | 25.5 | 1.08 |
| MEK1(h) | 42.3 | 5000 | 130 | 138 | 1.06 |
| Flt1 | 0.00683 | 119 | 0.0216 | 0.0228 | 1.06 |
| PKCη(h) | 330 | 5000 | 908 | 952 | 1.05 |
| TLK2(h) | 5128 | 5000 | 5000 | 5038 | 1.01 |
| Abl (Q252H) | 4.59 | 143 | 14.2 | 14.2 | 1.00 |
| DMPK | 5000 | 5000 | 5000 | 5000 | 1.00 |
| JNK1α1(h) | 5000 | 5000 | 5000 | 5000 | 1.00 |
| JNK2α2(h) | 5000 | 5000 | 5000 | 5000 | 1.00 |
| PIP5K1α(h) | 5000 | 5000 | 5000 | 5000 | 1.00 |
| PKCβI(h) | 5000 | 5000 | 5000 | 5000 | 1.00 |
| PKCε(h) | 5000 | 5000 | 5000 | 5000 | 1.00 |
| PKD2(h) | 5000 | 5000 | 5000 | 5000 | 1.00 |
| Plk1(h) | 5000 | 5000 | 5000 | 5000 | 1.00 |
| Plk3(h) | 5000 | 5000 | 5000 | 5000 | 1.00 |
| TGFBR1(h) | 5000 | 5000 | 5000 | 5000 | 1.00 |
| VRK2(h) | 5000 | 5000 | 5000 | 5000 | 1.00 |
| JAK2(h) | 145 | 5000 | 451 | 451 | 1.00 |
| EphB4 | 0.140 | 91.3 | 0.472 | 0.465 | 0.985 |
| Ret(h) | 0.006 | 64.7 | 0.022 | 0.020 | 0.931 |
| Ret (V804L)(h) | 0.436 | 118 | 1.55 | 1.44 | 0.927 |

TABLE 14-continued

Combination Index for the Interaction of PC9f, Bergamot, and PC10 on 295 Kinases

| Kinase | PC9f IC$_{50}$ [µg/mL] | Bergamot IC$_{50}$ [µg/mL] | PC10 IC$_{50}$ [µg/mL] | Est PC10 IC$_{50}$† [µg/mL] | CI |
|---|---|---|---|---|---|
| NEK3(h) | 10.7 | 5000 | 38.8 | 35.6 | 0.917 |
| Lck(h) activated | 9.7 | 47.4 | 24.1 | 21.9 | 0.911 |
| B-Raf(V599E)(h) | 28.4 | 1364 | 100 | 90.4 | 0.903 |
| Hck(h) activated | 15.0 | 45.8 | 31.8 | 28.3 | 0.891 |
| Pim-3(h) | 55.5 | 24.5 | 33.3 | 29.4 | 0.884 |
| Blk(h) | 0.122 | 100 | 0.466 | 0.406 | 0.870 |
| Rsk2(h) | 0.753 | 966 | 2.91 | 2.50 | 0.860 |
| Abl (M351T) | 3.59 | 272 | 13.5 | 11.6 | 0.860 |
| SAPK2b(h) | 50.3 | 5000 | 201 | 164 | 0.814 |
| STK33(h) | 0.0121 | 5000 | 0.050 | 0.040 | 0.804 |
| MAPK2(h) | 53.3 | 5000 | 218 | 173 | 0.794 |
| GRK5(h) | 229 | 5000 | 874 | 689 | 0.789 |
| TrkA(h) | 0.414 | 103 | 1.83 | 1.37 | 0.746 |
| Snk(h) | 456 | 5000 | 1688 | 1253 | 0.742 |
| PAK2(h) | 39.5 | 5000 | 178 | 129 | 0.725 |
| Rsk3(h) | 0.66 | 1759 | 3.16 | 2.18 | 0.692 |
| PIP4K2a(h) | 14.0 | 5000 | 71.5 | 46.5 | 0.650 |
| PDGFRα(V561D)(h) | 1.44 | 0.0227 | 0.050 | 0.032 | 0.645 |
| Src(T341M)(h) | 29.1 | 31.7 | 58.0 | 30.9 | 0.533 |
| BRK(h) | 0.850 | 5000 | 5.45 | 2.83 | 0.519 |
| NEK7(h) | 64.4 | 5000 | 456 | 208 | 0.457 |
| CK2α2(h) | 22.2 | 0.0121 | 0.050 | 0.017 | 0.344 |
| Haspin(h) | 0.605 | 250 | 6.51 | 2.00 | 0.308 |
| ARK5(h) | 0.477 | 247 | 5.85 | 1.58 | 0.271 |
| PI3 Kinase (p110a(E545K)/p85a)(h) | 42.7 | 5000 | 559 | 140 | 0.250 |
| SAPK2a(h) | 366 | 5000 | 5000 | 1041 | 0.208 |
| MKK6(h) | 361 | 5000 | 5085 | 1029 | 0.202 |
| DCAMKL2(h) | 304 | 5000 | 5000 | 887 | 0.177 |
| SAPK2a(T106M)(h) | 234 | 5000 | 5000 | 703 | 0.141 |
| PI3 Kinase (p110a/p65a)(h) | 98.0 | 5000 | 2825 | 312 | 0.111 |
| PI3 Kinase (p110d/p85a)(h) | 141 | 5000 | 5000 | 442 | 0.088 |
| Yes(h) | 0.0359 | 60.2 | 1.66 | 0.120 | 0.072 |
| PI3KC2g(h) | 300 | 58.3 | 1609 | 76.8 | 0.048 |
| CLK3(h) | 0.0171 | 5000 | 3.61 | 0.0572 | 0.016 |
| IGF-1R(h) | 79.0 | 0.191 | 78.4 | 0.273 | 0.003 |
| IRR(h) | 9.69 | 0.050 | 25.1 | 0.0713 | 0.0028 |
| PI3KC2a(h) | 0.050 | 5000 | 5000 | 0.167 | 0.00003 |

†Estimated using the equation [1/Expected IC$_{50}$] = [0.3/IC$_{50PC9p}$] + [0.7/IC$_{50Bergamot}$]

The kinases identified above can all be modulated by the protein kinase modulating composition provided herein.

The following paragraphs briefly summarize the cellular functioning of those kinases most affected by the synergistic interaction of the materials as evidenced by CI>1.05. The grouping is provided solely to underscore the primary signaling pathways in which the kinase functions and is not meant to be comprehensive.

PC10 dramatically and synergistically modulates kinase signaling of Abl, ACK1, ALK, Aurora, AMPK, CaMKII, EGFR, EphA, FAK, FGFR, GSK3, IGF-1(activated), IKK, IR, MAPK1, Met, MTOR, NEK1/2/6, PAK1/4/5/6, PDGFR, PI3K, PKC, ROCKI/II, RSK1/2/34, SRC, and Syk implying stimulation of skeletal muscle fatty acid oxidation and muscle glucose uptake, hepatic fatty acid oxidation and ketogenesis, inhibition of cholesterol synthesis, lipogenesis, and triglyceride synthesis, inhibition of adipocyte lipolysis and lipogenesis, and modulation of insulin secretion by pancreatic beta-cells.

Interestingly, a number of kinases involved in glucose metabolism were affected synergistically by the PC10 formulation including PI3 and MET kinase as well as the insulin receptor (IR) itself. Both isoforms of AMPK were also inhibited synergistically by the PC10 formulation.

PC10 synergistically inhibited all seven MET kinases. In adults, MET participates in wound healing as well as organ regeneration, tissue remodeling and certain aspects of brain development. The MET pathway also regulates the immune response and the development and repair of the gastrointestinal tract.

MET is a receptor tyrosine kinase that transduces signals from the extracellular matrix into the cytoplasm by binding to hepatocyte growth factor/HGF ligand. It regulates many physiological processes including proliferation, scattering, morphogenesis and survival. Ligand binding at the cell surface induces autophosphorylation of MET on its intracellular domain that provides docking sites for downstream signaling molecules. Following activation by ligand, interacts with the PI3-kinase subunit PIK3R1, PLCG1, SRC, GRB2, STAT3 or the adapter GAB 1.

All three Aurora kinases were inhibited synergistically by PC10. Most human cancer cells are characterized by changes in the amount or organization of DNA resulting in chromosome instability and aneuploidy. Several mitotic kinases, Aurora kinases amongst others, regulate the progression of the cell through mitosis. So far three Aurora kinases have been identified in man: Aurora-A, Aurora-B and Aurora-C. Aurora kinases were recently identified as a potential target in anticancer therapy, and various Aurora-A and Aurora-B kinase inhibitors are in development [Kitzen, J. J., de Jonge, M. J., and Verweij, J. (2010) Aurora kinase inhibitors, Crit Rev Oncol Hematol 73, 99-110]. In cancerous cells, over-expression of these enzymes causes unequal distribution of genetic information, creating aneuploid cells, a hallmark of cancer.

Four of the six isoforms of Abl were inhibited synergistically by PC10. Abl is a non-receptor tyrosine-protein kinase that plays a role in many key processes linked to cell growth and survival such as cytoskeleton remodeling in response to extracellular stimuli, cell motility and adhesion, receptorendocytosis, autophagy, DNA damage response and apoptosis.

Example 14

Clinical Assessment of PC10 in Normal and Pre-Diabetic Subjects

The clinical safety and efficacy of the PC10 formula, above was studied in an open-label, observational clinical trial. The study population included males and females between the ages of 18 to 72 inclusive exhibiting the following lipid variables: serum triglycerides ≥150 mg/dl and/or serum low density lipoprotein cholesterol (calculated) ≥150 mg/dl. During the 12-week study, subjects were assigned to one of three groups to receive, respectively, 500, 750, or 1000 mg of PC10 to be taken as 2, 3 or 4 capsules taken once daily with the evening meal.

Subjects were instructed to maintain their current lifestyles including diet, exercise, and mind body spirit practices without change during trial participation. Subjects were also instructed not to make changes to their current prescription, non-prescription medications, medical foods or nutritional supplements while on the study.

At one, two and three months, blood was drawn for analysis including complete blood count (CBC), complete metabolic panel (CMP), fasting lipid panel including total cholesterol, triglycerides, HDLc, LDLc, oxLDL, MPO, PAI-1, and HbA1c.

During this 12-week trial, there were no reported adverse events related to the PC10 in the 500, 750, or 1000 mg/day groups (N=35). Efficacy was assessed only for the potential commercial formulation of 500 mg PC10 (n-11).

Table 15 summarizes the changes (Initial-3 Months) in median lipid variables in subjects consuming 500 mg daily of the PC10 formulation over three months. Statistically significant changes were noted in Total Cholesterol, Total Cholesterol/HDL ration, LDL-c (calculated), Apo B and non-HDL for the group of eleven. The change in Total Cholesterol of 7% and LDL-c (calculated) of 10% are considered clinically meaningful.

Additionally, a subgroup analysis was conducted for subjects with a HbA1C >5.5% (all of whom were insulin resistant with HOMA scores greater than 2). Statistically significant changes were noted in Total Cholesterol, Total Cholesterol/HDL ration, LDL-c (calculated), Apo B, LDL-c (calculated)/HDL ratio, oxLDL, oxLDL/HDL ratio, non-HDL, Triglycerides, TG/HDL ratio and plasminogen activator inhibitor-1 (PAI-1) in this group of eight subjects. The change in Total Cholesterol of 10%, LDL-c (calculated) of 10%, oxLDL of 19%, TG of 27% and PAI-1 of 37% are clinically meaningful and demonstrate the broad spectrum of action of the PC10 formulation.

TABLE 15

Median changes in lipid biomarkers in all subjects and subset of subjects with elevated HbA1c consuming 500 mg daily of the PC10 formulation over three months

| | Total (n = 11) | | HbA1c > 5.4 (n = 8)† | |
|---|---|---|---|---|
| Variable | Median Change (% Change) | P* | Median Change (% Change) | P* |
| Weight | 0.0 (0.0) | NS | 1.0 (0.0) | NS |
| Total Cholesterol | −20 (−7.0) | 0.003 | −23 (−10) | 0.008 |
| HDL | −10 (−3.0) | NS | 4.0 (8.0) | NS |
| Cholesterol/HDL | −2.0 (−26) | 0.024 | −2.5 (−45) | 0.016 |
| LDL | −19 (−10) | 0.012 | −21 (−10) | 0.031 |
| oxLDL | −6.0 (−10) | NS | −14 (−19) | 0.047 |
| APOB | −4.0 (−3.0) | 0.037 | −7.0 (−4.0) | 0.016 |
| oxLDL/HDL | −0.2 (−17) | NS | −0.3 (−25) | 0.039 |
| Non-HDL | −16 (−7.0) | 0.007 | −21 (−11) | 0.008 |
| Triglycerides | −24 (−9.0) | NS | −35 (−27) | 0.039 |
| LDL/HDL | −0.3 (−7.0) | NS | −0.4 (−10) | 0.031 |
| PAI-1 | −4.0 (−20) | NS | −7.0 (−37) | 0.047 |

*P-values were computed using the log-normal distribution of the ratio of change from baseline to 12 weeks using the Wilcoxon Signed Rank test of the median. The Null Hypothesis assumed a mean change from baseline of zero.
NS = nonsignificant (P > 0.05)
†Subgroup of subjects selected with HbA1c greater than 5.4; bolding highlights subgroup differences.

Of particular interest in both groups was the effect of PC10 on oxLDL levels, which is considered by many to be the most significant risk factor for development of atherosclerosis [Johnston, N., Jernberg, T., Lagerqvist, B., Siegbahn, A., and Wallentin, L. (2006) Improved identification of patients with coronary artery disease by the use of new lipid and lipoprotein biomarkers, Am J Cardiol 97, 640-645]. For the overall group, there was a 10% reduction that nearly placed subjects at completion in the low risk group. The subgroup began the trial at moderate risk and had improved with a fall to the low risk group by completion. This reduction in an important risk factor for the development of coronary artery disease offers an additional opportunity to promote healthy aging. The antioxidant components of the formula function to assist in lowering oxLDL levels and promote a healthy cholesterol metabolism to offer organ system protection.

This is the first clinical demonstration of a formulation containing Bergamot reducing oxLDL. Moreover, the remaining fruit and herb components of PC10 have not been shown to reduce oxLDL at the doses used in this study—a further indication of the coordinated synergy built into the development of the PC10 and related formulations.

Example 15

Synergistic Interactions of PC8 and Bergamot (PC10) on Ex Vivo Inhibition of LDL Oxidation Objective—The objective of this example is to demonstrate the synergistic interaction between various forms of the phytocomplex and bergamot on the ex vivo inhibition of LDL oxidation.

Method—This method artificially induces autoxidation of linoleic acid or LDL by either Cu(II) or an azo initiator as reported by Pryor and co-workers [Pryor, W. A.; Cornicelli, J. A.; Devall, L. J.; Tait, B.; Trivedi, B. K.; Witiak, D. T.; Wu, M. A rapid screening test to determine the antioxidants potencies of natural and synthetic antioxidants. J. Org. Chem. 1993, 58, 3521-3532]. The progress of autoxidation is monitored by UV absorbance at 234 nm.

Materials—PC8, PC9f, PC9p and bergamot are used in this example and there compositions are as previously described in earlier examples.

Calculations—Median inhibitory concentrations ($IC_{50}$) are calculated from a minimum of four concentrations evenly surrounding the median effect. The Combination Index (CI) is computed as previously described.

Conclusion—CI for PC8 plus bergamot, PC9f plus bergamot and PC9f plus bergamot are all greater than 3.0 indicating a high degree of synergy in the prevention of ex vivo oxidation of LDL. These results support the clinical findings of Example 14 and underscore the novelty of the inhibition of oxidized LDL for the combinations.

Thus, among the various formulations taught there have been disclosed novel methods and compositions of extracts of fruits and herbs that exhibited synergistic antioxidant activity toward differing oxidants over several configurations.

Example 16

Phytocomplex (PC4) Through Inhibition of Peroxynitrite Formation

This example describes formulae for the enhancement of function of formulations targeted for metabolic disorders associated with oxidative stress as previously described with the addition of PC4.1 or PC4.2 functioning as synergistic inhibitors of macrophage $ONOO^-$ production (See FIG. 2). Under pathological conditions associated with increased oxidative stress and inflammation (myocardial infarction, ischemic heart disease, myocarditis, cardiomyopathy, hypertension, obesity, chronic intoxication, etc.), NO and superoxide ($O_2$) react to form $ONOO^-$ that induces cell damage via lipid peroxidation, inactivation of enzymes and other proteins by oxidation and nitration, and also activation of stress signaling enzymes such as matrix metalloproteinases and myeloperoxidase among others. Such stress signaling results in the attenuation of many products originally designed to address these conditions.

The administration of therapeutic amounts of PC4.1 or PC4.2 in combination with specific product formulations would function to relieve the oxidative stress and improve product performance. Examples of formulations in which PC4.1 or PC4.2 would be useful for their enhanced performance can be found in the following tables. However, it is noted that the other formulations noted above as PC8, PC9, and PC10 could in some embodiments also be used.

TABLE 16

PC4.1 Formulation with Arginine and Watermelon Extract

| Item Description | Amount [mg] |
| --- | --- |
| L-Arginine [granular] | 2500 |
| Citric Acid | 2500 |
| Red Beet Root | 3000 |
| Natural Citrus Sweetener [CitriSweet(TM)] | 430 |
| Malic Acid | 400 |
| Pomegranate Fruit Juice Concentrate | 375 |
| Xylitol [bulk] | 500 |
| Silicon Dioxide [Syloid ® 244] | 170 |
| Thiamin (B1) (thiamine mononitrate) [91% B1] | 110 |
| Calcium Ascorbate [83% vit C, 9% Ca] | 95 |
| Citrus Blend Natural Flavor [WONF] | 85 |
| Huckleberry Natural Flavor | 85 |
| Magnesium Oxide [60% Mg, powder] | 84 |
| Stevia Leaf Extract | 66 |
| Apple Fruit Extract [75% polyphenols] | 30 |
| Watermelon Whole Fruit Extract [20% Citrulline] | 23 |
| Vitamin D3 (cholecalciferol) [100,000 IU/g, 100 SD/S] | 16 |
| Green Tea Leaf Extract [80%, decaffeinated] | 15 |
| D-Ribose | 10 |
| Grape Skin Extract | 5 |
| Red Grape Polyphenol Extract [ExGrape(TM) red wine extract] | 5 |
| Grape Seed Extract [MegaNatural ®] | 5 |
| Olive Leaf Extract [12%, 7:1] | 5 |
| Folic Acid [10%, trituration] | 3 |
| Vitamin B6 (pyridoxine hydrochloride) [82% B6] | 3 |
| Vitamin B12 (cyanocobalamin) [1%, trituration] | 0.9 |
| Inulin (chicory root extract) [HD food grade] | 2500 |
| L-Glutamine | 1000 |

TABLE 17

PC4.1 Formulation with Arginine and Citrulline for Enhanced Production of Nitric Oxide

| Item Description | Amount [mg] |
| --- | --- |
| L-Arginine [granular] | 20 |
| Citric Acid | 1000 |
| Red Beet Root | 3000 |
| Natural Citrus Sweetener [CitriSweet(TM)] | 300 |
| Malic Acid | 400 |
| Silicon Dioxide [Syloid ® 244] | 170 |
| Thiamin (B1) (thiamine mononitrate) [91% B1] | 110 |
| Calcium Ascorbate [83% vit C, 9% Ca] | 95 |
| Citrus Blend Natural Flavor [WONF] | 85 |
| Huckleberry Natural Flavor | 85 |
| Magnesium Oxide [60% Mg, powder] | 84 |
| Stevia Leaf Extract | 50 |
| Apple Fruit Extract [75% polyphenols] | 30 |
| Vitamin D3 (cholecalciferol) [100,000 IU/g, 100 SD/S] | 7.5 |
| Green Tea Leaf Extract [80%, decaffeinated] | 15 |
| Grape Skin Extract | 5 |
| Red Grape Polyphenol Extract [ExGrape(TM) red wine extract] | 5 |
| Grape Seed Extract [MegaNatural ®] | 5 |
| Olive Leaf Extract [12%, 7:1] | 5 |
| Folic Acid [10%, trituration] | 1 |
| Vitamin B6 (pyridoxine hydrochloride) [82% B6] | 3 |
| Vitamin B12 (cyanocobalamin) [1%, trituration] | 0.9 |
| L-Citrulline | 2500 |

TABLE 18

PC4.1 Formulation with Arginine for Enhanced Production of Nitric Oxide

| Item Description | Amount [mg] |
| --- | --- |
| L-Arginine [granular] | 5100 |
| Citric Acid | 2000 |
| Red Beet Root | 2000 |
| Natural Citrus Sweetener [CitriSweet(TM)] | 430 |
| Malic Acid | 400 |
| Pomegranate Fruit Juice Concentrate | 375 |
| Xylitol [bulk] | 250 |
| Silicon Dioxide [Syloid ® 244] | 170 |
| Thiamin (B1) (thiamine mononitrate) [91% B1] | 110 |
| Calcium Ascorbate [83% vit C, 9% Ca] | 95 |
| Citrus Blend Natural Flavor [WONF] | 85 |
| Huckleberry Natural Flavor | 85 |
| Magnesium Oxide [60% Mg, powder] | 84 |
| Stevia Leaf Extract | 66 |
| Apple Fruit Extract [75% polyphenols] | 30 |

TABLE 18-continued

PC4.1 Formulation with Arginine for Enhanced Production of Nitric Oxide

| Item Description | Amount [mg] |
| --- | --- |
| Watermelon Whole Fruit Extract [20% Citrulline] | 23 |
| Vitamin D3 (cholecalciferol) [100,000 IU/g, 100 SD/S] | 16 |
| Green Tea Leaf Extract [80%, decaffeinated] | 15 |
| D-Ribose | 10 |
| Grape Skin Extract | 5 |
| Red Grape Polyphenol Extract [ExGrape(TM) red wine extract] | 5 |
| Grape Seed Extract [MegaNatural ®] | 5 |
| Olive Leaf Extract [12%, 7:1] | 5 |
| Folic Acid [10%, trituration] | 3 |
| Vitamin B6 (pyridoxine hydrochloride) [82% B6] | 3 |
| Vitamin B12 (cyanocobalamin) [1%, trituration] | 0.9 |

TABLE 19

PC4.2 Formulation with Phytosterols

| Item Description | Amount [mg] |
| --- | --- |
| Maltodextrin [M100 IP] | 1453 |
| Sucralose | 30 |
| Chocolate Natural Flavor | 467 |
| Cocoa [processed w/alkali, 10-12% fat] | 2333 |
| Sunflower Oil Creamer (milk, soy)[RichmixSun50 HT, ALLERG] | 2147 |
| CLA (Conjugated Linoleic Acid) (milk) [Clarinol(TM), ALLERG] | 156 |
| Calcium Caseinate (contains milk) [ALLERGEN] | 2213 |
| Whey Protein Concentrate (milk, soy) [80% instantized ALLER] | 15625 |
| Whey Protein Isolate (milk) [instantized, ALLERGEN] | 8203 |
| Xanthan Gum [Keltrol(TM) Tf] | 373 |
| Apple Fruit Extract [75% polyphenols] | 30 |
| Green Tea Leaf Extract [80%, decaffeinated] | 15 |
| Grape Seed Extract [MegaNatural ®]/*Vitis vinifera* | 5 |
| Olive Leaf Extract [12%, 7:1] | 5 |
| Phytosterols | 2000 |

TABLE 20

PC4.2 Bergamot Fruit Extract Formulation for Enhanced Reduction of Oxidized LDL

| Item Description | Amount [mg] |
| --- | --- |
| Bergamot orange fruit extract | 250 |
| Apple Fruit Extract [75% polyphenols] | 30 |
| Green Tea Leaf Extract [80%, decaffeinated] | 15 |
| Grape Seed Extract [MegaNatural ®]/*Vitis vinifera* | 5 |
| Olive Leaf Extract [12%, 7:1] | 5 |
| Cellulose [hydroxypropyl cellulose, Klucel Nutra ® D] | 10 |
| Magnesium Stearate (vegetable) | 16.25 |
| Cellulose [croscarmellose sodium, modified cellulose gum] | 40 |
| Silicon Dioxide [Syloid ® 244] | 3.12 |

TABLE 21

PC4.2 Formulation for Enhanced Detoxification

| Item Description | Amount [mg] |
| --- | --- |
| Broccoli Flowers/*Brassica oleracea* var. *italica* | 18 |
| Apple Fruit Extract [75% polyphenols]/*Malus pumila* | 1.8 |
| Cabbage Leaf/*Brassica oleracea* var. *capitata* | 0.480 |
| Carrot Root/*Daucus carota* | 0.480 |

TABLE 21-continued

PC4.2 Formulation for Enhanced Detoxification

| Item Description | Amount [mg] |
| --- | --- |
| Flax Seed/*Linum usitatissimum* | 36 |
| Grape Seed Extract [MegaNatural ®]/*Vitis vinifera* | 0.300 |
| Green Tea Leaf Extract [80%, decaffeinated]/*Camellia sinensis* | 0.900 |
| Guar Gum [Tico-LV]/*Cyamopsis tetragonoloba* | 36 |
| Olive Leaf Extract [12%, 7:1]/*Olea europaea* | 0.300 |
| Red Beet Root/*Beta vulgaris* | 0.480 |
| Rosemary Leaf/*Rosmarinus officinalis* | 0.480 |
| Stevia Leaf Extract/*Stevia rebaudiana* | 1.8 |
| Tomato Fruit/*Solanum lycopersicum* | 0.480 |
| Turmeric Rhizome/*Curcuma longa* | 0.480 |
| Psyllium Hulls [50]/*Plantago ovata* | 187.920 |
| Gum Arabic (Talha)/*Acacia seyal* | 36 |
| Apple Fruit Fiber [40 mesh] | 108 |
| Citric Acid | 30 |
| Citrus Blend Natural Flavor [WONF] | 10.5 |
| Fructose | 60 |
| L-Glutamine | 150 |
| Inulin (chicory root extract) [HD food grade] | 150 |
| Sodium Copper Chlorophyllin | 6.0 |
| Zinc Citrate [32% Zn, dihydrate] | 0.240 |

TABLE 22

PC4.2 Formulation for Enhanced Detoxification

| Item Description | Amount [mg] |
| --- | --- |
| Broccoli Flowers | 1000 |
| Cabbage Leaf | 8 |
| Carrot Root | 8 |
| Red Beet Root | 8 |
| Rosemary Leaf | 8 |
| Tomato Fruit | 8 |
| Turmeric Rhizome | 1000 |
| Flax Seed | 600 |
| Guar Gum [Tico-LV] | 600 |
| Stevia Leaf Extract | 30 |
| Psyllium Hulls [50] | 3132 |
| Gum Arabic (Talha) | 600 |
| Apple Fruit Fiber [40 mesh] | 1800 |
| L-Glutamine | 2500 |
| Fructose | 1000 |
| Inulin (chicory root extract) [HD food grade] | 2500 |
| Apple Fruit Extract [75% polyphenols] | 30 |
| Green Tea Leaf Extract [80%, decaffeinated] | 15 |
| Grape Seed Extract [MegaNatural ®] | 5 |
| Olive Leaf Extract [12%, 7:1] | 5 |
| Zinc Citrate [32% Zn, dihydrate] | 4 |
| Citric Acid | 750 |
| Lemon Natural Flavor | 500 |

TABLE 23

PC4.2 Multivitamin Formulation for Enhanced Antioxidant Activity

| Item Description | Amount [mg] |
| --- | --- |
| Biotin [1% trituration] | 4.5 |
| Chromium Chloride (2%) | 2.0 |
| Copper Gluconate [14% Cu] | 3.9 |
| Vitamin B12 (cyanocobalamin) [1%, trituration] | 0.4428 |
| Cellulose [MCC, Endurance(TM) VE-090] | 105 |
| Folic Acid [10%, trituration] | 0.64 |
| Vitamin B6 (pyridoxine hydrochloride) [82% B6] | 5.4 |
| Riboflavin (B2) [100%, type S] | 6.0 |
| Thiamin (B1) (thiamine mononitrate) [91% B1] | 7.9 |
| Vitamin A Palmitate [500,000 IU/gm] | 2.7 |

TABLE 23-continued

PC4.2 Multivitamin Formulation for Enhanced Antioxidant Activity

| Item Description | Amount [mg] |
|---|---|
| Vitamin D3 (cholecalciferol) [100,000 IU/g, 100 SD/S] | 2.0 |
| Cellulose [hydroxypropyl cellulose, Klucel Nutra ® D] | 10 |
| Lutein [5%, VG granules] | 20 |
| Cellulose [croscarmellose sodium, modified cellulose gum] | 40 |
| Dicalcium Phosphate [anhydrous] | 382.5 |
| Vitamin C (ascorbic acid) [97%, C97 SF] | 155 |
| Cellulose [Avicel ® PH 200, microcrystalline] | 130 |
| Beta-Carotene [20%, CWD] | 8.1 |
| Pantothenic Acid (d-calcium pantothenate) [90%] | 20.9 |
| Vitamin E 700 IU, IP NON GMO (d-alpha tocopheryl acetate) | 43 |
| Stearic Acid (vegetable) [Hystrene ® NF] | 50 |
| Magnesium Oxide [60% Mg, granular] | 91 |
| Magnesium Stearate (vegetable) | 16.25 |
| Niacinamide [97%, fine granular] | 18 |
| Sodium Copper Chlorophyllin | 2.5 |
| Silicon Dioxide [Syloid ® 244] | 3.12 |
| Zinc Gluconate [13.8% Zn, fine granular] | 65 |
| Apple Fruit Extract [75% polyphenols] | 30 |
| Green Tea Leaf Extract [80%, decaffeinated] | 15 |
| Grape Seed Extract [MegaNatural ®]/*Vitis vinifera* | 5 |
| Olive Leaf Extract [12%, 7:1] | 5 |

TABLE 24

PC4.2 Meal Replacement Formula for Enhanced Weight Loss Activity

| Item Description | Formula 1 | Formula 2 | Formula 3 |
|---|---|---|---|
| Serving Size (g) | 46 | 45 | 45 |
| Calories | 184 | 180 | 173 |
| Fat (g) | 5 | 3 | 5 |
| Saturated Fat (g) | 2 | 1 | 1 |
| Trans Fat (g) | 0 | 0 | 0 |
| Cholesterol (mg) | 32 | 0 | 0 |
| Sodium (mg) | 104 | 150 | 307 |
| Potassium (mg) | 368 | 95 | 187 |
| Carbohydrate (g) | 14 | 16 | 16 |
| Dietary Fiber (g) | 5 | 3 | 3 |
| Sugars (g) | 5 | 9 | 8 |
| Protein (g) | 20 | 20 | 20 |
| Phytosterols (mg) | 2000 | 2000 | 2000 |
| Vitamin A (IU) | 48 | 75 | 47 |
| Vitamin C (mg) | 48 | 75 | 47 |
| Calcium (mg) | 96 | 2 | 33 |
| Iron (mg) | 0 | 0 | 0 |
| Vitamin A (IU) | 48 | 75 | 47 |
| Vitamin D (IU) | 0 | 75 | 47 |
| Vitamin E (IU) | 48 | 0 | 47 |
| Vitamin K (mcg) | 0 | 0 | 0 |
| Thiamin (mg) | 48 | 75 | 47 |
| Riboflavin (mg) | 48 | 75 | 47 |
| Niacin (mg) | 48 | 75 | 47 |
| Vitamin B6 (mg) | 48 | 75 | 47 |
| Folate (as folic acid and L-5-methyltetrahydrofolate) (mcg) | 104 | 75 | 47 |
| Vitamin B12 (as cyanocobalamin) (mcg) | 48 | 75 | 47 |
| Biotin (mcg) | 48 | 75 | 47 |
| Pantothenic Acid (mg) | 48 | 75 | 47 |
| Apple Fruit Extract [75% polyphenols] (mg) | 30 | 30 | 30 |
| Green Tea Leaf Extract [80%, decaffeinated] (mg) | 15 | 15 | 15 |
| Grape Seed Extract [MegaNatural ®]/*Vitis vinifera* (mg) | 5 | 5 | 5 |
| Olive Leaf Extract [12%, 7:1] (mg) | 5 | 5 | 5 |
| Phosphorus (mg) | 48 | 0 | 20 |
| Iodine (mcg) | 0 | 75 | 47 |
| Magnesium (mg) | 72 | 0 | 33 |
| Zinc (mg) | 0 | 75 | 47 |
| Selenium (mcg) | 0 | 75 | 47 |
| Copper (mg) | 0 | 75 | 47 |
| Manganese (mg) | 0 | 75 | 47 |
| Chromium (mcg) | 176 | 75 | 47 |
| Molybdenum | 0 | 75 | 0 |
| Chloride (mg) | 0 | 0 | 0 |

TABLE 25

PC4.2 Curcumin Formulation for Enhanced Anti-inflammatory/Antioxidant Activity

| Item Description | Amount [mg] |
|---|---|
| Tumeric rhizome extract (*Curcuma longa*) standardized to 95% curcuminoids | 550 |
| Apple Fruit Extract [75% polyphenols] | 30 |
| Green Tea Leaf Extract [80%, decaffeinated] | 15 |
| Grape Seed Extract [MegaNatural ®]/*Vitis vinifera* | 5 |
| Olive Leaf Extract [12%, 7:1] | 5 |
| Cellulose [Avicel ® PH 200, microcrystalline] | 130 |
| Magnesium Stearate (vegetable) | 16.25 |
| Silicon Dioxide [Syloid ® 244] | 3.12 |
| Black pepper fruit extract (*Piper nigram*) | 0.40 |

TABLE 26

PC4.2 Berberine Formulation for Enhanced Hypoglycemic/Anti-inflammatory Activity

| Item Description | Amount [mg] |
|---|---|
| Berberine (*Berberis aristata*) | 333 |
| Apple Fruit Extract [75% polyphenols] | 30 |
| Green Tea Leaf Extract [80%, decaffeinated] | 15 |
| Grape Seed Extract [MegaNatural ®]/*Vitis vinifera* | 5 |
| Olive Leaf Extract [12%, 7:1] | 5 |
| Cellulose [Avicel ® PH 200, microcrystalline] | 130 |
| Magnesium Stearate (vegetable) | 16.25 |
| Silicon Dioxide [Syloid ® 244] | 3.12 |

TABLE 27

PC4.2 Fish Oil Soft Gel Formulation for Enhanced Lipid Lowering Activity

| Item Description | Amount [mg] |
|---|---|
| Fish Oil ((380 mg EPA, 190 mg DHA)† | 1028 |
| Apple Fruit Extract [75% polyphenols] | 30 |
| Green Tea Leaf Extract [80%, decaffeinated] | 15 |
| Grape Seed Extract [MegaNatural ®]/*Vitis vinifera* | 5 |
| Olive Leaf Extract [12%, 7:1] | 5 |
| Gelatin | 300.6 |
| Water | 50.1 |
| Natural lemon oil | 29.01 |

†EPA = Eicosapentaenoic acid; DHA = Docosahexaenoic acid

TABLE 28

PCx CoQ10 Formulation for Enhanced Cardioprotective Activity

| Item Description | Amount [mg] |
| --- | --- |
| Coenzyme Q10 | 100 |
| Apple Fruit Extract [75% polyphenols] | 30 |
| Green Tea Leaf Extract [80%, decaffeinated] | 15 |
| Grape Seed Extract [MegaNatural ®]/*Vitis vinifera* | 5 |
| Olive Leaf Extract [12%, 7:1] | 5 |
| Extra virgin olive oil | 100 |
| Beeswax | 50 |
| Gelatin | 300.6 |
| Water | 50.1 |

Exemplary Embodiments

The following exemplary invention embodiments pertain to further aspects of the disclosure.

In one example there is provided, a composition having a therapeutic effect against multiple biologically reactive forms of oxygen and nitrogen when administered to a subject comprising: an apple fruit extract, a grape seed extract, a green tea leaf extract, and an olive leaf extract, wherein the composition is more effective against the biologically active forms of oxygen and nitrogen than an equivalent amount of any single extract in the composition.

In one example, the composition further comprises a blueberry fruit extract, a capsicum fruit extract, and a grape skin extract, wherein the composition is more effective against the biologically active forms of oxygen and nitrogen than an equivalent amount of any single extract in the composition.

In one example, the composition further comprises a bergamot fruit extract, a mangosteen fruit or pericarp extract, or a combination thereof, wherein the composition is more effective against the biologically active forms of oxygen and nitrogen than an equivalent amount of any single extract in the composition.

In one example, the composition further comprises a bergamot fruit extract.

In one example, the composition further comprises a mangosteen fruit extract.

In one example, the composition further comprises a mangosteen pericarp extract.

In one example, the composition further comprises a combination of a bergamot fruit extract and either a mangosteen fruit or mangosteen pericarp extract.

In one example, the extracts in the composition are each present in an equivalent amount.

In one example, the ratio is a 1:1 for all extracts in the composition.

In one example, at least one extract is present in a different amount than the other extracts.

In one example, a method for treating an oxidative stress related pathology in a subject comprising administering a therapeutically effective amount of a composition as recited in any of examples above to the subject.

In one example, the oxidative stress related pathology is increased oxidized LDL cholesterol (oxLDL).

In one example, the oxidative stress related pathology is any one of metabolic syndrome, type 1 diabetes, type 2 diabetes, or type 3 diabetes.

In one example, the oxidative stress related pathology is any one of leaky gut, endotoxemia, or inflammatory bowel disease.

In one example, the oxidative stress related pathology is any one of: obesity, an inflammation condition including osteoarthritis, rheumatoid arthritis, Crohn's disease, prostate hyperplasia, lower urinary tract symptoms, pulmonary arterial hypertension, diminished exercise capacity, premature ejaculation, low female sex drive, congestive disorders, cardiac failure, pulmonary hypertension, various cardiovascular diseases, motor dysfunction, cognitive disorders including Alzheimer's disease, Raynaud's phenomenon, essential hypertension, stroke, asthma, multiple sclerosis, vasculitis, Addison's Disease, lupus, thyroiditis, chronic fatigue syndrome, fibromyalgia, skin disorders including skin wrinkles, skin discolorations and skin sagging, and cancers arising from oxidized damage to DNA.

In one example, a method of modulating disease-associated protein kinase activity in a subject in a manner beneficial to the subject's health comprising administering a therapeutically effective amount of a composition as recited in any one of the examples above to the subject.

In one example, the disease-associated protein kinase is a member selected from the group consisting of: Abl, ACK1, ALK, Aurora, AMPK, CaMKII, EGFR, EphA, FAK, FGFR, GSK3, IGF-1(activated), IKK, IR, MAPK1, Met, MTOR, NEK1/2/6, PAK1/4/5/6, PDGFR, PI3K, PKC, ROCKI/II, RSK1/2/34, SRC, Syk, and combinations thereof, and modulation of the protein kinase reduces, minimizes, or inhibits production or presence of oxidized LDL (oxLDL) cholesterol in the subject.

In one example, the disease-associated protein kinase is a member selected from the group consisting of: Abl, ACK1, ALK, Aurora, AMPK, CaMKII, EGFR, EphA, FAK, FGFR, GSK3, IGF-1(activated), IKK, IR, MAPK1, Met, MTOR, NEK1/2/6, PAK1/4/5/6, PDGFR, PI3K, PKC, ROCKI/II, RSK1/2/34, SRC, Syk, and combinations thereof and modulation of the protein kinase results ameliorates at least one of metabolic syndrome, type 1 diabetes, type 2 diabetes, or type 3 diabetes.

In one example, the disease-associated protein kinase is a member selected from the group consisting of Abl, ACK1, ALK, Aurora, AMPK, CaMKII, EGFR, EphA, FAK, FGFR, GSK3, IGF-1(activated), IKK, IR, MAPK1, Met, MTOR, NEK1/2/6, PAK1/4/5/6, PDGFR, PI3K, PKC, ROCKI/II, RSK1/2/34, SRC, Syk and combinations thereof and modulation of the protein kinase ameliorates at least one of leaky gut, endotoxemia, or inflammatory bowel disease.

In one example, the disease-associated protein kinase is a member selected from the group consisting of: Abl, ACK1, ALK, Aurora, AMPK, CaMKII, EGFR, EphA, FAK, FGFR, GSK3, IGF-1(activated), IKK, IR, MAPK1, Met, MTOR, NEK1/2/6, PAK1/4/5/6, PDGFR, PI3K, PKC, ROCKI/II, RSK1/2/34, SRC, Syk and combinations thereof and modulation of the protein kinase ameliorates at least one of obesity, inflammation conditions including osteoarthritis and rheumatoid arthritis, Crohn's disease, prostate hyperplasia, lower urinary tract symptoms, pulmonary arterial hypertension, diminished exercise capacity, premature ejaculation, low female sex drive, congestive disorders, cardiac failure, pulmonary hypertension, cardiovascular diseases, motor dysfunction, cognitive disorders including Alzheimer's disease, Raynaud's phenomenon, essential hypertension, stroke, asthma, multiple sclerosis, vasculitis, Addison's Disease, lupus, thyroiditis, chronic fatigue syndrome, fibromyalgia and skin disorders including skin wrinkles, skin discolorations and skin sagging.

In one example, the disease associated protein kinase is a member selected from the group consisting of: Abl, ACK1, ALK, Aurora, AMPK, CaMKII, EGFR, EphA, FAK, FGFR, GSK3, IGF-1(activated), IKK, IR, MAPK1, Met, MTOR, NEK1/2/6, PAK1/4/5/6, PDGFR, PI3K, PKC, ROCKI/II, RSK1/2/34, SRC, Syk, and combinations thereof and modulation of the protein kinase results at least one of in stimulation of skeletal muscle fatty acid oxidation and muscle glucose uptake, hepatic fatty acid oxidation and ketogenesis, inhibition of cholesterol synthesis, lipogenesis, triglyceride synthesis, inhibition of adipocyte lipolysis and lipogenesis, and modulation of insulin secretion by pancreatic beta-cells.

In one example, a method of treating a serum lipid disorder or condition in a subject comprising administering a therapeutically effective amount a composition as recited in any one of the example compositions above to the subject.

In one example, the lipid disorder or condition includes abnormally elevated LDL.

In one example, the LDL includes oxidized LDL (oxLDL).

In one example, the lipid disorder or condition includes abnormally low HDL.

In one example, a method of minimizing serum oxidized LDL (oxLDL) in a subject comprising administering a therapeutically effective amount of a composition as recited in any one of the example compositions above to the subject.

Thus, there have been disclosed novel compositions that synergistically 1 modulate oxidative stress and protein kinase activity; as well as, methods of regulating oxidative stress, disease associated protein kinase activity; and methods of making such activity enhancing compositions. It will be readily apparent to those skilled in the art, however that various changes and modifications of an obvious nature may be made without departing from the spirit of the disclosed invention embodiments, and all such changes and modifications are considered to fall within the scope of the invention as recited herein, including in the appended claims. Examples of such changes and modifications could include, but not be limited to, the incipient ingredients added to affect the capsule, tablet, powder, lotion, food or bar manufacturing process as well as vitamins, flavorings and carriers. Other examples of such changes or modifications could include the use of herbs or other botanical products containing the combinations of the preferred embodiments disclosed above.

What is claimed is:

1. A method of regulating protein kinase modulating activity in a subject comprising:
    administering to the subject a therapeutically effective combination of apple, grape, green tea, and olive extracts, in amounts that provide a combined protein kinase modulating activity that is greater than a protein kinase modulating activity provided by an equivalent amount of any one extract or a sum of the extracts.

2. The method of claim 1, wherein;
    the apple extract comprises an extract of skin and fruit of *Malus pumila;*
    the grape extract comprises an extract of seeds of *Vitis vinifera;*
    the green tea extract comprises an extract of leaves of *Camellia sinensis*; and
    the olive extract comprises leaves of *Olea europaea.*

3. The method of claim 1, wherein the apple, grape, green tea, and olive extracts are present at a weight ratio of about 1:1:1:1.

4. The method of claim 1, wherein the apple, grape, green tea, and olive extracts are present at a weight ratio of about 6:1:3:1.

5. The method of claim 1, further comprising administering to the subject at least one secondary therapeutic agent.

6. The method of claim 5, wherein the at least one secondary therapeutic agent is co-administered to the subject with the therapeutically effective combination of apple, grape, green tea, and olive extracts.

7. The method of claim 5, wherein the at least one secondary therapeutic agent comprises a member selected from the group consisting of bergamot, mangosteen, berberine, arginine, citrulline, glutamine, zinc, beet, loclo, protein, curcumin, phytosterols, fish oil, CoQ10, vitamins, fiber, inulin, and combinations thereof.

* * * * *